(12) United States Patent
MacLachlan et al.

(10) Patent No.: US 7,915,399 B2
(45) Date of Patent: Mar. 29, 2011

(54) MODIFIED SIRNA MOLECULES AND USES THEREOF

(75) Inventors: Ian MacLachlan, Mission (CA); Adam Judge, Vancouver (CA)

(73) Assignee: Protiva Biotherapeutics, Inc., Burnaby, BC (CA)

( * ) Notice: Subject to any disclaimer, the term of this patent is extended or adjusted under 35 U.S.C. 154(b) by 226 days.

(21) Appl. No.: 11/760,627

(22) Filed: Jun. 8, 2007

(65) Prior Publication Data

US 2008/0249046 A1    Oct. 9, 2008

Related U.S. Application Data

(60) Provisional application No. 60/812,147, filed on Jun. 9, 2006.

(51) Int. Cl.
*C07H 21/04* (2006.01)
(52) U.S. Cl. ...................... 536/24.5
(58) Field of Classification Search .................. 536/24.5
See application file for complete search history.

(56) References Cited

U.S. PATENT DOCUMENTS

| | | | |
|---|---|---|---|
| 4,394,448 A | 7/1983 | Szoka, Jr. et al. | |
| 4,438,052 A | 3/1984 | Weder et al. | |
| 4,515,736 A | 5/1985 | Deamer | |
| 4,598,051 A | 7/1986 | Papahadjopoulos et al. | |
| 4,897,355 A | 1/1990 | Eppstein et al. | |
| 5,013,556 A | 5/1991 | Woodle et al. | |
| 5,171,678 A | 12/1992 | Behr et al. | |
| 5,208,036 A | 5/1993 | Eppstein et al. | |
| 5,225,212 A | 7/1993 | Martin et al. | |
| 5,264,618 A | 11/1993 | Felgner et al. | |
| 5,279,833 A | 1/1994 | Rose | |
| 5,283,185 A | 2/1994 | Epand et al. | |
| 5,320,906 A | 6/1994 | Eley et al. | |
| 5,545,412 A | 8/1996 | Eppstein et al. | |
| 5,578,475 A | 11/1996 | Jessee et al. | |
| 5,641,662 A | 6/1997 | Debs et al. | |
| 5,656,743 A | 8/1997 | Busch et al. | |
| 5,703,055 A | 12/1997 | Felgner et al. | |
| 5,705,385 A | 1/1998 | Bally et al. | |
| 5,820,873 A | 10/1998 | Choi et al. | |
| 5,976,567 A | 11/1999 | Wheeler et al. | |
| 5,981,501 A | 11/1999 | Wheeler et al. | |
| 6,534,484 B1 | 3/2003 | Wheeler et al. | |
| 6,586,410 B1 | 7/2003 | Wheeler et al. | |
| 6,680,068 B2 | 1/2004 | Campbell et al. | |
| 6,815,432 B2 | 11/2004 | Wheeler et al. | |
| 6,858,224 B2 | 2/2005 | Wheeler et al. | |
| 6,943,240 B2 | 9/2005 | Bauer et al. | |
| 7,341,738 B2 | 3/2008 | Semple et al. | |
| 2001/0044416 A1 | 11/2001 | McCluskie et al. | |
| 2003/0036516 A1 | 2/2003 | Agrawal | |
| 2003/0073640 A1 | 4/2003 | Beigelman et al. | |
| 2003/0077829 A1 | 4/2003 | MacLachlan | |
| 2003/0104044 A1 | 6/2003 | Semple et al. | |
| 2003/0143732 A1 | 7/2003 | Fosnaugh et al. | |
| 2003/0166001 A1 | 9/2003 | Lipford | |
| 2003/0175950 A1 | 9/2003 | McSwiggen | |
| 2004/0009949 A1 | 1/2004 | Krieg | |
| 2004/0142892 A1 | 7/2004 | Finn et al. | |
| 2004/0171033 A1 | 9/2004 | Baker et al. | |
| 2004/0192626 A1 | 9/2004 | McSwiggen et al. | |
| 2004/0198640 A1 | 10/2004 | Leake et al. | |
| 2004/0253723 A1 | 12/2004 | Tachas et al. | |
| 2004/0259247 A1 | 12/2004 | Tuschl et al. | |
| 2005/0020525 A1 | 1/2005 | McSwiggen et al. | |
| 2005/0064595 A1 | 3/2005 | MacLachlan et al. | |
| 2005/0100983 A1 | 5/2005 | Bauer et al. | |
| 2005/0119214 A1 | 6/2005 | Manoharan et al. | |
| 2005/0119273 A1 | 6/2005 | Lipford et al. | |
| 2005/0130911 A1 | 6/2005 | Uhlmann et al. | |
| 2005/0175682 A1 | 8/2005 | Heyes et al. | |
| 2005/0239733 A1 | 10/2005 | Jurk et al. | |
| 2005/0256073 A1 | 11/2005 | Lipford et al. | |
| 2005/0282188 A1 | 12/2005 | Haeberli et al. | |
| 2006/0008910 A1 | 1/2006 | MacLachlan et al. | |
| 2006/0009409 A1 * | 1/2006 | Woolf ........................... | 514/44 |
| 2006/0019916 A1 | 1/2006 | Krieg et al. | |
| 2006/0051405 A1 | 3/2006 | MacLachlan et al. | |
| 2006/0083780 A1 | 4/2006 | Heyes et al. | |
| 2006/0105976 A1 | 5/2006 | Soutschek et al. | |
| 2006/0134189 A1 | 6/2006 | MacLachlan et al. | |
| 2006/0142230 A1 | 6/2006 | Quay | |

(Continued)

FOREIGN PATENT DOCUMENTS

CA    2 359 180 A1    8/2000

(Continued)

OTHER PUBLICATIONS

Henry et al. JPET 292:468-479, 2000.*
Zhao et al. Biochemical Pharmacology 51:173-182, 1996.*
Allerson, C. R., et al., "Fully 2'-Modified Oligonucleotide Duplexes with Improved in Vitro Potency and Stability Compared to Unmodified Small Interfering RNA," J. Med. Chem., 2005, vol. 48, No. 4, pp. 901-904.
Arpicco, S., et al., "Preparation and Characterization of Novel Cationic Lipids Developed for Gene Transfection," Proceed. Int'l Symp. Control. Rel. Bioact. Mater. (Controlled Release Society, Inc.), 1999, vol. 26, pp. 759-760.
Arpicco, S., et al., "Synthesis, characterization and transfection activity of new saturated and unsaturated cationic lipids," IL Farmaco, 2004, vol. 59, pp. 869-878.
Beale, G., et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, 2003, vol. 11, No. 7, pp. 449-456.

(Continued)

*Primary Examiner* — Brian Whiteman
(74) *Attorney, Agent, or Firm* — Kilpatrick Townsend & Stockton LLP

(57) ABSTRACT

The present invention provides chemically modified siRNA molecules and methods of using such siRNA molecules to silence target gene expression. Advantageously, the modified siRNA of the present invention is less immunostimulatory than its corresponding unmodified siRNA sequence and retains full RNAi activity against the target sequence. The present invention also provides nucleic acid-lipid particles comprising a modified siRNA, a cationic lipid, and a non-cationic lipid, which can further comprise a conjugated lipid that inhibits aggregation of particles. Methods for identifying and/or modifying an siRNA having immunostimulatory properties are also provided.

11 Claims, 31 Drawing Sheets

U.S. PATENT DOCUMENTS

| | | | |
|---|---|---|---|
| 2006/0211642 A1* | 9/2006 | McSwiggen et al. ............ 514/44 |
| 2006/0217330 A1 | 9/2006 | Hartmann et al. |
| 2006/0240554 A1 | 10/2006 | Chen et al. |
| 2007/0031844 A1 | 2/2007 | Khvorova et al. |
| 2007/0042983 A1 | 2/2007 | Haeberli et al. |
| 2007/0135370 A1 | 6/2007 | MacLachlan et al. |
| 2007/0135372 A1 | 6/2007 | MacLachlan et al. |
| 2007/0218122 A1* | 9/2007 | MacLachlan et al. ......... 424/450 |
| 2008/0171716 A1 | 7/2008 | MacLachlan et al. |
| 2008/0249046 A1 | 10/2008 | MacLachlan et al. |
| 2008/0249294 A1 | 10/2008 | Haeberli et al. |
| 2009/0137500 A1 | 5/2009 | McSwiggen et al. |
| 2009/0270481 A1* | 10/2009 | Maclachlan et al. ......... 514/44 A |
| 2009/0286852 A1* | 11/2009 | Kariko et al. ............... 514/44 R |

FOREIGN PATENT DOCUMENTS

| | | |
|---|---|---|
| GB | 2 397 818 B | 3/2005 |
| WO | WO 91/16024 A1 | 10/1991 |
| WO | WO 93/05162 A1 | 3/1993 |
| WO | WO 93/12240 A1 | 6/1993 |
| WO | WO 93/12756 A2 | 7/1993 |
| WO | WO 93/24640 A2 | 12/1993 |
| WO | WO 93/25673 A1 | 12/1993 |
| WO | WO 95/02698 A1 | 1/1995 |
| WO | WO 95/18863 A1 | 7/1995 |
| WO | WO 95/35301 A1 | 12/1995 |
| WO | WO 96/02655 A1 | 2/1996 |
| WO | WO 96/10390 A1 | 4/1996 |
| WO | WO 96/41873 A1 | 12/1996 |
| WO | WO 98/51278 A2 | 11/1998 |
| WO | WO 00/44895 A1 | 8/2000 |
| WO | WO 02/34236 A2 | 5/2002 |
| WO | WO 02/44321 A2 | 6/2002 |
| WO | WO 02/072068 A2 | 9/2002 |
| WO | WO 02/087541 A1 | 11/2002 |
| WO | WO 03/029453 A2 | 4/2003 |
| WO | WO 03/070918 A2 | 8/2003 |
| WO | WO 03/086280 A2 | 10/2003 |
| WO | WO 03/097805 A2 | 11/2003 |
| WO | WO 2004/029212 A | 4/2004 |
| WO | WO 2004/046324 A | 6/2004 |
| WO | WO 2004/065546 A2 | 8/2004 |
| WO | WO 2004/073685 A1 | 9/2004 |
| WO | WO 2004/110499 A1 | 12/2004 |
| WO | WO 2005/007196 A2 | 1/2005 |
| WO | WO 2005/019453 A3 | 3/2005 |
| WO | WO 2005/021044 | 3/2005 |
| WO | WO 2005/026372 A1 | 3/2005 |
| WO | WO 2005/044981 A3 | 5/2005 |
| WO | WO 2005/078094 A2 | 8/2005 |
| WO | WO 2005/120152 A2 | 12/2005 |
| WO | WO 2005/121348 A1 | 12/2005 |
| WO | WO 2006/074546 A1 | 7/2006 |
| WO | WO 2007/048046 A2 | 4/2007 |
| WO | WO 2007/051303 A1 | 5/2007 |
| WO | WO 2008/019486 A1 | 2/2008 |

OTHER PUBLICATIONS

Braasch, D. A., et al., "RNA Interference in Mammalian Cells by Chemically-Modified RNA," Biochemistry, 2003, vol. 42, No. 26, pp. 7967-7975.

Cevc, G., "How Membrane Chain-Melting Phase-Transition Temperature is Affected by the Lipid Chain Asymmetry and Degree of Unsaturation: An Effective Chain-Length Model," Biochemistry, 1991, vol. 30, pp. 7186-7193.

Chiu, Y., et al., "siRNA function in RNAi: A chemical modification analysis,"RNA, 2003, vol. 9, No. 9, pp. 1034-1048.

Czauderna, F., et al., "Structural variations and stabilizing modifications of synthetic siRNAs in mammalian cells," Nucleic Acids Research, 2003, vol. 31, No. 11, pp. 2705-2716.

Elbashir, S. M., et al., "Functional anatomy of siRNAs for mediating efficient RNAi in *Drosophila melanogaster* embryo lysate," The EMBO Journal, 2001, vol. 20, No. 23, pp. 6877-6888.

Hornung, V., et al., "Sequence-specific potent induction of IFN-α by short interfering RNA in plasmacytoid dendritic cells through TLR7," Nature Medicine, 2005, vol. 11, No. 3, pp. 263-270.

Jiang, L., et al., "Comparison of protein precipitation methods for sample preparation prior to proteomic analysis," Journal of Chromatography A, 2004, vol. 1023, pp. 317-320.

Judge, A. D., et al., "Design of Noninflammatory Synthetic siRNA Mediating Potent Gene Silencing in Vivo," Molecular Therapy, 2006, vol. 13, No. 3, pp. 494-505.

Judge, A. D., et al., "Sequence-dependent stimulation of the mammalian innate immune response by synthetic siRNA," Nature Biotechnology, 2005, vol. 23, No. 4, pp. 457-462.

Keough, K., "Influence of chain unsaturation and chain position on thermotropism and intermolecular interactions in membranes," Biochem. Soc. Transactions, 1990, vol. 18, No. 5, pp. 835-837.

Manoharan, M., "RNA interference and chemically modified small interfering RNAs," Current Opinion in Chemical Biology, 2004, vol. 8, pp. 570-579.

Martinez, A., et al., "Small Interfering RNA Molecules as Potential Anti-Human Hepatitis C Virus Agents: Identification and Characterization of Two siRNA Molecules Highly Conserved in the Major Genotypes of the Virus," Preclinica, 2003, vol. 1, No. 5, pp. 274-283.

Morrissey, D. V., et al., "Potent and persistent in vivo anti-HBV activity of chemically modified siRNAs," Nature Biotechnology, 2005, vol. 23, No. 8, pp. 1002-1007.

Paul, C., et al., "Effective expression of small interfering RNA in human cells," Nature Biotech., 2002, vol. 20, pp. 505-508.

Prakash, T. P., et al., "Positional Effect of Chemical Modifications on Short Interference RNA Activity in Mammalian Cells," J. Med. Chem., 2005, vol. 48, No. 13, pp. 4247-4253.

Sioud, M., "Single-stranded small interfering RNA are more immunostimulatory than their double-stranded counterparts: a central role for 2'-hydroxy uridines in immune responses," European Journal of Immunology, 2006, vol. 36, pp. 1222-1230.

Soutschek, J., et al., "Therapeutic silencing of an endogenous gene by systemic administration of modified siRNAs," Nature, 2004, vol. 432, pp. 173-178.

Spagnou, S., et al., "Lipidic Carriers of siRNA: Differences in the Formulation, Cellular Uptake, and Delivery with Plasmid DNA," Biochemistry, 2004, vol. 43, pp. 13348-13356.

U.S. Appl. No. 60/358,580, Beigelman et al.

Alexopoulou, L. et al., "Recognition of double-stranded RNA and activation of NF-kappaB by Toll-like receptor 3," Nature, 2001, vol. 413, No. 6857, pp. 732-738.

Allerson et al. "Chemically-modified siRNA motifs with enhanced in vitro activity and stability," General Oral Session, Division of Medicinal Chemistry, the 227th ACS National Meeting, 2004, Abstract No. MEDI 174.

Aoki, H. et al. "Inhibition of motility and invasiveness of renal cell carcinoma induced by short interfering RNA transfection of β1, 4GalNAc transferase," FEBS Letters, 2004, vol. 567, pp. 203-208.

Ballas, N. et al. "Liposomes bearing a quarternary ammonium detergent as an efficient vehicle for functional transfer of TMV-RNA into plant protoplasts," Biochim. Biophys. Acta, 1998, pp. 8-18, vol. 939.

Barinaga, M. "Step Taken Toward Improved Vectors for Gene Transfer," Science, 1994, p. 1326, vol. 266.

Barrat et al. "Nucleic acids of mammalian origin can act as endogenous ligands for Toll-like receptors and may promote systemic lupus erythematosus," Journal of Experimental Medicine, 2005, vol. 202, No. 8, pp. 1131-1139.

Behr, J-P., "Synthetic Gene-Transfer Vectors," Acc. Chem. Res. 1993, pp. 274-278, vol. 26.

Bridge, A.J. et al., "Induction of an interferon response by RNAi vectors in mammalian cells," Nature Genetics, Jul. 2003, vol. 34, No. 3, pp. 263-264.

Brigham, K. et al. "Rapid Communication: In vivo Transfection of Murine Lungs with a Functioning Prokaryotic Gene Using a Liposome Vehicle," Am. J. Med. Sci., 1989, pp. 278-281, vol. 298.

Claims Chart under Exhibit O in the Protest Under 37 C.F.R. §1.291 filed on Oct. 2, 2009, for U.S. Appl. No. 12/367,439, 6 pages.

Cortesi, R., et al. "Effect of cationic liposome composition on in vitro cytotoxicity and protective effect on carried DNA," International Journal of Pharmaceutics, 1996, pp. 69-78, vol. 139.

Crystal, R. "Transfer of Genes to Humans: Early Lessons and Obstacles to Success," Science, 1995, pp. 404-410, vol. 270.

Culver, K. "The First Human Gene Therapy Experiment," Gene Therapy: A Handbook for Physicians, 1994, pp. 33-40.
Dalby, B. et al. "Advanced transfection with Lipofectamine 2000 reagent: primary neurons, siRNA, and high-throughput applications." Methods (2004), 33(2):95-103.
Declaration Under 37 C.F.R. §1.131 of Ian MacLachlan and Adam Judge filed on Jan. 30, 2009, in U.S. Appl. No. 11/592,756, 17 pages.
Declaration Under 37 C.F.R. §1.132 of Ian MacLachlan and Adam Judge filed on Jan. 30, 2009, in U.S. Appl. No. 11/592,756, 49 pages.
Declaration under 37 CFR §1.63 filed on Feb. 28, 2008, in U.S. Appl. No. 11/760,627, 1 page.
Diebold, S.S. et al., "Innate antiviral responses by means of TLR7-mediated recognition of single-stranded RNA," Science, 2004, vol. 303, No. 5663, pp. 1529-1531.
Duzgunes, N. "Membrane Fusion," Subcellular Biochemistry, 1985, pp. 195-286, vol. 11.
Dwarki, V.J. et al., "Cationic Liposime-Mediated RNA Transfection," Methods in Enzymology, 1993, pp. 644-654, vol. 217.
Enoch, H. et al. "Formation and properties of 1000-Å-diameter, single-bilayer phospholipid vesicles," Proc. Natl. Acad. Sci. USA, 1979, pp. 145-149, vol. 76, No. 1.
Felgner, J. et al., "Cationic Lipid-Mediated Transfection in Mammalian Cells: "Lipofection"," J. Tiss. Cult. Meth., 1993, pp. 63-68, vol. 15.
Felgner, J.H. et al., "Enhanced Gene Delivery and Mechanism Studies with a Novel Series of Cationic Lipid Formulations," The Journal of Biological Chemistry, Jan. 1994, pp. 2550-2561, vol. 269, No. 4.
Felgner, P. et al., "Lipofection: A highly efficient, lipid-mediated DNA-transfection procedure," Proc. Natl. Acad. Sci. USA, 1987, pp. 7413-7417, vol. 84.
Final Office Action mailed on Nov. 2, 2009, in U.S. Appl. No. 11/592,756, 25 pages.
Flynn, M.A., et al. "Efficient delivery of small interfering RNA for inhibition of IL-12p40 expression in vivo," Journal of Inflammation, 2004, vol. 1, No. 4, pp. 1-12.
Gao, X. et al., "A Novel Cationic Liposome Reagent for Efficient Transfection of Mammalian Cells," Biochem. Biophys. Res. Comm., 1991, pp. 280-285, vol. 179.
GenBank accession No. BD134629 from JP 2002051786 patent application (Komori Hisafumi) Feb. 19, 2002.
Gershon, H. et al., "Mode of Formation and Structural Feature of DNA-Cationic Liposome Complexes Used for Transfection," Biochemistry, 1993, pp. 7413-7151, vol. 32.
Guy-Caffey, J. et al., "Novel Polyaminolipids Enhance the Cellular Uptake of Oligonucleotides," The Journal of Biological Chemistry, Dec. 1995, pp. 31391-31396, vol. 270, No. 52.
Hafez et al. "On the mechanism whereby cationic lipids promote intracellular delivery of polynucleic acids," Gene Therapy, 2001, vol. 8, pp. 1188-1196.
Hamada, Makiko et al. "Effects on RNA Interference in Gene Expression (RNAi) in Cultured Mammalian Cells of Mismatches and the Introduction of Chemical Modifications at the 3'-Ends of siRNAs," Antisense and Nucleic Acid Drug Development, 2002, vol. 12, pp. 301-309.
Hawley-Nelson et al., "LipofectAmine™ Reagent: A New, Higher Efficiency Polycationic Liposome Transfection Reagent," Focus, 1993, p. 73-80, vol. 15, No. 3.
Heil, F. et al. "Species-specific recognition of single-stranded RNA via Toll-like receptor 7 and 8," Science, 2004, vol. 303, pp. 1526-1529.
Heyes et al. "Cationic lipid saturation influences intracellular delivery of encapsulated nucleic acids," Journal of Controlled Release, 2005, vol. 107, pp. 276-287.
Hyde, S et al., "Correction of the ion transport defect in cystic fibrosis transgenic mice by gene therapy," Nature, 1993, pp. 250-256, vol. 362.
Jeffs et al. "A scalable, extrusion-free method for efficient liposomal encapsulation of plasmid DNA," Pharmaceutical Research, 2005, vol. 22 No. 3, pp. 362-372.
Juliano R., and Stamp, D., "The Effect of Particle Size and Charge on the Clearance Rates of Liposomes and Liposome Encapsulated Drugs," Biochem. Biophys. Res. Commun., 1975, pp. 651-658, vol. 63.

Jurk et al. "Modulating responsiveness of human TLR7 and 8 to small molecule ligands with T-rich phosphorothiate oligodeoxynucleotides," Eur. J. Immunol., 2006, vol. 36, pp. 1815-1826.
Kariko et al. Suppression of RNA recognition by Toll-like receptors: the impact of nucleoside modification and the evolutionary origin of RNA. Immunity, Aug. 2005, vol. 23, No. 2, pp. 165-175.
Karikó, K. et al., "Small Interfering RNAs Mediate Sequence-Independent Gene Suppression and Induce Immune Activation by Signaling through Toll-Like Receptor 3," The Journal of Immunology, 2004, vol. 172, pp. 6545-6549.
Kim, D.H. et al., "Interferon induction by siRNAs and ssRNAs synthesized by phage polymerase," Nat. Biotechnol., 2004, vol. 22, No. 3, pp. 321-325.
Legendre, J.Y. and Szoka, F., "Delivery of Plasmid DNA into Mammalian Cell Lines Using pH-Sensitive Liposomes: Comparison with Cationic Liposomes," Pharm. Res., 1992, pp. 1235-1242, vol. 9, No. 10.
Leventis, R. et al., "Interactions of mammalian cells with lipid dispersions containing novel metabolizable cationic amphiphiles," Biochem. Biophys. Acta, 1990, p. 124, vol. 1023.
Lund, J.M. et al., "Recognition of single-stranded RNA viruses by Toll-like receptor 7," Proc. Natl. Acad. Sci. USA, 2004, vol. 101, No. 15, pp. 5598-5603.
Marshall, E., "Gene Therapy's Growing Pains," Science, 1995, pp. 1050-1055, vol. 269.
Moss, E.G. et al., "Small-interfering RNAs in the radar of the interferon system," Nature Cell Biology, Sep. 2003, vol. 5, No. 9, pp. 771-772.
Nguyen et al., "RNAi Therapeutics: An Update on Delivery," Current Opinion in Molecular Therapeutics, 2008, vol. 10(2): 158-67.
Non-Final Office Action mailed on Apr. 17, 2009, in U.S. Appl. No. 11/592,756, 29 pages.
Non-Final Office Action mailed on Aug. 17, 2009, in U.S. Appl. No. 11/760,627, 9 pages.
Non-Final Office Action mailed on Feb. 12, 2008, in U.S. Appl. No. 11/592,756, 11 pages.
Non-Final Office Action mailed on Jul. 31, 2008, in U.S. Appl. No. 11/592,756, 26 pages.
Orkin et al., NIH Report: Report and Recommendations of the Panel to Assess the NIH Investment in Research on Gene Therapy, 1995.
Prakash et al. "Positional effects of chemical modification on siRNA activity," General Oral Session, Division of Medicinal Chemistry, The 227$^{th}$ ACS National Meeting, 2004, Abstract No. MEDI 175.
Protest Under 37 CFR §1.291 filed on Oct. 2, 2009, in U.S. Appl. No. 12/367,439, 17 pages.
Puyal, C et al., "A new cationic liposome encapsulating genetic material: A potential delivery system for polynucleotides," Eur. J. Biochem., 1995, pp. 697-703, vol. 228.
Response to Non-Final Office Action filed on Jan. 30, 2009, in U.S. Appl. No. 11/592,756, 27 pages.
Response to Protest Under 37 CFR 1.291 filed on Dec. 9, 2009, in U.S. Appl. No. 12/367,439, 8 pages.
Response to Restriction Requirement filed on Apr. 23, 2009, in U.S. Appl. No. 11/760,627, 6 pages.
Sioud, M. "Induction of inflammatory Cyokines and Interferon responses by double-stranded and single stranded siRNAs is sequence-dependent and requires endosomal localization," Journal of Molecular Biology, 2005, vol. 348, pp. 1079-1090.
Sioud, M. et al., "Cationic liposome-mediated delivery of siRNAs in adult mice," Biochem. Biophys. Res. Commun., 2003, vol. 312, No. 4, pp. 1220-1225.
Sledz, C.A. et al., "Activation of the interferon system by short-interfering RNAs," Nature Cell Biology, Sep. 2003, vol. 5, No. 9, pp. 834-839.
Stamatatos, L. et al., "Interactions of Cationic Lipid Vesicles with Negatively Charged Phospholipid Vesicles and Biological Membranes," Biochemistry, 1988, pp. 3917-3925, vol. 27.
Stunz et al. "Inhibitory oligonucleotides specifically block effects of stimulatory CpG oligonucleotides in B cells." European Journal of Immunology, 2002, vol. 32, No. 5, pp. 1212-1222.

Szoka, F. et al., "Comparative Properties and Methods of Preparation of Lipid Vesicles (Liposomes)," Ann. Rev. Biophys. Bioeng., 1980, pp. 467-508, vol. 9.

Szoka, F. et al., "Procedure for preparation of liposomes with large internal aqueous space and high capture by reverse-phase evaporation," Proc. Natl. Acad. Sci. USA, 1978, pp. 4194-4198, vol. 75, No. 9.

Tranchant et al. "Physicochemical optimisation of plasmid delivery by cationic lipids," The Journal of Gene Medicine, 2004, vol. 6, pp. S24-S35.

Usman, N., "Development of siRNA Therapeutics," presented at Nucleic Acids World Symposium, Sep. 16, 2003, Boston, MA; also presented as Zinnan, S., "Moving Towards Therapeutic siRNA," presented at RNA Tools Conference, Oct. 2003, North Carolina, 53 pages.

Van Der Woude, I. et al., "Parameters influencing the introduction of plasmid DNA into cells by the use of synthetic amphiphiles as a carrier system," Biochimica et Biophysica Acta, 1995, pp. 34-40, vol. 1240.

Wilson, R. et al., "Counterion-Induced Condensation of Deoxyribonucleic Acid. A Light-Scattering Study." Biochemistry, 1979, pp. 2192-2196, vol. 18.

Woodle, M.C. et al., "Versatility in lipid compositions showing prolonged circulation with sterically stabilized liposomes," Biochim. Biophys. Acta, 1992, pp. 193-200, vol. 1105.

Zhu, N., et al., "Systemic Gene Expression After Intravenous DNA Delivery into Adult Mice," Science, 1993, pp. 209-211, vol. 261.

Zimmermann et al. "RNAi-mediated gene silencing in non-human primates," Nature, 2006, vol. 441, pp. 111-114.

Advisory Action mailed on Mar. 3, 2010 in U.S. Appl. No. 11/511,855, 3 pages.

Bosscher et al. "The Interplay between the Glucocorticoid Receptor and Nuclear Factor-$^k$B or Activator Protein-1:Molecular Mechanisms for Gene Repression," Endocrine Reviews 24:488-522, 2003.

Brummelkamp et al. "A System for Stable Expression of Short Interfering RNAs in Mammalian Cells," Science, 2002, vol. 296, pp. 550-553.

Budker et al. Mechanism of plasmid delivery by hydrodynamic tail vein injection. II. Morphological studies, 2006, The journal of Gene Medicine, vol. 8, pp. 874-888.

Christensen et al. Toll-like Receptor 7 and TLR9 dictate autoantibody specificity and have opposing inflammatory and regulatory roles in a murine model of lupus, Sep. 2006, Immunity, vol. 25, pp. 417-428.

Dandona et al. "Effect of dexamethasone on reactive oxygen species generation by leukocytes and plasma interleukin-10 concentrations: A pharmacodynamic study," Clin Pharmacol Ther. 1999, 66(1): 58-65.

Final Office Action mailed on Jan. 13, 2009 in U.S. Appl. No. 11/511,855, 16 pages.

Final Office Action mailed on Jan. 27, 2010 in U.S. Appl. No. 11/511,855, 19 pages.

Final Office Action mailed on Oct. 22, 2009 in U.S. Appl. No. 11/839,065, 17 pages.

Gruneich, J.A., et al., "Cationic corticosteroid for nonviral gene delivery," Gene Ther., 2004, vol. 11, pp. 668-674.

Interview Summary mailed on Aug. 5, 2010 in U.S. Appl. No. 11/592,756, 3 pages.

Interview Summary mailed on Jul. 29, 2010 in U.S. Appl. No. 11/592,756, 3 pages.

Lee et al., siRNA-getting the message out, 2006, European Journal of Pharmaceutical Sciences, vol. 27, pp. 401-410.

Lewis et al. Efficient delivery of siRNA for inhibition of gene expression in postnatal mice, 2002, Nature Genetics, vol. 32, pp. 107-108.

Liu, Y., et al., "Strain-based Genetic Differences Regulate the Efficiency of Systemic Gene Delivery as Well as Expression," J. Biol. Chem., 2002, vol. 277, pp. 4966-4972.

McCaffrey et al. RNA interference in adult mice, 2002, Nature, vol. 418, pp. 38-39.

Mena et al., Innate immunity responses induced by CpG oligodeoxyribonucleotide stimulation of ovine blood mononuclear cells, 2003, Immunity, vol. 110, pp. 250-2570.

Morrissey et al. Activity of stabilized short interfering RNA in a mouse model of hepatitis B virus replication, 2005, Hepatology, vol. 41, pp. 1349-1356.

Non-Final Office Action mailed on Aug. 25, 2010 in U.S. Appl. No. 11/839,065, 18 pages.

Non-Final Office Action mailed on Feb. 27, 2009 in U.S. Appl. No. 11/839,065, 17 pages.

Non-Final Office Action mailed on Jun. 25, 2010 in U.S. Appl. No. 11/592,756, 38 pages.

Non-Final Office Action mailed on Jun. 26, 2009 in U.S. Appl. No. 11/511,855, 17 pages.

Non-Final Office Action mailed on Jun. 6, 2008 in U.S. Appl. No. 11/511,855, 15 pages.

Non-Final Office Action mailed on May 11, 2010 in U.S. Appl. No. 11/511,855, 28 pages.

Non-Final Office Action mailed on Nov. 14, 2007 in U.S. Appl. No. 11/511,855, 18 pages.

Przybylska, M., et al., "Partial correction of the α-galactosidase A deficiency and reduction of glycolipid storage in Fabry mice using synthetic vectors," J. Gene Med., 2004, vol. 6, pp. 85-92.

Pisitkun et al. "Autoreactive B Cell Responses to RNA-Related Antigens Due to TLR7 Gene Duplication," Science, 2006, vol. 312, pp. 1669-1672.

Restriction Requirement mailed on Jul. 31, 2008 in U.S. Appl. No. 11/839,065, 7 pages.

Restriction Requirement mailed on Apr. 23, 2007 in U.S. Appl. No. 11/511,855, 6 pages.

Restriction Requirement mailed on Dec. 23, 2008 in U.S. Appl. No. 11/760,627, 13 pages.

Restriction Requirement mailed on Feb. 12, 2008 in U.S. Appl. No. 11/592,756, 11 pages.

Schmidt, Charlie "Negotiating the RNAi patent thicket," Mar. 2007, Nature Biotechnology, vol. 25, pp. 273-275.

Subramanian et al. "A Tlr7 translocation accelerates systemic autoimmunity in murine lupus," PNAS, 2006, vol. 103, No. 26, pp. 9970-9975.

Sugiyama et al. CpG RNA: Identification of novel single-stranded RNA that stimulates human CD14+CD11c+monocytes, 2005, the Journal of Immunology, vol. 174, pp. 2273-2279.

Sun et al., TLR7/9 dictate autoantibody specificity and have opposing inflammatory and regulatory roles in a murine model of lupus, Sep. 2006, Immunity, vol. 25, pp. 417-428.

Tan et al. "The Inhibitory Role of CpG Immunostimulatory Motifs in Cationic Lipid Vector-Mediated Transgene Expression in Vivo," Human Gene Therapy, 1999, 10:2153-2161.

Final Office Action mailed on Nov. 23, 2010 in U.S. Appl. No. 11/511,855, 36 pages.

* cited by examiner

SEQUENCE LISTING

<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      synthetic firefly luciferase (Luc) antisense siRNA
<220> FEATURE:
<223> OTHER INFORMATION: Description of Artificial Sequence:synthetic
      firefly luciferase (Luc) antisense siRNA

<400> SEQUENCE: 1
uaucucuuca uagccuuaut t      21

```
<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      synthetic green fluorescent protein (GFP) antisense siRNA
<220> FEATURE:
<223> OTHER INFORMATION: Description of Artificial Sequence:synthetic
      green fluorescent protein (GFP) antisense siRNA

<400> SEQUENCE: 2
uucaccuuga ugccguucut t                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence:synthetic
      beta-galactosidase (beta-gal) native (S)
      unmodified sense strand siRNA

<400> SEQUENCE: 3
uugauguguu uagucgcuau u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence:synthetic
      beta-galactosidase (beta-gal) 2'-O-methyl modified
      2'OMe GU(S) sense strand siRNA
<220> FEATURE:
<221> NAME/KEY: modified_base
<222> LOCATION: (5)
<223> OTHER INFORMATION: u = um
<220> FEATURE:
<221> NAME/KEY: modified_base
<222> LOCATION: (6)
<223> OTHER INFORMATION: g = gm
<220> FEATURE:
<221> NAME/KEY: modified_base
<222> LOCATION: (7)
<223> OTHER INFORMATION: u = um
<220> FEATURE:
<221> NAME/KEY: modified_base
<222> LOCATION: (8)
<223> OTHER INFORMATION: g = gm
<220> FEATURE:
<221> NAME/KEY: modified_base
<222> LOCATION: (9)
<223> OTHER INFORMATION: u = um

<400> SEQUENCE: 4
uugauguguu uagucgcuau u                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence:synthetic
      beta-galactosidase (beta-gal) 2'-O-methyl modified
      2'OMe 3xU(S) sense strand siRNA
<220> FEATURE:
<221> NAME/KEY: modified_base
<222> LOCATION: (5)
<223> OTHER INFORMATION: u = um
<220> FEATURE:
<221> NAME/KEY: modified_base
<222> LOCATION: (7)
<223> OTHER INFORMATION: u = um
```

```
<220> FEATURE:
<221> NAME/KEY: modified_base
<222> LOCATION: (9)
<223> OTHER INFORMATION: u = um

<400> SEQUENCE: 5
uugauguguu uagucgcuau u                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence:synthetic
      beta-galactosidase (beta-gal) 2'-O-methyl modified
      2'OMe 2xG(S) sense strand siRNA
<220> FEATURE:
<221> NAME/KEY: modified_base
<222> LOCATION: (6)
<223> OTHER INFORMATION: g = gm
<220> FEATURE:
<221> NAME/KEY: modified_base
<222> LOCATION: (8)
<223> OTHER INFORMATION: g = gm

<400> SEQUENCE: 6
uugauguguu uagucgcuau u                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence:synthetic
      beta-galactosidase (beta-gal) 2'-O-methyl modified
      2'OMe 2xG 3'(S) sense strand siRNA
<220> FEATURE:
<221> NAME/KEY: modified_base
<222> LOCATION: (13)
<223> OTHER INFORMATION: g = gm
<220> FEATURE:
<221> NAME/KEY: modified_base
<222> LOCATION: (16)
<223> OTHER INFORMATION: g = gm

<400> SEQUENCE: 7
uugauguguu uagucgcuau u                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence:synthetic
      beta-galactosidase (beta-gal) native (AS)
      unmodified antisense strand siRNA
<220> FEATURE:
<221> NAME/KEY: modified_base
<222> LOCATION: (1)
<223> OTHER INFORMATION: u modified by 5' phosphate

<400> SEQUENCE: 8
uagcgacuaa acacaucaau u                                              21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence:synthetic
      beta-galactosidase (beta-gal) 2'-O-methyl modified
      2'OMe AC(AS) antisense strand siRNA
```

```
<220> FEATURE:
<221> NAME/KEY: modified_base
<222> LOCATION: (1)
<223> OTHER INFORMATION: u modified by 5' phosphate
<220> FEATURE:
<221> NAME/KEY: modified_base
<222> LOCATION: (11)
<223> OTHER INFORMATION: a = 2'-O-methyl adenosine
<220> FEATURE:
<221> NAME/KEY: modified_base
<222> LOCATION: (12)
<223> OTHER INFORMATION: c = cm
<220> FEATURE:
<221> NAME/KEY: modified_base
<222> LOCATION: (13)
<223> OTHER INFORMATION: a = 2'-O-methyl adenosine
<220> FEATURE:
<221> NAME/KEY: modified_base
<222> LOCATION: (14)
<223> OTHER INFORMATION: c = cm
<220> FEATURE:
<221> NAME/KEY: modified_base
<222> LOCATION: (15)
<223> OTHER INFORMATION: a = 2'-O-methyl adenosine

<400> SEQUENCE: 9
uagcgacuaa acacaucaau u                                              21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence:synthetic
      apolipoprotein B-1 (apoB-1) native (S) unmodified
      sense strand siRNA

<400> SEQUENCE: 10
gucaucacac ugaauaccaa u                                              21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence:synthetic
      apolipoprotein B-1 (apoB-1) 2'-O-methyl modified
      2'OMe U(S) sense strand siRNA
<220> FEATURE:
<221> NAME/KEY: modified_base
<222> LOCATION: (2)
<223> OTHER INFORMATION: u = um
<220> FEATURE:
<221> NAME/KEY: modified_base
<222> LOCATION: (5)
<223> OTHER INFORMATION: u = um
<220> FEATURE:
<221> NAME/KEY: modified_base
<222> LOCATION: (11)
<223> OTHER INFORMATION: u = um
<220> FEATURE:
<221> NAME/KEY: modified_base
<222> LOCATION: (15)
<223> OTHER INFORMATION: u = um
<220> FEATURE:
<221> NAME/KEY: modified_base
<222> LOCATION: (21)
<223> OTHER INFORMATION: u = um

<400> SEQUENCE: 11
gucaucacac ugaauaccaa u                                              21

<210> SEQ ID NO 12
<211> LENGTH: 21
```

```
<212> TYPE: RNA
<213> ORGANISM: Artificial Sequence
<220> FEATURE:
<223> OTHER INFORMATION: Description of Artificial Sequence:synthetic
      apolipoprotein B-1 (apoB-1) 2'-O-methyl modified
      2'OMe G(S) sense strand siRNA
<220> FEATURE:
<221> NAME/KEY: modified_base
<222> LOCATION: (1)
<223> OTHER INFORMATION: g = gm
<220> FEATURE:
<221> NAME/KEY: modified_base
<222> LOCATION: (12)
<223> OTHER INFORMATION: g = gm

<400> SEQUENCE: 12
gucaucacac ugaauaccaa u                                                   21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence:synthetic
      apolipoprotein B-1 (apoB-1) 2'-O-methyl modified
      2'OMe C(S) sense strand siRNA
<220> FEATURE:
<221> NAME/KEY: modified_base
<222> LOCATION: (3)
<223> OTHER INFORMATION: c = cm
<220> FEATURE:
<221> NAME/KEY: modified_base
<222> LOCATION: (6)
<223> OTHER INFORMATION: c = cm
<220> FEATURE:
<221> NAME/KEY: modified_base
<222> LOCATION: (8)
<223> OTHER INFORMATION: c = cm
<220> FEATURE:
<221> NAME/KEY: modified_base
<222> LOCATION: (10)
<223> OTHER INFORMATION: c = cm
<220> FEATURE:
<221> NAME/KEY: modified_base
<222> LOCATION: (17)..(18)
<223> OTHER INFORMATION: c = cm

<400> SEQUENCE: 13
gucaucacac ugaauaccaa u                                                   21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence:synthetic
      apolipoprotein B-1 (apoB-1) 2'-O-methyl modified
      2'OMe A(S) sense strand siRNA
<220> FEATURE:
<221> NAME/KEY: modified_base
<222> LOCATION: (4)
<223> OTHER INFORMATION: a = 2'-O-methyl adenosine
<220> FEATURE:
<221> NAME/KEY: modified_base
<222> LOCATION: (7)
<223> OTHER INFORMATION: a = 2'-O-methyl adenosine
<220> FEATURE:
<221> NAME/KEY: modified_base
<222> LOCATION: (9)
<223> OTHER INFORMATION: a = 2'-O-methyl adenosine
<220> FEATURE:
<221> NAME/KEY: modified_base
<222> LOCATION: (13)..(14)
<223> OTHER INFORMATION: a = 2'-O-methyl adenosine
<220> FEATURE:
<221> NAME/KEY: modified_base
```

```
<222> LOCATION: (16)
<223> OTHER INFORMATION: a = 2'-O-methyl adenosine
<220> FEATURE:
<221> NAME/KEY: modified_base
<222> LOCATION: (19)..(20)
<223> OTHER INFORMATION: a = 2'-O-methyl adenosine

<400> SEQUENCE: 14
gucaucacac ugaauaccaa u                                              21

<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence:synthetic
      apolipoprotein B-1 (apoB-1) native (AS) unmodified
      antisense strand siRNA
<220> FEATURE:
<221> NAME/KEY: modified_base
<222> LOCATION: (1)
<223> OTHER INFORMATION: a modified by 5' phosphate

<400> SEQUENCE: 15
auugguauuc agugugauga cac                                            23

<210> SEQ ID NO 16
<211> LENGTH: 23
<212> TYPE: RNA
<213> ORGANISM: Artificial Sequence
<220> FEATURE:
<223> OTHER INFORMATION: Description of Artificial Sequence:synthetic
      apolipoprotein B-1 (apoB-1) 2'-O-methyl modified
      2'OMe GU(AS) antisense strand siRNA
<220> FEATURE:
<221> NAME/KEY: modified_base
<222> LOCATION: (1)
<223> OTHER INFORMATION: a modified by 5' phosphate
<220> FEATURE:
<221> NAME/KEY: modified_base
<222> LOCATION: (12)
<223> OTHER INFORMATION: g = gm
<220> FEATURE:
<221> NAME/KEY: modified_base
<222> LOCATION: (13)
<223> OTHER INFORMATION: u = um
<220> FEATURE:
<221> NAME/KEY: modified_base
<222> LOCATION: (14)
<223> OTHER INFORMATION: g = gm
<220> FEATURE:
<221> NAME/KEY: modified_base
<222> LOCATION: (15)
<223> OTHER INFORMATION: u = um
<220> FEATURE:
<221> NAME/KEY: modified_base
<222> LOCATION: (16)
<223> OTHER INFORMATION: g = gm

<400> SEQUENCE: 16
auugguauuc agugugauga cac                                            23

<210> SEQ ID NO 17
<211> LENGTH: 23
<212> TYPE: RNA
<213> ORGANISM: Artificial Sequence
<220> FEATURE:
<223> OTHER INFORMATION: Description of Artificial Sequence:synthetic
      apolipoprotein B-1 (apoB-1) 2'-O-methyl modified
      2'OMe U(AS) antisense strand siRNA
<220> FEATURE:
<221> NAME/KEY: modified_base
<222> LOCATION: (1)
<223> OTHER INFORMATION: a modified by 5' phosphate
```

```
<220> FEATURE:
<221> NAME/KEY: modified_base
<222> LOCATION: (2)..(3)
<223> OTHER INFORMATION: u = um
<220> FEATURE:
<221> NAME/KEY: modified_base
<222> LOCATION: (6)
<223> OTHER INFORMATION: u = um
<220> FEATURE:
<221> NAME/KEY: modified_base
<222> LOCATION: (8)..(9)
<223> OTHER INFORMATION: u = um
<220> FEATURE:
<221> NAME/KEY: modified_base
<222> LOCATION: (13)
<223> OTHER INFORMATION: u = um
<220> FEATURE:
<221> NAME/KEY: modified_base
<222> LOCATION: (15)
<223> OTHER INFORMATION: u = um
<220> FEATURE:
<221> NAME/KEY: modified_base
<222> LOCATION: (18)
<223> OTHER INFORMATION: u = um

<400> SEQUENCE: 17
auugguauuc agugugauga cac                                              23

<210> SEQ ID NO 18
<211> LENGTH: 23
<212> TYPE: RNA
<213> ORGANISM: Artificial Sequence
<220> FEATURE:
<223> OTHER INFORMATION: Description of Artificial Sequence:synthetic
      apolipoprotein B-1 (apoB-1) 2'-O-methyl modified
      2'OMe G(AS) antisense strand siRNA
<220> FEATURE:
<221> NAME/KEY: modified_base
<222> LOCATION: (1)
<223> OTHER INFORMATION: a modified by 5' phosphate
<220> FEATURE:
<221> NAME/KEY: modified_base
<222> LOCATION: (4)..(5)
<223> OTHER INFORMATION: g = gm
<220> FEATURE:
<221> NAME/KEY: modified_base
<222> LOCATION: (12)
<223> OTHER INFORMATION: g = gm
<220> FEATURE:
<221> NAME/KEY: modified_base
<222> LOCATION: (14)
<223> OTHER INFORMATION: g = gm
<220> FEATURE:
<221> NAME/KEY: modified_base
<222> LOCATION: (16)
<223> OTHER INFORMATION: g = gm
<220> FEATURE:
<221> NAME/KEY: modified_base
<222> LOCATION: (19)
<223> OTHER INFORMATION: g = gm

<400> SEQUENCE: 18
auugguauuc agugugauga cac                                              23

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence:synthetic
      apolipoprotein B mismatch native (S) unmodified
      sense strand siRNA

<400> SEQUENCE: 19
gugaucagac ucaauacgaa u                                                21
```

```
<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence:synthetic
      apolipoprotein B mismatch 2'-O-methyl modified
      2'OMe U(S) sense strand siRNA
<220> FEATURE:
<221> NAME/KEY: modified_base
<222> LOCATION: (2)
<223> OTHER INFORMATION: u = um
<220> FEATURE:
<221> NAME/KEY: modified_base
<222> LOCATION: (5)
<223> OTHER INFORMATION: u = um
<220> FEATURE:
<221> NAME/KEY: modified_base
<222> LOCATION: (11)
<223> OTHER INFORMATION: u = um
<220> FEATURE:
<221> NAME/KEY: modified_base
<222> LOCATION: (15)
<223> OTHER INFORMATION: u = um
<220> FEATURE:
<221> NAME/KEY: modified_base
<222> LOCATION: (21)
<223> OTHER INFORMATION: u = um

<400> SEQUENCE: 20
gugaucagac ucaauacgaa u                                              21

<210> SEQ ID NO 21
<211> LENGTH: 23
<212> TYPE: RNA
<213> ORGANISM: Artificial Sequence
<220> FEATURE:
<223> OTHER INFORMATION: Description of Artificial Sequence:synthetic
      apolipoprotein B mismatch native (AS) unmodified
      antisense strand siRNA
<220> FEATURE:
<221> NAME/KEY: modified_base
<222> LOCATION: (1)
<223> OTHER INFORMATION: a modified by 5' phosphate

<400> SEQUENCE: 21
auucguauug agucugauca cac                                            23

<210> SEQ ID NO 22
<211> LENGTH: 23
<212> TYPE: RNA
<213> ORGANISM: Artificial Sequence
<220> FEATURE:
<223> OTHER INFORMATION: Description of Artificial Sequence:synthetic
      apolipoprotein B mismatch 2'-O-methyl modified
      2'OMe GU(AS) antisense strand siRNA
<220> FEATURE:
<221> NAME/KEY: modified_base
<222> LOCATION: (1)
<223> OTHER INFORMATION: a modified by 5' phosphate
<220> FEATURE:
<221> NAME/KEY: modified_base
<222> LOCATION: (12)
<223> OTHER INFORMATION: g = gm
<220> FEATURE:
<221> NAME/KEY: modified_base
<222> LOCATION: (13)
<223> OTHER INFORMATION: u = um
<220> FEATURE:
<221> NAME/KEY: modified_base
<222> LOCATION: (14)
<223> OTHER INFORMATION: c = cm
<220> FEATURE:
<221> NAME/KEY: modified_base
```

```
<222> LOCATION: (15)
<223> OTHER INFORMATION: u = um
<220> FEATURE:
<221> NAME/KEY: modified_base
<222> LOCATION: (16)
<223> OTHER INFORMATION: g = gm

<400> SEQUENCE: 22
auucguauug agucugauca cac                                               23

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      synthetic viral FADD-like interleukin-1-beta-converting
      enzyme [FLICE/caspase 8]-inhibitory protein
      (vFLIP) unmodified native (S) sense strand siRNA
<220> FEATURE:
<223> OTHER INFORMATION: Description of Artificial Sequence:synthetic
      viral FADD-like interleukin-1-beta-converting enzyme
      [FLICE/caspase 8]-inhibitory protein (vFLIP)
      unmodified native (S) sense strand siRNA

<400> SEQUENCE: 23
gugguauugu uccuccuaat t                                                 21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      synthetic viral FADD-like interleukin-1-beta-converting enzyme
      [FLICE/caspase 8]-inhibitory protein (vFLIP)
      2'-O-methyl modified 2'OMe GU(S) sense strand siRNA
<220> FEATURE:
<223> OTHER INFORMATION: Description of Artificial Sequence:synthetic
      viral FADD-like interleukin-1-beta-converting enzyme
      [FLICE/caspase 8]-inhibitory protein (vFLIP)
      2'-O-methyl modified 2'OMe GU(S) sense strand siRNA
<220> FEATURE:
<221> NAME/KEY: modified_base
<222> LOCATION: (1)
<223> OTHER INFORMATION: g = gm
<220> FEATURE:
<221> NAME/KEY: modified_base
<222> LOCATION: (2)
<223> OTHER INFORMATION: u = um
<220> FEATURE:
<221> NAME/KEY: modified_base
<222> LOCATION: (3)..(4)
<223> OTHER INFORMATION: g = gm
<220> FEATURE:
<221> NAME/KEY: modified_base
<222> LOCATION: (5)
<223> OTHER INFORMATION: u = um
<220> FEATURE:
<221> NAME/KEY: modified_base
<222> LOCATION: (7)..(8)
<223> OTHER INFORMATION: u = um
<220> FEATURE:
<221> NAME/KEY: modified_base
<222> LOCATION: (9)
<223> OTHER INFORMATION: g = gm
<220> FEATURE:
<221> NAME/KEY: modified_base
<222> LOCATION: (10)..(11)
<223> OTHER INFORMATION: u = um

<400> SEQUENCE: 24
gugguauugu uccuccuaat t                                                 21
```

```
<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      synthetic viral FADD-like interleukin-1-beta-converting
      enzyme [FLICE/caspase 8]-inhibitory protein (vFLIP)
      2'-O-methyl modified 2'OMe U(S) sense strand siRNA
<220> FEATURE:
<223> OTHER INFORMATION: Description of Artificial Sequence:synthetic
      viral FADD-like interleukin-1-beta-converting enzyme
      [FLICE/caspase 8]-inhibitory protein (vFLIP)
      2'-O-methyl modified 2'OMe U(S) sense strand siRNA
<220> FEATURE:
<221> NAME/KEY: modified_base
<222> LOCATION: (2)
<223> OTHER INFORMATION: u = um
<220> FEATURE:
<221> NAME/KEY: modified_base
<222> LOCATION: (5)
<223> OTHER INFORMATION: u = um
<220> FEATURE:
<221> NAME/KEY: modified_base
<222> LOCATION: (7)..(8)
<223> OTHER INFORMATION: u = um
<220> FEATURE:
<221> NAME/KEY: modified_base
<222> LOCATION: (10)..(11)
<223> OTHER INFORMATION: u = um
<220> FEATURE:
<221> NAME/KEY: modified_base
<222> LOCATION: (14)
<223> OTHER INFORMATION: u = um
<220> FEATURE:
<221> NAME/KEY: modified_base
<222> LOCATION: (17)
<223> OTHER INFORMATION: u = um

<400> SEQUENCE: 25
gugguauugu uccuccuaat t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      synthetic viral FADD-like interleukin-1-beta-converting
      enzyme [FLICE/caspase 8]-inhibitory protein
      (vFLIP) unmodified native (AS) antisense strand siRNA
<220> FEATURE:
<223> OTHER INFORMATION: Description of Artificial Sequence:synthetic
      viral FADD-like interleukin-1-beta-converting enzyme
      [FLICE/caspase 8]-inhibitory protein (vFLIP)
      unmodified native (AS) antisense strand siRNA
<220> FEATURE:
<221> NAME/KEY: modified_base
<222> LOCATION: (1)
<223> OTHER INFORMATION: u modified by 5' phosphate

<400> SEQUENCE: 26
uuaggaggaa caauaccact t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      synthetic viral FADD-like interleukin-1-beta-converting
      enzyme [FLICE/caspase 8]-inhibitory protein (vFLIP)
      2'-O-methyl modified 2'OMe U(AS) antisense strand siRNA
<220> FEATURE:
<223> OTHER INFORMATION: Description of Artificial Sequence:synthetic
      viral FADD-like interleukin-1-beta-converting enzyme
```

```
        [FLICE/caspase 8]-inhibitory protein (vFLIP)
        2'-O-methyl modified 2'OMe U(AS) antisense strand siRNA
<220> FEATURE:
<221> NAME/KEY: modified_base
<222> LOCATION: (1)
<223> OTHER INFORMATION: u = um modified by 5' phosphate
<220> FEATURE:
<221> NAME/KEY: modified_base
<222> LOCATION: (2)
<223> OTHER INFORMATION: u = um
<220> FEATURE:
<221> NAME/KEY: modified_base
<222> LOCATION: (14)
<223> OTHER INFORMATION: u = um

<400> SEQUENCE: 27
uuaggaggaa caauaccact t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
        synthetic viral FADD-like interleukin-1-beta-converting
        enzyme [FLICE/caspase 8]-inhibitory protein (vFLIP)
        2'-O-methyl modified 2'OMe C(AS) antisense strand siRNA
<220> FEATURE:
<223> OTHER INFORMATION: Description of Artificial Sequence:synthetic
        viral FADD-like interleukin-1-beta-converting enzyme
        [FLICE/caspase 8]-inhibitory protein (vFLIP)
        2'-O-methyl modified 2'OMe C(AS) antisense strand siRNA
<220> FEATURE:
<221> NAME/KEY: modified_base
<222> LOCATION: (1)
<223> OTHER INFORMATION: u modified by 5' phosphate
<220> FEATURE:
<221> NAME/KEY: modified_base
<222> LOCATION: (11)
<223> OTHER INFORMATION: c = cm
<220> FEATURE:
<221> NAME/KEY: modified_base
<222> LOCATION: (16)..(17)
<223> OTHER INFORMATION: c = cm
<220> FEATURE:
<221> NAME/KEY: modified_base
<222> LOCATION: (19)
<223> OTHER INFORMATION: c = cm

<400> SEQUENCE: 28
uuaggaggaa caauaccact t                                              21
```

MODIFIED SIRNA MOLECULES AND USES THEREOF

CROSS-REFERENCES TO RELATED APPLICATIONS

The present application claims the benefit of U.S. Provisional Application No. 60/812,147, filed Jun. 9, 2006, the disclosure of which is herein incorporated by reference in its entirety for all purposes.

BACKGROUND OF THE INVENTION

Short interfering RNAs (siRNAs) (also known as short interfering nucleic acid (siNA) molecules) that mediate sequence-specific gene silencing through RNA interference (RNAi) are widely used research tools that have potentially broad therapeutic applications (Dorsett et al, *Nature Reviews*, 3:318-329 (2004); Soutschek et al., *Nature*, 432:173-178 (2004)). siRNAs mediate gene silencing through their incorporation into RISC, a component of the RNAi machinery, that initiates the site specific cleavage of homologous mRNA (Dorsett et al., supra). siRNAs can be generated from expression vectors producing short hairpin RNAs that are subsequently processed to form duplex siRNA. Alternatively, siRNAs can be manufactured chemically. Synthetic siRNAs offer a number of advantages, since they permit chemical modifications designed to improve critical parameters such as nuclease stability and pharmacokinetic behavior.

The mammalian innate immune system has evolved mechanisms for recognizing a number of nucleic acid species that are signatures of potential pathogens. Toll-like Receptors (TLRs) (Takeda et al, *Ann. Rev. Immunol.*, 21:335-76 (2003)) have been identified that recognize dsRNA (TLR3) (Alexopoulou et al., *Nature*, 413:732-738 (2001)), ssRNA (TLR7 and TLR8) (Heil et al., *Science*, 303:1526-29 (2004); Diebold et al., *Science*, 303:1529-31 (2004); Lund et al., *Proc. Natl. Acad. Sci. U.S.A.*, 101:5598-5603 (2004)), and CpG DNA (TLR9) (Krieg, *Annu. Rev. Immunol.*, 20:709-760 (2002)) in humans and mice. Common features of these nucleic acid sensing TLRs is their intracellular localization and the induction of Type I interferons such as IFN-α upon stimulation. Activation of the innate immune system causes the rapid production of pro-inflammatory cytokines together with Type I and Type II interferons that orchestrate the developing immune response. This reaction can be associated with acute symptoms of toxicity and inflammation that in severe cases can develop into systemic toxic-shock like syndromes. Unless anticipated and well understood, these phenomena have the potential to limit the utility of siRNA-based therapeutics.

While it has been recently reported that naked, unformulated siRNA is incapable of eliciting an interferon response in mice (Heidel et al., *Nat. Biotechnol.*, 22:1579-1582 (2004)), the pharmacokinetic behavior of such molecules is poor and may limit exposure to critical cell types in vivo. The poor pharmacokinetic properties of naked, unformulated siRNA are likely associated with nuclease degradation and rapid renal clearance. The administration of siRNA combined with delivery vehicles will likely increase the exposure of innate immune cells to siRNA and therefore enhance their potential to stimulate an immune response. In fact, synthetic siRNA, when associated with either lipidic or non-lipidic delivery systems, can activate potent interferon and inflammatory cytokine responses in human blood in vitro or when administered to mice (Judge et al, *Nat. Biotechnol.*, 23:457-462 (2005)). This activity is dependent on the sequence of the siRNA duplex and likely involves the engagement of TLR7 (Judge et al., supra; Hornung et al., *Nat. Med.*, 11:263-270 (2005)).

Thus, there is a strong need in the art for siRNA molecules that abrogate the immunostimulatory activity of siRNA without having a negative impact on RNAi activity. The present invention addresses this and other needs.

BRIEF SUMMARY OF THE INVENTION

The present invention provides chemically modified siRNA molecules and methods of using such siRNA molecules to silence target gene expression.

The present invention is based, in part, upon the surprising discovery that chemical modification of synthetic siRNA can reduce or completely abrogate the interferon and inflammatory cytokine inducing properties and corresponding toxicities of otherwise highly immunostimulatory sequences. As a result, the present invention enables the development of synthetic siRNA molecules that are both potent mediators of RNA interference and safe when administered as drugs.

In one aspect, the present invention provides a chemically synthesized double stranded siNA molecule (i.e., siRNA) that directs cleavage of a target RNA via RNAi, wherein:

(a) each strand of the siNA molecule is about 18 to about 38 nucleotides in length;
(b) one strand of the siNA molecule comprises a nucleotide sequence having sufficient complementarity to the target RNA for the siNA molecule to direct cleavage of the target RNA via RNA interference; and
(c) wherein one or more nucleotides of the siNA molecule are chemically modified to reduce the immunostimulatory properties of the siNA molecule to a level below that of a corresponding siNA molecule having unmodified nucleotides.

In certain instances, the siNA molecule comprises no ribonucleotides. Alternatively, the siNA molecule comprises one or more ribonucleotides.

In some embodiments, one strand of the double-stranded siNA molecule comprises a nucleotide sequence that is complementary to a nucleotide sequence of a target gene or a portion thereof, and a second strand of the double-stranded siNA molecule comprises a nucleotide sequence substantially similar to the nucleotide sequence or a portion thereof of the target RNA. Typically, each strand comprises at least about 18 nucleotides that are complementary to the nucleotides of the other strand.

For example, the siNA molecule can comprise an antisense region comprising a nucleotide sequence that is complementary to a nucleotide sequence of a target gene or a portion thereof, and the siNA can further comprise a sense region, wherein the sense region comprises a nucleotide sequence substantially similar to the nucleotide sequence of the target gene or a portion thereof. Alternatively, the siNA molecule can comprise a sense region and an antisense region, wherein the antisense region comprises a nucleotide sequence that is complementary to a nucleotide sequence of RNA encoded by a target gene, or a portion thereof, and the sense region comprises a nucleotide sequence that is complementary to the antisense region. Preferably, the antisense region and the sense region comprise about 18 to about 38 nucleotides, and the antisense region comprises at least about 18 nucleotides that are complementary to nucleotides of the sense region.

In certain instances, the siNA molecule is assembled from two separate oligonucleotide fragments, wherein one fragment comprises the sense region and a second fragment comprises the antisense region of the siNA molecule. In certain other instances, the sense region is connected to the antisense region via a linker molecule. Examples of linker molecules include, but are not limited to, a polynucleotide linker and a non-nucleotide linker.

Any modified nucleotide known in the art is suitable for use in the present invention. For example, the pyrimidine nucleotides in the sense region can comprise 2'-O-methylpyrimidine nucleotides and/or 2'-deoxy-2'-fluoro pyrimidine nucleotides. Similarly, the pyrimidine nucleotides in the antisense region can comprise 2'-deoxy-2'-fluoro pyrimidine nucleotides. The purine nucleotides in the sense region can comprise 2'-deoxy purine nucleotides. Likewise, the purine nucleotides in the antisense region can comprise 2'-O-methyl purine nucleotides and/or 2'-deoxy-purine nucleotides.

In some embodiments, the fragment comprising the sense region includes a terminal cap moiety at a 5'-end, a 3'-end, or both of the 5' and 3' ends of the fragment comprising the sense region. A non-limiting example of a terminal cap moiety is an inverted deoxy abasic moiety. In other embodiments, the fragment comprising the antisense region optionally includes a phosphate group at the 5'-end of the fragment comprising the antisense region. The antisense region can also comprise a phosphorothioate internucleotide linkage and/or a glyceryl modification at the 3' end of the antisense region.

In further embodiments, each of the two fragments of the siNA molecule comprise about 21 nucleotides. In certain instances, about 19 nucleotides of each fragment of the siNA molecule are base-paired to the complementary nucleotides of the other fragment of the siNA molecule, and at least two 3' terminal nucleotides of each fragment of the siNA molecule are not base-paired to the nucleotides of the other fragment of the siNA molecule. As a non-limiting example, each of the two 3' terminal nucleotides of each fragment of the siNA molecule can comprise 2'-deoxy-pyrimidines. Preferably, the 2'-deoxy-pyrimidine is 2'-deoxy-thymidine. In these instances, about 19 nucleotides of the antisense region are base-paired to the nucleotide sequence of the RNA encoded by a target gene or a portion thereof. Alternatively, all of the about 21 nucleotides of each fragment of the siNA molecule are base-paired to the complementary nucleotides of the other fragment of the siNA molecule. In these instances, about 21 nucleotides of the antisense region are base-paired to the nucleotide sequence of the RNA encoded by a target gene or a portion thereof.

In another aspect, the present invention provides a composition comprising the siNA molecule described above in a pharmaceutically acceptable carrier or diluent.

In yet another aspect, the present invention provides a method for generating the siNA molecule described above, comprising:
(a) introducing modified nucleotides in one or more of the nucleotide positions of the siNA molecule, and
(b) assaying the siNA molecule of step (a) under conditions suitable for isolating an siNA molecule having reduced immunostimulatory properties compared to a corresponding siNA molecule having unmodified nucleotides.

In some embodiments, the reduced immunostimulatory properties comprise an abrogated or reduced induction of inflammatory or proinflammatory cytokines in response to the siNA being introduced in a cell, tissue, or organism. Preferably, the cytokine comprises interleukin-6 (IL-6) or tumor necrosis alpha (TNF-α).

In other embodiments, the reduced immunostimulatory properties comprise an abrogated or reduced induction of Toll Like Receptors (TLRs) in response to the siNA being introduced in a cell, tissue, or organism. Preferably, the Toll Like Receptor comprises TLR3, TLR7, TLR8, or TLR9.

In further embodiments, the reduced immunostimulatory properties comprise an abrogated or reduced induction of interferons in response to the siNA being introduced in a cell, tissue, or organism. Preferably, the interferon comprises interferon alpha.

In preferred embodiments of the present invention, minimal 2'-O-methyl (2'OMe) modifications at selective positions within one strand of the siRNA duplex are sufficient to reduce or fully abrogate the immunostimulatory activity of siRNA, irrespective of its sequence. In particular, by restricting chemical modification to the non-targeting sense strand of the siRNA duplex, the immunostimulatory activity of siRNA can be abolished while retaining full RNAi activity. Using apolipoprotein B (apoB) as a non-limiting example of an endogenous gene target, potent gene silencing can be achieved in vivo using the modified siRNA molecules of the present invention without any evidence of cytokine induction, immunotoxicity, or off-target effects associated with immune activation triggered by a corresponding unmodified siRNA sequence. As a result, patients experience the full benefits of siRNA therapy without suffering any of the immunostimulatory side-effects associated with such therapy.

Thus, the present invention additionally provides a modified siRNA molecule comprising a double-stranded sequence of about 15 to about 30 nucleotides in length, wherein less than about 20% of the nucleotides in the siRNA comprise modified nucleotides. The modified siRNA molecule is less immunostimulatory than a corresponding unmodified siRNA sequence and is capable of silencing expression of the target sequence. In one embodiment, the double-stranded sequence comprises a hairpin loop structure. Preferably, the modified siRNA contains at least one 2'OMe purine or pyrimidine nucleotide such as a 2'OMe-guanosine, 2'OMe-uridine, and/or 2'OMe-adenosine nucleotide, but not a 2'OMe-cytosine nucleotide. The modified nucleotides can be present in one strand (i.e., sense or antisense) or both strands of the siRNA. Preferably, the modified nucleotides are present in the sense strand of the siRNA.

In certain instances, the modified siRNA contains less than about 15%, 10%, or 5% modified nucleotides. As a non-limiting example, the modified siRNA can contain as few as two 2'OMe modified nucleotides, representing less than about 5% of the native 2'-OH positions in the siRNA duplex. This minimal degree of chemical modification, when incorporated into highly immunostimulatory siRNA sequences, can completely abrogate siRNA-mediated interferon and inflammatory cytokine induction in vitro and in vivo (see, Example 2).

In some embodiments, the corresponding unmodified siRNA sequence comprises at least one, two, three, or more 5'-GU-3' motifs.

The present invention also provides a pharmaceutical composition comprising a modified siRNA molecule described herein and a pharmaceutically acceptable carrier.

The present invention further provides a modified siRNA comprising a double-stranded sequence of about 15 to about 30 nucleotides in length, wherein at least one nucleotide in the sense strand of the siRNA is a modified nucleotide and no nucleotides in the antisense strand of the siRNA are modified nucleotides. The modified siRNA molecule is less immunostimulatory than a corresponding unmodified siRNA sequence and is capable of silencing expression of the target sequence. In one embodiment, the double-stranded sequence comprises a hairpin loop structure. Preferably, the modified siRNA contains at least one 2'OMe purine or pyrimidine nucleotide such as a 2'OMe-guanosine, 2'OMe-uridine, and/ or 2'OMe-adenosine nucleotide, but not a 2'OMe-cytosine nucleotide.

In certain instances, the modified siRNA contains less than about 20% modified nucleotides in the sense strand. In certain other instances, the modified siRNA contains less than about 15% modified nucleotides in the sense strand. The modified siRNA may also contain less than about 10% or 5% modified nucleotides in the sense strand.

In some embodiments, the corresponding unmodified siRNA sequence comprises at least one, two, three, or more 5'-GU-3' motifs.

The present invention also provides a nucleic acid-lipid particle comprising a modified siRNA molecule described herein, a cationic lipid, and a non-cationic lipid. In certain instances, the nucleic acid-lipid particle further comprises a conjugated lipid that inhibits aggregation of particles. Preferably, the nucleic acid-lipid particle comprises a modified siRNA molecule described herein, a cationic lipid, a non-cationic lipid, and a conjugated lipid that inhibits aggregation of particles.

The cationic lipid may be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), or a mixture thereof. The cationic lipid may comprise from about 20 mol % to about 50 mol % or about 40 mol % of the total lipid present in the particle.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may comprise from about 5 mol % to about 90 mol % or about 40 to about 60 mol % of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles may be from 0 mol % to about 20 mol % or about 2 mol % of the total lipid present in the particle.

In some embodiments, the nucleic acid-lipid particle further comprises cholesterol at, e.g., about 10 mol % to about 60 mol % or about 48 mol % of the total lipid present in the particle.

In certain instances, the modified siRNA is fully encapsulated in the nucleic acid-lipid particle. In certain other instances, the modified siRNA is complexed to the lipid portion of the particle.

The present invention further provides a pharmaceutical composition comprising the nucleic acid-lipid particle and a pharmaceutically acceptable carrier.

The modified siRNA molecules described herein can be used in methods for silencing expression of a target sequence. As a non-limiting example, an effective amount of the modified siRNA can be administered to a mammalian subject, thereby silencing expression of a target sequence. Preferably, the mammalian subject is a human. In certain instances, the modified siRNA is in a nucleic acid-lipid particle comprising the siRNA molecule, a cationic lipid, and a non-cationic lipid. In certain other instances, the modified siRNA is in a nucleic acid-lipid particle comprising the siRNA molecule, a cationic lipid, a non-cationic lipid, and a conjugated lipid that inhibits aggregation of particles.

The present invention also provides a method of modifying an siRNA having immunostimulatory properties. The method comprises: (a) providing an unmodified siRNA sequence capable of silencing expression of a target sequence and comprising a double stranded sequence of about 15 to about 30 nucleotides in length; and (b) modifying the siRNA by substituting at least one nucleotide in the sense strand with a modified nucleotide, thereby generating a modified siRNA that is less immunostimulatory than the unmodified siRNA sequence and is capable of silencing expression of the target sequence. Preferably, the modified siRNA contains at least one 2'OMe purine or pyrimidine nucleotide such as a 2'OMe-guanosine, 2'OMe-uridine, and/or 2'OMe-adenosine nucleotide, but not a 2'OMe-cytosine nucleotide.

In certain instances, the sense strand of the unmodified siRNA comprises at least one, two, three, or more 5'-GU-3' motifs. Preferably, at least one nucleotide in the 5'-GU-3' motif is substituted with a modified nucleotide. For example, both nucleotides in the 5'-GU-3' motif can be substituted with modified nucleotides.

The present invention also provides a method of identifying and modifying an siRNA having immunostimulatory properties. The method comprises: (a) contacting an unmodified siRNA sequence with a mammalian responder cell under conditions suitable for the responder cell to produce a detectable immune response; (b) identifying the unmodified siRNA sequence as an immunostimulatory siRNA by the presence of a detectable immune response in the responder cell; and (c) modifying the immunostimulatory siRNA by substituting at least one nucleotide with a modified nucleotide, thereby generating a modified siRNA sequence that is less immunostimulatory than the unmodified siRNA sequence.

In a preferred embodiment, the modified siRNA contains at least one 2'OMe purine or pyrimidine nucleotide such as a 2'OMe-guanosine, 2'OMe-uridine, and/or 2'OMe-adenosine nucleotide, but not a 2'OMe-cytosine nucleotide. In certain instances, the unmodified siRNA sequence comprises a 5'-GU-3' motif and at least one nucleotide in the 5'-GU-3' motif is substituted with a modified nucleotide. In one embodiment, the mammalian responder cell is a peripheral blood mononuclear cell (PBMC). In another embodiment, the detectable immune response comprises production of a cytokine or growth factor such as, for example, TNF-α, TNF-β, IFN-α, IFN-γ, IL-6, IL-12, or a combination thereof.

The present invention additionally provides isolated nucleic acid molecules comprising a modified sequence set forth in Table 2. The modified sequence can further include its complementary strand, thereby generating a modified siRNA duplex.

Other features, objects, and advantages of the invention and its preferred embodiments will become apparent from the detailed description, examples, and claims that follow.

DETAILED DESCRIPTION OF THE INVENTION

I. Definitions

Figure 1A:
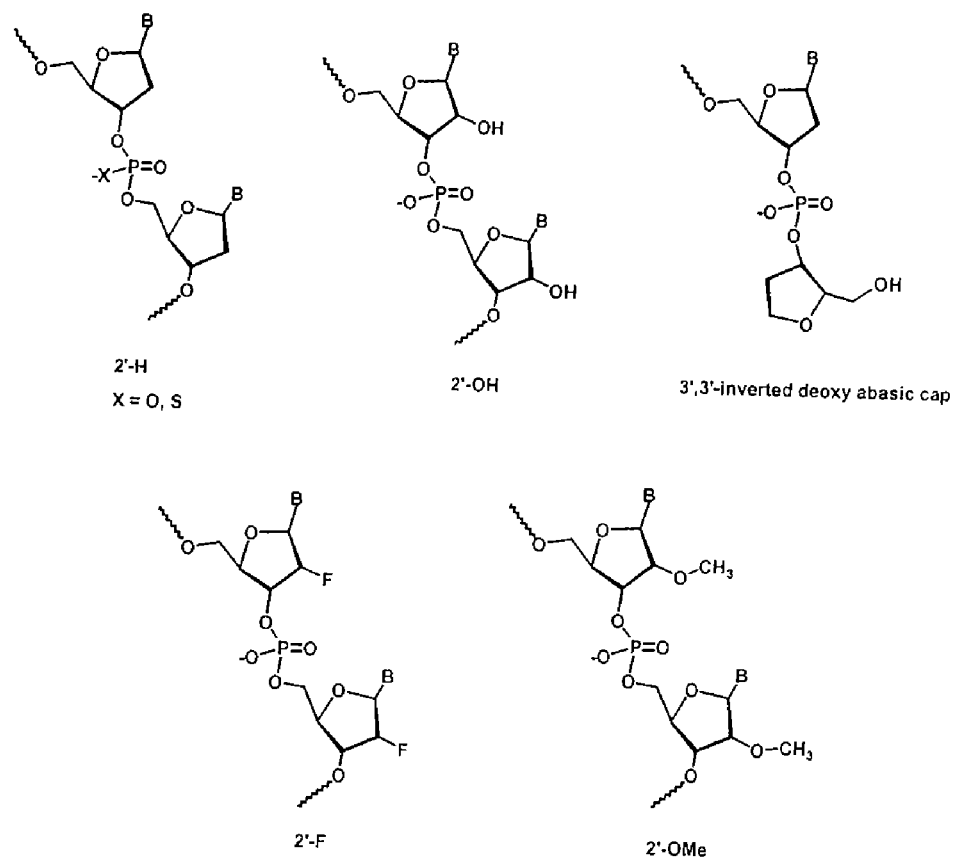
FIG. 1 illustrates the structure of 2' ribose modifications and termini and data demonstrating that chemically modified siRNA are active in mediating RNAi. (a) siRNAs were prepared incorporating nucleotide analogues modified at the 2' ribose position (Table 1). Purine nucleotides were modified by incorporation of 2'OMe or 2'-H. Pyrimidine nucleotides were modified by incorporation of 2'-F. (b) Neuro2a Luc cells stably transfected to express luciferase under the control of the CMV promoter were treated for 48 hours with lipid complexed luciferase siRNA or non-targeting GFP control siRNA. Luciferase activity was assayed in cell lysates and expressed as percent of GFP siRNA treated control cultures. Values represent mean+/−SD of triplicate cultures.

As used herein, the following terms have the meanings ascribed to them unless specified otherwise.

The term "interfering RNA" or "RNAi" or "interfering RNA sequence" refers to double-stranded RNA (i.e., duplex RNA) that is capable of reducing or inhibiting expression of a target gene (i.e., by mediating the degradation of mRNAs which are complementary to the sequence of the interfering RNA) when the interfering RNA is in the same cell as the target gene. Interfering RNA thus refers to the double stranded RNA formed by two complementary strands or by a single, self-complementary strand. Interfering RNA may have substantial or complete identity to the target gene or may comprise a region of mismatch (i.e., a mismatch motif). The sequence of the interfering RNA can correspond to the full length target gene, or a subsequence thereof.

Interfering RNA includes "short interfering RNA," "siRNA," "short interfering nucleic acid," or "siNA," e.g., interfering RNA of about 15-60, 15-50, or 15-40 (duplex) nucleotides in length, more typically about, 15-30, 15-25 or 19-25 (duplex) nucleotides in length, and is preferably about 20-24, 21-22, or 21-23 (duplex) nucleotides in length (e.g., each complementary sequence of the double stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 20-24, 21-22, or 21-23 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate oligonucleotides, wherein one strand is the sense strand and the other is the complementary antisense strand; a double-stranded polynucleotide molecule assembled from a single oligonucleotide, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule.

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *PNAS USA* 99: 9942-9947 (2002); Calegari et al., *PNAS USA* 99: 14236 (2002); Byrom et al., *Ambion TechNotes* 10(1): 4-6 (2003); Kawasaki et al., *Nucleic Acids Res.* 31: 981-987 (2003); Knight and Bass, *Science* 293: 2269-2271 (2001); and Robertson et al, *J. Biol. Chem.* 243: 82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an siRNA sequence that does not have 100% complementarity to its target sequence. An siRNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

An "effective amount" or "therapeutically effective amount" of an siRNA is an amount sufficient to produce the desired effect, e.g., an inhibition of expression of a target sequence in comparison to the normal expression level detected in the absence of the siRNA. Inhibition of expression of a target gene or target sequence is achieved when the value obtained with the siRNA relative to the control is about 90%, 80%, 70%, 60%, 50%, 40%, 30%, 25%, 20%, 15%, 10%, 5%, or 0%. Suitable assays for measuring expression of a target gene or target sequence include, e.g. examination of protein or mRNA levels using techniques known to those of skill in the art such as dot blots, northern blots, in situ hybridization, ELISA, immunoprecipitation, enzyme function, as well as phenotypic assays known to those of skill in the art.

As used herein, the term "responder cell" refers to a cell, preferable a mammalian cell, that produces a detectable immune response when contacted with an immunostimulatory siRNA. Exemplary responder cells include, e.g., dendritic cells, macrophages, peripheral blood mononuclear cells (PBMC), splenocytes, and the like. Detectable immune responses include, e.g., production of cytokines or growth factors such as TNF-α, TNF-β, IFN-α, IFN-γ, IL-1, IL-2, IL-3, IL-4, IL-5, IL-6, IL-10, IL-12, IL-13, TGF, and combinations thereof.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which an siRNA will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, Ausubel et al, eds.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 20 to about 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman, *Adv. Appl Math.* 2:482 (1981), by the homology alignment algorithm of Needleman and Wunsch, *J. Mol. Biol.* 48:443 (1970), by the search for similarity method of Pearson and Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

A preferred example of algorithms that are suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information.

The BLAST algorithm also performs a statistical analysis of the similarity between two sequences (see, e.g., Karlin and Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" or "polynucleotide" refers to a polymer containing at least two deoxyribonucleotides or ribonucleotides in either single- or double-stranded form and include DNA and RNA. DNA may be in the form of, e.g., antisense oligonucleotides, plasmid DNA, pre-condensed DNA, a PCR product, vectors (P1, PAC, BAC, YAC, artificial chromosomes), expression cassettes, chimeric sequences, chromosomal DNA, or derivatives and combinations of these groups. RNA may be in the form of siRNA, mRNA, tRNA, rRNA, tRNA, vRNA, and combinations thereof. Nucleic acids include nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260.2605-2608 (1985); Rossolini et al., *Mol. Cell. Probes* 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

"Lipid vesicle" refers to any lipid composition that can be used to deliver a compound such as an siRNA including, but not limited to, liposomes, wherein an aqueous volume is encapsulated by an amphipathic lipid bilayer; or wherein the lipids coat an interior comprising a large molecular component, such as a plasmid comprising an interfering RNA sequence, with a reduced aqueous interior; or lipid aggregates or micelles, wherein the encapsulated component is contained within a relatively disordered lipid mixture. The term lipid vesicle encompasses any of a variety of lipid-based carrier systems including, without limitation, SPLPs, pSPLPs, SNALPs, liposomes, micelles, virosomes, lipid-nucleic acid particles, nucleic acid complexes, and mixtures thereof.

As used herein, "lipid encapsulated" can refer to a lipid formulation that provides a compound such as an siRNA with full encapsulation, partial encapsulation, or both. In a preferred embodiment, the nucleic acid is fully encapsulated in the lipid formulation (e.g., to form an SPLP, pSPLP, SNALP, or other nucleic acid-lipid particle).

As used herein, the term "SNALP" refers to a stable nucleic acid-lipid particle, including SPLP. A SNALP represents a vesicle of lipids coating a reduced aqueous interior comprising a nucleic acid (e.g., siRNA, ssDNA, dsDNA, ssRNA, micro RNA (miRNA), short hairpin RNA (shRNA), dsRNA, or a plasmid, including plasmids from which an interfering RNA is transcribed). As used herein, the term "SPLP" refers to a nucleic acid-lipid particle comprising a nucleic acid (e.g., a plasmid) encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection, accumulate at distal sites (e.g., sites physically separated from the administration site) and can mediate expression of the transfected gene at these distal sites. SPLPs include "pSPLP," which comprise an encapsulated condensing agent-nucleic acid complex as set forth in PCT Patent Publication No. WO 00/03683.

The nucleic acid-lipid particles of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and WO 96/40964.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle-adopting lipid" is intended to include any amphipathic lipid that is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane. Vesicle-adopting lipids include lipids that on their own tend to adopt a nonlamellar phase, yet which are capable of assuming a bilayer structure in the presence of a bilayer-stabilizing component. A typical example is dioleoylphosphatidylethanolamine (DOPE). Bilayer stabilizing components include, but are not limited to, conjugated lipids that inhibit aggregation of nucleic acid-lipid particles, polyamide oligomers (e.g., ATTA-lipid derivatives), peptides, proteins, detergents, lipid-derivatives, PEG-lipid derivatives such as PEG coupled to dialkyloxypropyls, PEG coupled to diacylglycerols, PEG coupled to phosphatidyl-ethanolamines, PEG conjugated to ceramides (see, e.g., U.S. Pat. No. 5,885,613), cationic PEG lipids, and mixtures thereof. PEG can be conjugated directly to the lipid or may be linked to the lipid via a linker moiety. Any linker moiety suitable for coupling the PEG to a lipid can be used including, e.g., non-ester containing linker moieties and ester-containing linker moieties.

The term "amphipathic lipid" refers, in part, to any suitable material wherein the hydrophobic portion of the lipid material orients into a hydrophobic phase, while the hydrophilic portion orients toward the aqueous phase. Amphipathic lipids are usually the major component of a lipid vesicle. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any neutral lipid as described above as well as anionic lipids.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH. It has been surprisingly found that cationic lipids comprising alkyl chains with multiple sites of unsaturation, e.g., at least two or three sites of unsaturation, are particularly useful for forming nucleic acid-lipid particles with increased membrane fluidity. A number of cationic lipids and related analogs, which are also useful in the present invention, have been described in co-pending U.S. Patent Application Nos. 60/578,075 and 60/610,746; U.S. Pat. Nos. 5,208,036; 5,264,618; 5,279,833; 5,283,185; 5,753,613; and 5,785,992; and WO 96/10390. Examples of cationic lipids include, but are not limited to, N,N-dioleyl-N,N-dimethylammonium chloride (DODAC), dioctadecyldimethylammonium (DODMA), distearyldimethylammonium (DSDMA), N-(2,3-dioleyloxy)propyl)-N,N,N-trimethylammonium chloride (DOTMA), N,N-distearyl-N,N-dimethylammonium bromide (DDAB), N-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 1,2-DiLinoleyloxy-N,N-dimethylaminopropane (DLinDMA), 1,2-Dilinolenyloxy-N,N-dimethylaminopropane (DLenDMA), and mixtures thereof. In some cases, the cationic lipids comprise a protonatable tertiary amine head group, C18 alkyl chains, ether linkages between the head group and alkyl chains, and 0 to 3 double bonds. Such lipids include, e.g., DSDMA, DLinDMA, DLenDMA, and DODMA. The cationic lipids may also comprise ether linkages and pH titratable head groups. Such lipids include, e.g., DODMA.

The term "hydrophobic lipid" refers to compounds having apolar groups that include, but are not limited to, long chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "fusogenic" refers to the ability of a liposome, an SNALP, or other drug delivery system to fuse with membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery that leads to a broad biodistribution of a compound such as an siRNA within an organism. Some techniques of administration can lead to the systemic delivery of certain compounds, but not others. Systemic delivery means that a useful, preferably therapeutic, amount of a compound is exposed to most parts of the body. To obtain broad biodistribution generally requires a blood lifetime such that the compound is not rapidly degraded or cleared (such as by first pass organs (liver, lung, etc.) or by rapid, nonspecific cell binding) before reaching a disease site distal to the site of administration. Systemic delivery of nucleic acid-lipid particles can be by any means known in the art including, for example, intravenous, subcutaneous, and intraperitoneal. In a preferred embodiment, systemic delivery of nucleic acid-lipid particles is by intravenous delivery.

"Local delivery," as used herein, refers to delivery of a compound such as an siRNA directly to a target site within an organism. For example, a compound can be locally delivered by direct injection into a disease site such as a tumor or other target site such as a site of inflammation or a target organ such as the liver, heart, pancreas, kidney, and the like.

The term "mammal" refers to any mammalian species such as a human, mouse, rat, dog, cat, hamster, guinea pig, livestock, and the like. Preferably, the mammal is a human.

II. General Overview

Targeted silencing of disease-associated genes by synthetic siRNA holds considerable promise as a novel therapeutic strategy. However, unmodified siRNA can be immunostimulatory, e.g., stimulate potent inflammatory responses from innate immune cells, particularly when associated with delivery vehicles that facilitate intracellular uptake. This represents a significant barrier to the therapeutic development of siRNA due to toxicity and off-target gene effects associated with the inflammatory response. The present invention overcomes these limitations by chemical modification of synthetic siRNA that results in a reduction or complete abrogation of the interferon and inflammatory cytokine inducing properties and corresponding toxicities of otherwise highly immunostimulatory sequences. As such, chemical modification of immunostimulatory siRNA according to the methods of the present invention enables the development of synthetic siRNA molecules that are both potent mediators of RNA interference and safe when administered as therapeutic agents.

The present invention also illustrates that selective incorporation of modified nucleotides such as 2'-O-methyl (2'OMe) uridine and/or guanosine nucleotides into either strand of the siRNA duplex can reduce or completely abrogate the immune response to synthetic siRNA. In particular, by selective 2'OMe modifications within the sense strand, non-immunostimulatory siRNA can be readily generated that retain full gene silencing activity. As a non-limiting example, 2'OMe modified siRNA targeting apolipoprotein B (apoB) can mediate potent silencing of its target mRNA when encapsulated within an effective systemic delivery vehicle such as a nucleic acid-lipid particle, causing significant decreases in serum apoB and cholesterol. This is achieved at therapeutically viable siRNA doses without cytokine induction, toxicity, and off-target effects associated with the use of unmodified siRNA. Advantageously, the approach to siRNA design and delivery described herein is widely applicable and advances synthetic siRNA into a broad range of therapeutic areas.

Thus, the present invention provides chemically modified siRNA molecules and methods of using such siRNA molecules to silence target gene expression. The present invention also provides nucleic acid-lipid particles comprising a modified siRNA molecule described herein, a cationic lipid, and a non-cationic lipid, which can further comprise a conjugated lipid that inhibits aggregation of particles. Methods for identifying and/or modifying an siRNA having immunostimulatory properties are also provided.

III. siRNAs

The siRNA molecules of the present invention are capable of silencing expression of a target sequence, and are about 18 to about 38 nucleotides in length. In some embodiments the siRNA molecules of the invention are about 15 to 30 nucleotides in length, and, in some preferred embodiments, comprise less than about 20% modified nucleotides. Importantly, the modified siRNA is less immunostimulatory than a corresponding unmodified siRNA sequence and retains full RNAi activity against the target sequence. Preferably, the modified siRNA contains at least one 2'OMe purine or pyrimidine nucleotide such as a 2'OMe-guanosine, 2'OMe-uridine, and/or 2'OMe-adenosine nucleotide, but not a 2'OMe-cytosine nucleotide. The modified nucleotides can be present in one strand (i.e., sense or antisense) or both strands of the siRNA. Preferably, the modified nucleotides are present in the sense strand of the siRNA. The siRNA sequences may have overhangs (e.g., 3' or 5' overhangs as described in Elbashir et al., Genes Dev., 15:188 (2001) or Nykanen et al., Cell, 107:309 (2001), or may lack overhangs (i.e., have blunt ends).

According to the methods of the present invention, siRNA which are immunostimulatory can be modified to decrease their immunostimulatory properties without having a negative impact on RNAi activity. For example, an immunostimulatory siRNA can be modified by replacing one or more nucleotides in the sense strand with a modified nucleotide, thereby generating a modified siRNA with reduced immunostimulatory properties that is still capable of silencing expression of the target sequence. Preferably, the modified nucleotide is a 2'OMe nucleotide such as a 2'OMe-guanosine, 2'OMe-uridine, and/or 2'OMe-adenosine nucleotide. It is also preferred that the modified siRNA comprises less than about 20% modified nucleotides, e.g., less than about 20%, 19%, 18%, 17%, 16%, 15%, 14%, 13%, 12%, 11%, 10%, 9%, 8%, 7%, 6%, 5%, 4%, 3%, 2%, or 1% modified nucleotides.

A. Selection of siRNA Sequences

Suitable siRNA sequences can be identified using any means known in the art. Typically, the methods described in Elbashir et al., Nature, 411:494-498 (2001) and Elbashir et al., EMBO J., 20:6877-6888 (2001) are combined with rational design rules set forth in Reynolds et al., Nature Biotech., 22(3):326-330 (2004).

Generally, the sequence within about 50 to about 100 nucleotides 3' of the AUG start codon of a transcript from the target gene of interest is scanned for dinucleotide sequences (e.g., AA, CC, GG, or UU) (see, e.g., Elbashir et al., EMBO J., 20:6877-6888 (2001)). The nucleotides immediately 3' to the dinucleotide sequences are identified as potential siRNA target sequences. Typically, the 19, 21, 23, 25, 27, 29, 31, 33, 35, or more nucleotides immediately 3' to the dinucleotide sequences are identified as potential siRNA target sites. In some embodiments, the dinucleotide sequence is an AA sequence and the 19 nucleotides immediately 3' to the AA dinucleotide are identified as a potential siRNA target site. siRNA target sites are usually spaced at different positions along the length of the target gene. To further enhance silencing efficiency of the siRNA sequences, potential siRNA target sites may be further analyzed to identify sites that do not contain regions of homology to other coding sequences. For example, a suitable siRNA target site of about 21 base pairs typically will not have more than 16-17 contiguous base pairs of homology to other coding sequences. If the siRNA sequences are to be expressed from an RNA Pol III promoter, siRNA target sequences lacking more than 4 contiguous A's or T's are selected.

Once the potential siRNA target site has been identified, siRNA sequences complementary to the siRNA target sites may be designed. To enhance their silencing efficiency, the siRNA sequences may also be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features are useful for selection of siRNA.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs can also provide an indication of whether the sequence may be immunostimulatory. Once an siRNA molecule is found to be immunostimulatory, it can then be modified according to the methods described herein to decrease its immunostimulatory properties. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, TNF-β, IFN-α, IFN-γ, IL-6, IL-12, or a combination thereof. An siRNA molecule identified as being immunostimulatory can then be modified to decrease its immunostimulatory properties by replacing less than about 20% of the nucleotides on the sense and/or antisense strand with modified nucleotides such as 2'OMe nucleotides (e.g., 2'OMe-guanosine, 2'OMe-uridine, and/or 2'OMe-adenosine). The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al, in Kirkham and Hunter, eds., Radioimmunoassay Methods, E. and S. Livingstone, Edinburgh (1970)); the "Western blot" method of Gordon et al. (U.S. Pat. No. 4,452,901); immunoprecipitation of labeled ligand (Brown et al., J. Biol. Chem., 255:4980-4983 (1980)); enzyme-linked immunosorbent assays (ELISA) as described, for example, by Raines et al., J. Biol. Chem., 257:5154-5160 (1982); immunocytochemical techniques, including the use of fluorochromes (Brooks et al., Clin. Exp. Immunol., 39:477 (1980)); and neutralization of activity (Bowen-Pope et al., Proc. Natl. Acad. Sci. U.S.A., 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. A non-limiting example of an in vivo model for detecting an immune response includes the in vivo mouse cytokine induction assay described in Example 2 below.

Monoclonal antibodies that specifically bind cytokines and growth factors are commercially available from multiple sources and can be generated using methods known in the art (see, e.g., Kohler and Milstein, *Nature* 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

B. Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. The siRNA sequences may have overhangs (e.g., 3' or 5' overhangs as described in Elbashir et al., *Genes Dev.*, 15:188 (2001) or Nykanen et al., *Cell*, 107:309 (2001), or may lack overhangs (i.e., to have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene*, 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression. A Laboratory Manual* (1990); and *Current Protocols in Molecular Biology* (Ausubel et al., eds., 1994).

Preferably, siRNA are chemically synthesized. The oligonucleotides that comprise the modified siRNA molecules of the present invention can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al, *Nucl. Acids Res.*, 23:2677-2684 (1995); and Wincott et al., *Methods Mol. Bio.*, 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 µmol scale protocol with a 2.5 min. coupling step for 2'-O-methylated nucleotides. Alternatively, syntheses at the 0.2 µmol scale can be performed on a 96-well plate synthesizer from Protogene (Palo Alto, Calif.). However, a larger or smaller scale of synthesis is also within the scope of the present invention. Suitable reagents for oligonucleotide synthesis, methods for RNA deprotection, and methods for RNA purification are known to those of skill in the art.

The modified siRNA molecules of the present invention can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of modified siRNA can be readily adapted to both multiwell/multiplate synthesis platforms as well as large scale synthesis platforms employing batch reactors, synthesis columns, and the like. Alternatively, the modified siRNA molecules of the present invention can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, the modified siRNA molecules of the present invention can be synthesized as a single continuous oligonucleotide fragment, where the self-complementary sense and antisense regions hybridize to form an siRNA duplex having hairpin secondary structure.

C. Modifying siRNA Sequences

In some embodiments, the siRNA molecules of the present invention comprise a duplex having two strands and at least one modified nucleotide, wherein each strand is about 18 to about 38 nucleotides in length. In some preferred embodiments, each strand is about 15 to about 30 nucleotides in length. Advantageously, the modified siRNA is less immunostimulatory than a corresponding unmodified siRNA sequence but retains the capability of silencing the expression of a target sequence. In certain instances, the modified siRNA comprise modified nucleotides as a percentage of the total number of nucleotides present in the siRNA molecule. Preferably, less than about 20%, 15%, 10%, or 5% of the nucleotides in the siRNA are modified nucleotides (e.g., less than about 20%, 19%, 18%, 17%, 16%, 15%, 14%, 13%, 12%, 11%, 10%, 9%, 8%, 7%, 6%, 5%, 4%, 3%, 2%, or 1%). As a non-limiting example, an siRNA having a total of 42 nucleotides in which 2 of the nucleotides (e.g., both in the sense strand, both in the antisense strand, or one in each strand) are 2'-O-methyl ribonucleotides comprises a total of less than 5% modified nucleotides. In certain other instances, the modified siRNA comprises one or more modified nucleotides only in the sense strand of the siRNA. Preferably, less than about 20%, 15%, 10%, or 5% of the nucleotides in the sense strand of the siRNA are modified nucleotides (e.g., less than about 20%, 19%, 18%, 17%, 16%, 15%, 14%, 13%, 12%, 11%, 10%, 9%, 8%, 7%, 6%, 5%, 4%, 3%, 2%, or 1%). As another non-limiting example, an siRNA having a total of 42 nucleotides in which 2 of the nucleotides in the sense strand are 2'-O-methyl ribonucleotides comprises a total of less than 5% modified nucleotides.

Examples of modified nucleotides suitable for use in the present invention include, but are not limited to, ribonucleotides having a 2'-O-methyl (2'OMe), 2'-deoxy-2'-fluoro, 2'-deoxy, 5-C-methyl, 2'-methoxyethyl, 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in the siRNA molecules of the present invention. Such modified nucleotides include, without limitation, locked nucleic acid (LNA) nucleotides (e.g., 2'-O, 4'-C-methylene-(D-ribofuranosyl) nucleotides), 2'-methoxyethoxy (MOE) nucleotides, 2'-methyl-thio-ethyl nucleotides, 2'-deoxy-2'-fluoro nucleotides, 2'-deoxy-2'-chloro nucleotides, and 2'-azido nucleotides. In certain instances, the siRNA molecules of the present invention include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.,* 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.,* 29:2437-2447 (2001)) can be incorporated into the siRNA molecules of the present invention.

In certain embodiments, the siRNA molecules of the present invention further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron,* 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties, in Modern Synthetic Methods,* VCH, 331-417 (1995); Mesmaeker et al., *Novel Backbone Replacements for Oligonucleotides, in Carbohydrate Modifications in Antisense Research,* ACS, 24-39 (1994)). Such chemical modifications can occur at the 5'-end and/or 3'-end of the sense strand, antisense strand, or both strands of the siRNA.

In some embodiments, the sense and/or antisense strand can further comprise a 3'-terminal overhang having about 1 to about 4 (e.g., 1, 2, 3, or 4) 2'-deoxy ribonucleotides and/or any combination of modified and unmodified nucleotides. Additional examples of modified nucleotides and types of chemical modifications that can be introduced into the modified siRNA molecules of the present invention are described, e.g., in UK Patent No. GB 2,397,818 B and U.S. Patent Publication Nos. 20040192626 and 20050282188.

The modified siRNA molecules of the present invention can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the chemically-modified siRNA molecule. The conjugate can be attached at the 5' and/or 3'-end of the sense and/or antisense strand of the chemically-modified siRNA via a covalent attachment such as, e.g., a biodegradable linker. The conjugate can also be attached to the chemically-modified siRNA, e.g., through a carbamate group or other linking group (see, e.g., U.S. Patent Publication Nos. 20050074771, 20050043219, and 20050158727). In certain instances, the conjugate is a molecule that facilitates the delivery of the chemically-modified siRNA into a cell. Examples of conjugate molecules suitable for attachment to the chemically-modified siRNA of the present invention include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the chemically-modified siRNA molecule can be evaluated for improved pharmacokinetic profiles, bioavailability, and/or stability of the siRNA while retaining full RNAi activity. As such, one skilled in the art can screen chemically-modified siRNA molecules having various conjugates attached thereto to identify ones having improved properties and full RNAi activity using any of a variety of well-known in vitro cell culture or in vivo animal models.

D. Target Genes

The siRNA described herein can be used to downregulate or silence the translation (i.e., expression) of a gene of interest. Genes of interest include, but are not limited to, genes associated with viral infection and survival, genes associated with metabolic diseases and disorders (e.g., liver diseases and disorders), genes associated with tumorigenesis and cell transformation, angiogenic genes, immunomodulator genes such as those associated with inflammatory and autoimmune responses, ligand receptor genes, and genes associated with neurodegenerative disorders.

Genes associated with viral infection and survival include those expressed by a virus in order to bind, enter, and replicate in a cell. Of particular interest are viral sequences associated with chronic viral diseases. Viral sequences of particular interest include sequences of Hepatitis viruses (Hamasaki et al., *FEBS Lett.*, 543:51 (2003); Yokota et al., *EMBO Rep.*, 4:602 (2003); Schlomai et al., *Hepatology*, 37:764 (2003); Wilson et al., *Proc. Natl. Acad. Sci.*, 100:2783 (2003); Kapadia et al., *Proc. Natl. Acad. Sci.*, 100:2014 (2003); and FIELDS VIROLOGY (Knipe et al., eds. 2001)); Human Immunodeficiency Virus (HIV) (Banerjea et al., *Mol. Ther.*, 8:62 (2003); Song et al., *J. Virol.*, 77:7174 (2003); Stephenson, *JAAM*, 289:1494 (2003); Qin et al, *Proc. Natl. Acad. Sci.*, 100:183 (2003)); Herpes viruses (Jia et al., *J. Virol.*, 77:3301 (2003)); and Human Papilloma Viruses (HPV) (Hall et al, *J. Virol.*, 77:6066 (2003); Jiang et al., *Oncogene*, 21:6041 (2002)). Exemplary hepatitis viral nucleic acid sequences that can be silenced include, but are not limited to, nucleic acid sequences involved in transcription and translation (e.g., En1, En2, X, P) and nucleic acid sequences encoding structural proteins (e.g., core proteins including C and C-related proteins, capsid and envelope proteins including S, M, and/or L proteins, or fragments thereof) (see, e.g., FIELDS VIROLOGY, 2001, supra). Exemplary Hepatitis C nucleic acid sequences that can be silenced include, but are not limited to, serine proteases (e.g., NS3/NS4), helicases (e.g. NS3), polymerases (e.g., NS5B), and envelope proteins (e.g., E1, E2, and p7). Hepatitis A nucleic acid sequences are set forth in, e.g., Genbank Accession No. NC_001489; Hepatitis B nucleic acid sequences are set forth in, e.g., Genbank Accession No. NC_003977; Hepatitis C nucleic acid sequences are set forth in, e.g., Genbank Accession No. NC_004102; Hepatitis D nucleic acid sequence are set forth in, e.g., Genbank Accession No. NC_001653; Hepatitis E nucleic acid sequences are set forth in, e.g., Genbank Accession No. NC_001434; and Hepatitis G nucleic acid sequences are set forth in, e.g., Genbank Accession No. NC_001710. Silencing of sequences that encode genes associated with viral infection and survival can conveniently be used in combination with the administration of conventional agents used to treat the viral condition.

Genes associated with metabolic diseases and disorders (e.g., disorders in which the liver is the target and liver diseases and disorders) include, for example, genes expressed in dyslipidemia (e.g., liver X receptors such as LXRα and LXRβ (Genback Accession No. NM_007121), farnesoid X receptors (FXR) (Genbank Accession No. NM_005123), sterol-regulatory element binding protein (SREBP), Site-1 protease (SIP), 3-hydroxy-3-methylglutaryl coenzyme-A reductase (HMG coenzyme-A reductase), Apolipoprotein (ApoB), and Apolipoprotein (ApoE)); and diabetes (e.g., Glucose 6-phosphatase) (see, e.g., Forman et al., *Cell*, 81:687 (1995); Seol et al., *Mol. Endocrinol.*, 9:72 (1995), Zavacki et al., *PNAS USA*, 94:7909 (1997); Sakai et al., *Cell*, 85:1037-1046 (1996); Duncan et al., *J. Biol. Chem.*, 272:12778-12785 (1997); Willy et al., *Genes Dev.*, 9:1033-1045 (1995); Lehmann et al., *J. Biol. Chem.*, 272:3137-3140 (1997); Janowski et al., *Nature*, 383:728-731 (1996); and Peet et al., *Cell*, 93:693-704 (1998)). One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder.

Examples of gene sequences associated with tumorigenesis and cell transformation include translocation sequences such as MLL fusion genes, BCR-ABL (Wilda et al., *Oncogene*, 21:5716 (2002); Scherr et al., *Blood*, 101:1566 (2003)), TEL-AML1, EWS-FLI1, TLS-FUS, PAX3-FKHR, BCL-2, AML1-ETO, and AML1-MTG8 (Heidenreich et al., *Blood*, 101:3157 (2003)); overexpressed sequences such as multidrug resistance genes (Nieth et al., *FEBS Lett.*, 545:144 (2003); Wu et al, *Cancer Res.*, 63:1515 (2003)), cyclins (Li et al., *Cancer Res.*, 63:3593 (2003); Zou et al., *Genes Dev.*, 16:2923 (2002)), beta-Catenin (Verma et al., *Clin Cancer Res.*, 9:1291 (2003)), telomerase genes (Kosciolek et al., *Mol Cancer Ther.*, 2:209 (2003)), c-MYC, N-MYC, BCL-2, ERBB1, and ERBB2 (Nagy et al. *Exp. Cell Res.*, 285:39 (2003)); and mutated sequences such as RAS (reviewed in Tuschl and Borkhardt, *Mol. Interventions*, 2:158 (2002)). Silencing of sequences that encode DNA repair enzymes find use in combination with the administration of chemotherapeutic agents (Collis et al., *Cancer Res.*, 63:1550 (2003)). Genes encoding proteins associated with tumor migration are also target sequences of interest, for example, integrins, selectins, and metalloproteinases. The foregoing examples are not exclusive. Any whole or partial gene sequence that facilitates or promotes tumorigenesis or cell transformation, tumor growth, or tumor migration can be included as a template sequence.

Angiogenic genes are able to promote the formation of new vessels. Of particular interest is Vascular Endothelial Growth Factor (VEGF) (Reich et al., *Mol. Vis.*, 9:210 (2003)) or VEGFr. siRNA sequences that target VEGFr are set forth in, e.g., GB 2396864; U.S. Patent Publication No. 20040142895; and CA2456444.

Anti-angiogenic genes are able to inhibit neovascularization. These genes are particularly useful for treating those cancers in which angiogenesis plays a role in the pathological development of the disease. Examples of anti-angiogenic genes include, but are not limited to, endostatin (see, e.g., U.S. Pat. No. 6,174,861), angiostatin (see, e.g., U.S. Pat. No. 5,639,725), and VEGF-R2 (see, e.g., Decaussin et al., *J. Pathol.*, 188: 369-377 (1999)).

Immunomodulator genes are genes that modulate one or more immune responses. Examples of immunomodulator genes include, without limitation, cytokines such as growth factors (e.g., TGF-α, TGF-β, EGF, FGF, IGF, NGF, PDGF, CGF, GM-CSF, SCF, etc.), interleukins (e.g., IL-2, IL-4, IL-12 (Hill et al., *J. Immunol.*, 171:691 (2003)), IL-15, IL-18, IL-20, etc.), interferons (e.g., IFN-α, IFN-β, IFN-γ, etc.) and TNF. Fas and Fas Ligand genes are also immunomodulator target sequences of interest (Song et al, *Nat. Med.*, 9:347 (2003)). Genes encoding secondary signaling molecules in hematopoietic and lymphoid cells are also included in the present invention, for example, Tec family kinases such as Bruton's tyrosine kinase (Btk) (Heinonen et al, *FEBS Lett.*, 527:274 (2002)).

Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g., inhibit, activate, etc.) the physiological pathway that the receptor is involved in (e.g., glucose level modulation, blood cell development, mitogenesis, etc.). Examples of cell receptor ligands include, but are not limited to, cytokines, growth factors, interleukins, interferons, erythropoietin (EPO), insulin, glucagon, G-protein coupled receptor ligands, etc. Templates coding for an expansion of trinucleotide repeats (e.g., CAG repeats) find use in silencing pathogenic sequences in neurodegenerative disorders caused by the expansion of trinucleotide repeats, such as spinobulbular muscular atrophy and Huntington's Disease (Caplen et al., Hum. Mol. Genet., 11:175 (2002)).

In addition to its utility in silencing the expression of any of the above-described genes for therapeutic purposes, the siRNA described herein are also useful in research and development applications as well as diagnostic, prophylactic, prognostic, clinical, and other healthcare applications. As a non-limiting example, the modified siRNA of the present invention can be used in target validation studies directed at testing whether the gene of interest has the potential to be a therapeutic target. The modified siRNA of the present invention can also be used in target identification studies aimed at discovering genes as potential therapeutic targets.

IV. Lipid-Based Carrier Systems Containing siRNA

In one aspect, the present invention provides stabilized nucleic acid-lipid particles (SPLPs or SNALPs) and other lipid-based carrier systems containing the modified siRNA described herein. Preferably, the lipid-based carrier system is an SPLP or SNALP. Alternatively, the lipid-based carrier system is a liposome, micelle, virosome, nucleic acid complex, or mixtures thereof.

Non-limiting examples of alternative lipid-based carrier systems suitable for use in the present invention include polycationic polymer/nucleic acid complexes (see, e.g., U.S. Patent Publication Nos. 20050222064 and 20030185890), cyclodextrin-polymer/nucleic acid complexes (see, e.g., U.S. Patent Publication No. 20040087024), biodegradable poly(β-amino ester) polymer/nucleic acid complexes (see, e.g., U.S. Patent Publication No. 20040071654), pH-sensitive liposomes (see, e.g., U.S. Patent Publication No. 20020192274; AU 2003210303), anionic liposomes (see, e.g., U.S. Patent Publication No. 20030026831), cationic liposomes (see, e.g., U.S. Patent Publication Nos. 20030229040, 20020160038, and 20020012998; U.S. Pat. No. 5,908,635; PCT Patent Publication No. WO 01/72283), antibody-coated liposomes (see, e.g., U.S. Patent Publication No. 20030108597; PCT Patent Publication No. WO 00/50008), reversibly masked lipoplexes (see, e.g., U.S. Patent Publication Nos. 20030180950), cell-type specific liposomes (see, e.g., U.S. Patent Publication No. 20030198664), liposomes containing nucleic acid and peptides (see, e.g., U.S. Pat. No. 6,207,456), microparticles containing polymeric matrices (see, e.g., U.S. Patent Publication No. 20040142475), pH-sensitive lipoplexes (see, e.g., U.S. Patent Publication No. 20020192275), liposomes containing lipids derivatized with releasable hydrophilic polymers (see, e.g., U.S. Patent Publication No. 20030031704), lipid-entrapped nucleic acid (see, e.g., PCT Patent Publication Nos. WO 03/057190 and WO 03/059322), lipid-encapsulated nucleic acid (see, e.g., U.S. Patent Publication No. 20030129221; U.S. Pat. No. 5,756,122), polycationic sterol derivative/nucleic acid complexes (see, e.g., U.S. Pat. No. 6,756,054), other liposomal compositions (see, e.g., U.S. Patent Publication Nos. 20030035829 and 20030072794; U.S. Pat. No. 6,200,599), other microparticle compositions (see, e.g., U.S. Patent Publication No. 20030157030), polyplexes (see, e.g., PCT Patent Publication No. WO 03/066069), emulsion compositions (see, e.g., U.S. Pat. No. 6,747,014), condensed nucleic acid complexes (see, e.g., U.S. Patent Publication No. 20050123600), other polycationic/nucleic acid complexes (see, e.g., U.S. Patent Publication No. 20030125281), polyvinylether/nucleic acid complexes (see, e.g., U.S. Patent Publication No. 20040156909), polycyclic amidinium/nucleic acid complexes (see, e.g., U.S. Patent Publication No. 20030220289), nanocapsule and microcapsule compositions (see, e.g., AU 2002358514; PCT Patent Publication No. WO 02/096551), stabilized mixtures of liposomes and emulsions (see, e.g., EP1304160), porphyrin/nucleic acid complexes (see, e.g., U.S. Pat. No. 6,620,805), lipid-nucleic acid complexes (see, e.g., U.S. Patent Publication No. 20030203865), nucleic acid micro-emulsions (see, e.g., U.S. Patent Publication No. 20050037086), and cationic lipid-based compositions (see, e.g., U.S. Patent Publication No. 20050234232). One skilled in the art will appreciate that modified siRNA of the present invention can also be delivered as a naked siRNA molecule.

A. Stabilized Nucleic Acid-Lipid Particles

The stabilized nucleic acid-lipid particles of the present invention typically comprise a modified siRNA as described herein, a cationic lipid, and a non-cationic lipid. The stabilized nucleic acid-lipid particles can further comprise a conjugated lipid that prevents aggregation of the particles. SPLPs or SNALPs typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids are resistant in aqueous solution to degradation with a nuclease when present in the nucleic acid-lipid particles. Nucleic acid-lipid particles and their method of preparation are disclosed in, e.g., U.S. Pat. Nos. 5,753,613; 5,785,992; 5,705,385; 5,976,567; 5,981,501; 6,110,745; and 6,320,017; and PCT Patent Publication No. WO 96/40964.

1. Cationic Lipids

Any of a variety of cationic lipids may be used in the stabilized nucleic acid-lipid particles of the present invention, either alone or in combination with one or more other cationic lipid species or non-cationic lipid species.

Cationic lipids which are useful in the present invention can be any of a number of lipid species which carry a net positive charge at physiological pH. Such lipids include, but are not limited to, DODAC, DODMA, DSDMA, DOTMA, DDAB, DOTAP, DOSPA, DOGS, DC-Chol, DMRIE, and mixtures thereof. A number of these lipids and related analogs have been described in U.S. Patent Publication No. 20060083780; U.S. Pat. Nos. 5,208,036; 5,264,618; 5,279,833; 5,283,185; and 5,753,613; and 5,785,992; and PCT Patent Publication No. WO 96/10390. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

Furthermore, cationic lipids of Formula I having the following structures are useful in the present invention.

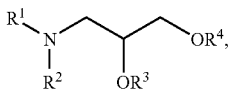

(I)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl (C18), etc. In certain other instances, $R^3$ and $R^4$ are different, i.e., $R^3$ is tetradectrienyl (C14) and $R^4$ is linoleyl (C18). In a preferred embodiment, the cationic lipid of Formula I is symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl. In a particularly preferred embodiments, the cationic lipid of Formula I is DLinDMA or DLenDMA.

Moreover, cationic lipids of Formula II having the following structures are useful in the present invention.

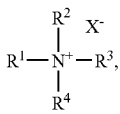

(II)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl (C18), etc. In certain other instances, $R^3$ and $R^4$ are different, i.e., $R^3$ is tetradectrienyl (C14) and $R^4$ is linoleyl (C18). In a preferred embodiment, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

The cationic lipid typically comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % of the total lipid present in the particle. It will be readily apparent to one of skill in the art that depending on the intended use of the particles, the proportions of the components can be varied and the delivery efficiency of a particular formulation can be measured using, e.g., an endosomal release parameter (ERP) assay.

2. Non-Cationic Lipids

The non-cationic lipids used in the stabilized nucleic acid-lipid particles of the present invention can be any of a variety of neutral uncharged, zwitterionic, or anionic lipids capable of producing a stable complex. They are preferably neutral, although they can alternatively be positively or negatively charged. Examples of non-cationic lipids include, without limitation, phospholipid-related materials such as lecithin, phosphatidylethanolamine, lysolecithin, lysophosphatidylethanolamine, phosphatidylserine, phosphatidylinositol, sphingomyelin, cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), palmitoyloleoyl-phosphatidylglycerol (POPG), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, and 1-stearoyl-2-oleoyl-phosphatidyethanolamine (SOPE). Non-cationic lipids or sterols such as cholesterol may also be present. Additional nonphosphorous containing lipids include, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, ceramide, diacylphosphatidylcholine, and diacylphosphatidylethanolamine. Other lipids such as lysophosphatidylcholine and lysophosphatidylethanolamine may be present. Non-cationic lipids also include polyethylene glycol-based polymers such as PEG 2000, PEG 5000, and polyethylene glycol conjugated to phospholipids or to ceramides (referred to as PEG-Cer), as described in U.S. application Ser. No. 08/316,429.

In preferred embodiments, the non-cationic lipids are diacylphosphatidylcholine (e.g., distearoylphosphatidylcholine, dioleoylphosphatidylcholine, dipalmitoylphosphatidylcholine, and dilinoleoylphosphatidylcholine), diacylphosphatidylethanolamine (e.g., dioleoylphosphatidylethanolamine and palmitoyloleoylphosphatidylethanolamine), ceramide, or sphingomyelin. The acyl groups in these lipids are preferably acyl groups derived from fatty acids having $C_{10}$-$C_{24}$ carbon chains. More preferably, the acyl groups are lauroyl, myristoyl, palmitoyl, stearoyl, or oleoyl. In particularly preferred embodiments, the non-cationic lipid will include one or more of cholesterol, 1,2-sn-dioleoylphosphatidylethanolamine, or egg sphingomyelin (ESM).

The non-cationic lipid typically comprises from about 5 mol % to about 90 mol %, from about 10 mol % to about 85 mol %, from about 20 mol % to about 80 mol %, or about 20 mol % of the total lipid present in the particle. The particles may further comprise cholesterol. If present, the cholesterol typically comprises from about 0 mol % to about 10 mol %, from about 2 mol % to about 10 mol %, from about 10 mol % to about 60 mol %, from about 12 mol % to about 58 mol %, from about 20 mol % to about 55 mol %, or about 48 mol % of the total lipid present in the particle.

3. Bilayer Stabilizing Component

In addition to cationic and non-cationic lipids, the stabilized nucleic acid-lipid particles of the present invention can comprise a bilayer stabilizing component (BSC) such as an ATTA-lipid or a PEG-lipid, such as PEG coupled to dialkyloxypropyls (PEG-DAA) as described in, e.g., PCT Patent Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides, or a mixture thereof (see, e.g., U.S. Pat. No. 5,885,613). In a preferred embodiment, the BSC is a conjugated lipid that prevents the aggregation of particles. Suitable conjugated lipids include, but are not limited to, PEG-lipid conjugates, ATTA-lipid conjugates, cationic-polymer-lipid conjugates (CPLs), and mixtures thereof. In another preferred embodiment, the particles comprise either a PEG-lipid conjugate or an ATTA-lipid conjugate together with a CPL.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycolamine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH) is particularly useful for preparing the PEG-lipid conjugates including, e.g., PEG-DAA conjugates.

In a preferred embodiment, the PEG has an average molecular weight of from about 550 daltons to about 10,000 daltons, more preferably from about 750 daltons to about 5,000 daltons, more preferably from about 1,000 daltons to about 5,000 daltons, more preferably from about 1,500 daltons to about 3,000 daltons, and even more preferably about 2,000 daltons or about 750 daltons. The PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties.

In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the bilayer stabilizing component. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoylphosphatidylethanolamine (DMPE), dipalmitoylphosphatidylethanolamine (DPPE), dioleoylphosphatidylethanolamine (DOPE), and distearoylphosphatidylethanolamine (DSPE).

The term "ATTA" or "polyamide" refers to, without limitation, compounds disclosed in U.S. Pat. Nos. 6,320,017 and 6,586,559. These compounds include a compound having the formula:

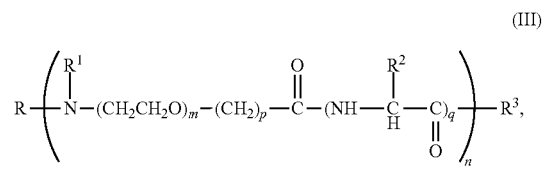

(III)

wherein R is a member selected from the group consisting of hydrogen, alkyl and acyl; R$^1$ is a member selected from the group consisting of hydrogen and alkyl; or optionally, R and R$^1$ and the nitrogen to which they are bound form an azido moiety; R$^2$ is a member of the group selected from hydrogen, optionally substituted alkyl, optionally substituted aryl and a side chain of an amino acid; R$^3$ is a member selected from the group consisting of hydrogen, halogen, hydroxy, alkoxy, mercapto, hydrazino, amino and NR$^4$R$^5$, wherein R$^4$ and R$^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" refers to a compound having 2 fatty acyl chains, R$^1$ and R$^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauryl (C12), myristyl (C14), palmityl (C16), stearyl (C18), and icosyl (C20). In preferred embodiments, R$^1$ and R$^2$ are the same, i.e., R$^1$ and R$^2$ are both myristyl (i.e., dimyristyl), R$^1$ and R$^2$ are both stearyl (i.e., distearyl), etc. Diacylglycerols have the following general formula:

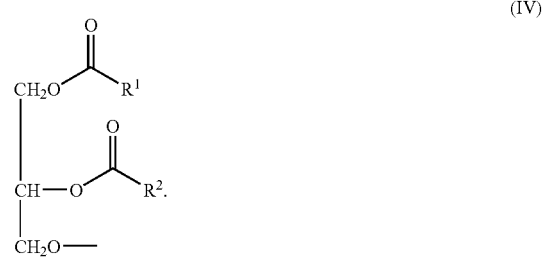

(IV)

The term "dialkyloxypropyl" refers to a compound having 2 alkyl chains, R$^1$ and R$^2$, both of which have independently between 2 and 30 carbons. The alkyl groups can be saturated or have varying degrees of unsaturation. Dialkyloxypropyls have the following general formula:

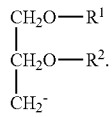 (V)

In a preferred embodiment, the PEG-lipid is a PEG-DAA conjugate having the following formula:

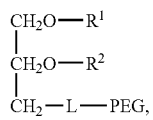 (VI)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, lauryl (C12), myristyl (C14), palmityl (C16), stearyl (C18), and icosyl (C20). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VI above, the PEG has an average molecular weight ranging from about 550 daltons to about 10,000 daltons, more preferably from about 750 daltons to about 5,000 daltons, more preferably from about 1,000 daltons to about 5,000 daltons, more preferably from about 1,500 daltons to about 3,000 daltons, and even more preferably about 2,000 daltons or about 750 daltons. The PEG can be optionally substituted with alkyl, alkoxy, acyl, or aryl. In a preferred embodiment, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992), Larock, COMPREHENSIVE ORGANIC TRANSFORMATIONS (VCH 1989); and Furniss, VOGEL'S TEXTBOOK OF PRACTICAL ORGANIC CHEMISTRY 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a dilauryloxypropyl (C12)-PEG conjugate, dimyristyloxypropyl (C14)-PEG conjugate, a dipalmityloxypropyl (C16)-PEG conjugate, or a distearyloxypropyl (C18)-PEG conjugate. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the particles (e.g., SNALPs or SPLPs) of the present invention can further comprise cationic poly(ethylene glycol) (PEG) lipids or CPLs that have been designed for insertion into lipid bilayers to impart a positive charge (see, e.g., Chen et al., Bioconj. Chem. 11:433-437 (2000)). Suitable SPLPs and SPLP-CPLs for use in the present invention, and methods of making and using SPLPs and SPLP-CPLs, are disclosed, e.g., in U.S. Pat. No. 6,852,334 and PCT Patent Publication No. WO 00/62813. Cationic polymer lipids (CPLs) useful in the present invention have the following architectural features: (1) a lipid anchor, such as a hydrophobic lipid, for incorporating the CPLs into the lipid bilayer; (2) a hydrophilic spacer, such as a polyethylene glycol, for linking the lipid anchor to a cationic head group; and (3) a polycationic moiety, such as a naturally occurring amino acid, to produce a protonizable cationic head group.

Suitable CPLs include compounds of Formula VII:

 (VII), wherein A, W, and Y are as described below.

With reference to Formula VII, "A" is a lipid moiety such as an amphipathic lipid, a neutral lipid, or a hydrophobic lipid that acts as a lipid anchor. Suitable lipid examples include vesicle-forming lipids or vesicle adopting lipids and include, but are not limited to, diacylglycerolyls, dialkylglycerolyls, N—N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatable polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

The bilayer stabilizing component (e.g., PEG-lipid) typically comprises from about 0 mol % to about 20 mol %, from about 0.5 mol % to about 20 mol %, from about 1.5 mol % to about 18 mol %, from about 4 mol % to about 15 mol %, from about 5 mol % to about 12 mol %, or about 2 mol % of the total lipid present in the particle. One of ordinary skill in the art will appreciate that the concentration of the bilayer stabilizing component can be varied depending on the bilayer stabilizing component employed and the rate at which the nucleic acid-lipid particle is to become fusogenic.

By controlling the composition and concentration of the bilayer stabilizing component, one can control the rate at which the bilayer stabilizing component exchanges out of the nucleic acid-lipid particle and, in turn, the rate at which the nucleic acid-lipid particle becomes fusogenic. For instance, when a polyethyleneglycol-phosphatidylethanolamine conjugate or a polyethyleneglycol-ceramide conjugate is used as the bilayer stabilizing component, the rate at which the nucleic acid-lipid particle becomes fusogenic can be varied, for example, by varying the concentration of the bilayer stabilizing component, by varying the molecular weight of the polyethyleneglycol, or by varying the chain length and degree of saturation of the acyl chain groups on the phosphatidylethanolamine or the ceramide. In addition, other variables including, for example, pH, temperature, ionic strength, etc. can be used to vary and/or control the rate at which the nucleic acid-lipid particle becomes fusogenic. Other methods which can be used to control the rate at which the nucleic acid-lipid particle becomes fusogenic will become apparent to those of skill in the art upon reading this disclosure.

V. Preparation of Nucleic Acid-Lipid Particles

The serum-stable nucleic acid-lipid particles of the present invention, in which the modified siRNA described herein is encapsulated in a lipid bilayer and is protected from degradation, can be formed by any method known in the art including, but not limited to, a continuous mixing method, a direct dilution process, a detergent dialysis method, or a modification of a reverse-phase method which utilizes organic solvents to provide a single phase during mixing of the components.

In preferred embodiments, the cationic lipids are lipids of Formula I and II or combinations thereof. In other preferred embodiments, the noncationic lipids are ESM, DOPE, DOPC, DPPE, DMPE, 16:0 Monomethyl Phosphatidylethanolamine, 16:0 Dimethyl Phosphatidylethanolamine, 18:1 Trans Phosphatidylethanolamine, 18:0 18:1 Phosphatidylethanolamine (SOPE), 16:0 18:1 Phosphatidylethanolamine, DSPE, polyethylene glycol-based polymers (e.g., PEG 2000, PEG 5000, PEG-modified diacylglycerols, or PEG-modified dialkyloxypropyls), distearoylphosphatidylcholine (DSPC), cholesterol, or combinations thereof. In still other preferred embodiments, the organic solvents are methanol, chloroform, methylene chloride, ethanol, diethyl ether, or combinations thereof.

In a particularly preferred embodiment, the present invention provides for nucleic acid-lipid particles produced via a continuous mixing method, e.g., process that includes providing an aqueous solution comprising a nucleic acid such as an siRNA in a first reservoir, providing an organic lipid solution in a second reservoir, and mixing the aqueous solution with the organic lipid solution such that the organic lipid solution mixes with the aqueous solution so as to substantially instantaneously produce a liposome encapsulating the nucleic acid (e.g., siRNA). This process and the apparatus for carrying this process are described in detail in U.S. Patent Publication No. 20040142025.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The serum-stable nucleic acid-lipid particles formed using the continuous mixing method typically have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

In another embodiment, the present invention provides for nucleic acid-lipid particles produced via a direct dilution process that includes forming a liposome solution and immediately and directly introducing the liposome solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of liposome solution introduced thereto. As a non-limiting example, a liposome solution in 45% ethanol when introduced into the collection vessel containing an equal volume of aqueous solution will advantageously yield smaller particles in about 22.5% ethanol.

In yet another embodiment, the present invention provides for nucleic acid-lipid particles produced via a direct dilution process in which a third reservoir containing dilution buffer is fluidly coupled to a second mixing region. In this embodiment, the liposome solution formed in a first mixing region is immediately and directly mixed with dilution buffer in the second mixing region. In preferred aspects, the second mixing region includes a T-connector arranged so that the liposome solution and the dilution buffer flows meet as opposing 180° flows; however, connectors providing shallower angles can be used, e.g., from about 27° to about 180°. A pump mechanism delivers a controllable flow of buffer to the second mixing region. In one aspect, the flow rate of dilution buffer provided to the second mixing region is controlled to be substantially equal to the flow rate of liposome solution introduced thereto from the first mixing region. This embodiment advantageously allows for more control of the flow of dilution buffer mixing with the liposome solution in the second mixing region, and therefore also the concentration of liposome solution in buffer throughout the second mixing process. Such control of the dilution buffer flow rate advantageously allows for small particle size formation at reduced concentrations.

These processes and the apparatuses for carrying out these direct dilution processes is described in detail in U.S. Provisional Patent Application No. 60/703,380.

The serum-stable nucleic acid-lipid particles formed using the direct dilution process typically have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

In some embodiments, the particles are formed using detergent dialysis. Without intending to be bound by any particular mechanism of formation, a nucleic acid such as an siRNA is contacted with a detergent solution of cationic lipids to form a coated nucleic acid complex. These coated nucleic acids can aggregate and precipitate. However, the presence of a detergent reduces this aggregation and allows the coated nucleic acids to react with excess lipids (typically, non-cationic lipids) to form particles in which the nucleic acid is encapsulated in a lipid bilayer. Thus, the serum-stable nucleic acid-lipid particles can be prepared as follows:

(a) combining a nucleic acid with cationic lipids in a detergent solution to form a coated nucleic acid-lipid complex;

(b) contacting non-cationic lipids with the coated nucleic acid-lipid complex to form a detergent solution comprising a nucleic acid-lipid complex and non-cationic lipids; and (c) dialyzing the detergent solution of step (b) to provide a solution of serum-stable nucleic acid-lipid particles, wherein the nucleic acid is encapsulated in a lipid bilayer and the particles are serum-stable and have a size of from about 50 to about 150 nm.

An initial solution of coated nucleic acid-lipid complexes is formed by combining the nucleic acid with the cationic lipids in a detergent solution. In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent, 3-08; Zwittergent 3-10; Triton X-405; hexyl-, heptyl-, octyl- and nonyl-p-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and nucleic acids will typically be combined to produce a charge ratio (+/−) of about 1:1 to about 20:1, in a ratio of about 1:1 to about 12:1, or in a ratio of about 2:1 to about 6:1. Additionally, the overall concentration of nucleic acid in solution will typically be from about 25 µg/mL to about 1 mg/mL, from about 25 µg/mL to about 200 µg/mL, or from about 50 µg/mL to about 100 µg/mL. The combination of nucleic acids and cationic lipids in detergent solution is kept, typically at room temperature, for a period of time which is sufficient for the coated complexes to form. Alternatively, the nucleic acids and cationic lipids can be combined in the detergent solution and warmed to temperatures of up to about 37° C., about 50° C., about 60° C., or about 70° C. For nucleic acids which are particularly sensitive to temperature, the coated complexes can be formed at lower temperatures, typically down to about 4° C.

In some embodiments, the nucleic acid to lipid ratios (mass/mass ratios) in a formed nucleic acid-lipid particle will range from about 0.01 to about 0.2, from about 0.03 to about 0.01, or from about 0.01 to about 0.08. The ratio of the starting materials also falls within this range. In other embodiments, the nucleic acid-lipid particle preparation uses about 400 µg nucleic acid per 10 mg total lipid or a nucleic acid to lipid ratio of about 0.01 to about 0.08 and, more preferably, about 0.04, which corresponds to 1.25 mg of total lipid per 50 µg of nucleic acid.

The detergent solution of the coated nucleic acid-lipid complexes is then contacted with non-cationic lipids to provide a detergent solution of nucleic acid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide or sphingomyelin. The acyl groups in these lipids are preferably acyl groups derived from fatty acids having $C_{10}$-$C_{24}$ carbon chains. More preferably the acyl groups are lauroyl, myristoyl, palmitoyl, stearoyl or oleoyl. In particularly preferred embodiments, the non-cationic lipid will be 1,2-sn-dioleoylphosphatidylethanolamine (DOPE), palmitoyl oleoyl phosphatidylcholine (POPC), egg phosphatidylcholine (EPC), distearoylphosphatidylcholine (DSPC), cholesterol, or a mixture thereof. In the most preferred embodiments, the nucleic acid-lipid particles will be fusogenic particles with enhanced properties in vivo and the non-cationic lipid will be DSPC or DOPE. In addition, the nucleic acid-lipid particles of the present invention may further comprise cholesterol. In other preferred embodiments, the non-cationic lipids will further comprise polyethylene glycol-based polymers such as PEG 2,000, PEG 5,000 and polyethylene glycol conjugated to a diacylglycerol, a ceramide, or a phospholipid, as described in U.S. Pat. No. 5,820,873 and U.S. Patent Publication No. 20030077829. In further preferred embodiments, the non-cationic lipids will further comprise polyethylene glycol-based polymers such as PEG 2,000, PEG 5,000 and polyethylene glycol conjugated to a dialkyloxypropyl.

The amount of non-cationic lipid which is used in the present methods is typically about 2 to about 20 mg of total lipids to 50 µg of nucleic acid. Preferably, the amount of total lipid is from about 5 to about 10 mg per 50 µg of nucleic acid.

Following formation of the detergent solution of nucleic acid-lipid complexes and non-cationic lipids, the detergent is removed, preferably by dialysis. The removal of the detergent results in the formation of a lipid-bilayer which surrounds the nucleic acid providing serum-stable nucleic acid-lipid particles which have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

The serum-stable nucleic acid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the serum-stable nucleic acid-lipid particles can be prepared as follows:

(a) preparing a mixture comprising cationic lipids and non-cationic lipids in an organic solvent;

(b) contacting an aqueous solution of nucleic acid with the mixture in step (a) to provide a clear single phase; and (c) removing the organic solvent to provide a suspension of nucleic acid-lipid particles, wherein the nucleic acid is encapsulated in a lipid bilayer and the particles are stable in serum and have a size of from about 50 to about 150 nm.

The nucleic acids (e.g., siRNA), cationic lipids, and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of nucleic acid and lipids. Suitable solvents include, but are not limited to, chloroform, dichloromethane, diethylether, cyclohexane, cyclopentane, benzene, toluene, methanol, or other aliphatic alcohols such as propanol, iso-propanol, butanol, tert-butanol, iso-butanol, pentanol and hexanol. Combinations of two or more solvents may also be used in the present invention.

Contacting the nucleic acid with the organic solution of cationic and non-cationic lipids is accomplished by mixing together a first solution of nucleic acid, which is typically an aqueous solution, and a second organic solution of the lipids. One of skill in the art will understand that this mixing can take place by any number of methods, for example, by mechanical means such as by using vortex mixers.

After the nucleic acid has been contacted with the organic solution of lipids, the organic solvent is removed, thus forming an aqueous suspension of serum-stable nucleic acid-lipid particles. The methods used to remove the organic solvent will typically involve evaporation at reduced pressures or blowing a stream of inert gas (e.g., nitrogen or argon) across the mixture.

The serum-stable nucleic acid-lipid particles thus formed will typically be sized from about 50 nm to about 150 nm, from about 60 nm to about 130 nm, from about 70 nm to about 110 nm, or from about 70 nm to about 90 nm. To achieve further size reduction or homogeneity of size in the particles, sizing can be conducted as described above.

In other embodiments, the methods will further comprise adding non-lipid polycations which are useful to effect the delivery to cells using the present compositions. Examples of suitable non-lipid polycations include, but are limited to, hexadimethrine bromide (sold under the brand name POLY-BRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine, and polyethyleneimine.

In certain embodiments, the formation of the nucleic acid-lipid particles can be carried out either in a mono-phase system (e.g., a Bligh and Dyer monophase or similar mixture of aqueous and organic solvents) or in a two-phase system with suitable mixing.

When formation of the complexes is carried out in a mono-phase system, the cationic lipids and nucleic acids are each dissolved in a volume of the mono-phase mixture. Combination of the two solutions provides a single mixture in which the complexes form. Alternatively, the complexes can form in two-phase mixtures in which the cationic lipids bind to the nucleic acid (which is present in the aqueous phase), and "pull" it into the organic phase.

In another embodiment, the serum-stable nucleic acid-lipid particles can be prepared as follows:

(a) contacting nucleic acids with a solution comprising non-cationic lipids and a detergent to form a nucleic acid-lipid mixture;

(b) contacting cationic lipids with the nucleic acid-lipid mixture to neutralize a portion of the negative charge of the nucleic acids and form a charge-neutralized mixture of nucleic acids and lipids; and (c) removing the detergent from the charge-neutralized mixture to provide the nucleic acid-lipid particles in which the nucleic acids are protected from degradation.

In one group of embodiments, the solution of non-cationic lipids and detergent is an aqueous solution. Contacting the nucleic acids with the solution of non-cationic lipids and detergent is typically accomplished by mixing together a first solution of nucleic acids and a second solution of the lipids and detergent. One of skill in the art will understand that this mixing can take place by any number of methods, for example, by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to 5 times the amount of cationic lipid, preferably from about 0.5 to about 2 times the amount of cationic lipid used.

In some embodiments, the nucleic acids are precondensed as described in, e.g., U.S. patent application Ser. No. 09/744,103.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DLinDMA and DLenDMA. These lipids and related analogs have been described in U.S. Patent Publication No. 20060083780.

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the nucleic acid-lipid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 50 nm to several microns, about 50 nm to about 150 nm, from about 60 nm to about 130 nm, from about 70 nm to about 110 nm, or from about 70 nm to about 90 nm. To achieve further size reduction or homogeneity of size in the particles, the nucleic acid-lipid particles can be sonicated, filtered, or subjected to other sizing techniques which are used in liposomal formulations and are known to those of skill in the art.

In other embodiments, the methods will further comprise adding non-lipid polycations which are useful to effect the lipofection of cells using the present compositions. Examples of suitable non-lipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine. Addition of these salts is preferably after the particles have been formed.

In another aspect, the serum-stable nucleic acid-lipid particles can be prepared as follows:

(a) contacting an amount of cationic lipids with nucleic acids in a solution; the solution comprising from about 15-35% water and about 65-85% organic solvent and the amount of cationic lipids being sufficient to produce a +/− charge ratio of from about 0.85 to about 2.0, to provide a hydrophobic nucleic acid-lipid complex;

(b) contacting the hydrophobic, nucleic acid-lipid complex in solution with non-cationic lipids, to provide a nucleic acid-lipid mixture; and (c) removing the organic solvents from the nucleic acid-lipid mixture to provide nucleic acid-lipid particles in which the nucleic acids are protected from degradation.

The nucleic acids (e.g., siRNA), non-cationic lipids, cationic lipids, and organic solvents which are useful in this aspect of the invention are the same as those described for the methods above which used detergents. In one group of embodiments, the solution of step (a) is a mono-phase. In another group of embodiments, the solution of step (a) is two-phase.

In preferred embodiments, the non-cationic lipids are ESM, DOPE, DOPC, polyethylene glycol-based polymers (e.g., PEG 2,000, PEG 5,000, PEG-modified diacylglycerols, or PEG-modified dialkyloxypropyls), distearoylphosphatidylcholine (DSPC), DPPE, DMPE, 16:0 Monomethyl Phosphatidylethanolamine, 16:0 Dimethyl Phosphatidylethanolamine, 18:1 Trans Phosphatidylethanolamine, 18:0 18:1 Phosphatidylethanolamine (SOPE), 16:0 18:1 Phosphatidylethanolamine, DSPE, cholesterol, or combinations thereof. In still other preferred embodiments, the organic solvents are methanol, chloroform, methylene chloride, ethanol, diethyl ether or combinations thereof.

In one embodiment, the nucleic acid is a modified siRNA as described herein; the cationic lipid is DLindMA, DLenDMA, DODAC, DDAB, DOTMA, DOSPA, DMRIE, DOGS or combinations thereof; the non-cationic lipid is ESM, DOPE, DAG-PEGs, distearoylphosphatidylcholine (DSPC), DPPE, DMPE, 16:0 Monomethyl Phosphatidylethanolamine, 16:0 Dimethyl Phosphatidylethanolamine, 18:1 Trans Phosphatidylethanolamine, 18:0 18:1 Phosphatidylethanolamine (SOPE), 16:0 18:1 Phosphatidylethanolamine DSPE, cholesterol, or combinations thereof (e.g., DSPC and PEG-DAA); and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to about 15 times the amount (on a mole basis) of cationic lipids which was used to provide the charge-neutralized nucleic acid-lipid complex. Preferably, the amount is from about 0.5 to about 9 times the amount of cationic lipids used.

In one embodiment, the nucleic acid-lipid particles preparing according to the above-described methods are either net charge neutral or carry an overall charge which provides the particles with greater gene lipofection activity. Preferably, the nucleic acid component of the particles is a nucleic acid which interferes with the production of an undesired protein. In other preferred embodiments, the non-cationic lipid may further comprise cholesterol.

A variety of general methods for making SNALP-CPLs (CPL-containing SNALPs) are discussed herein. Two general techniques include "post-insertion" technique, that is, insertion of a CPL into for example, a pre-formed SNALP, and the "standard" technique, wherein the CPL is included in the lipid mixture during for example, the SNALP formation steps. The post-insertion technique results in SNALPs having CPLs mainly in the external face of the SNALP bilayer membrane, whereas standard techniques provide SNALPs having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPL, are taught, for example, in U.S. Pat. Nos. 5,705,385; 6,586,410; 5,981,501; 6,534,484; and 6,852,334; U.S. Patent Publication No. 20020072121; and PCT Patent Publication No. WO 00/62813.

VI. Kits

The present invention also provides nucleic acid-lipid particles in kit form. The kit may comprise a container which is compartmentalized for holding the various elements of the nucleic acid-lipid particles (e.g., the nucleic acids and the individual lipid components of the particles). In some embodiments, the kit contains the nucleic acid-lipid particle compositions of the present invention, preferably in dehydrated form, with instructions for their rehydration and administration.

VII. Administration of Nucleic Acid-Lipid Particles

The serum-stable nucleic acid-lipid particles of the present invention are useful for the introduction of nucleic acids into cells. Accordingly, the present invention also provides methods for introducing a nucleic acid (e.g., an interfering RNA) into a cell. As a result, the immunostimulatory effects of the siRNA can be diminished using the modified siRNA sequences described herein while retaining RNAi activity. The methods are carried out in vitro or in vivo by first forming the particles as described above and then contacting the particles with the cells for a period of time sufficient for delivery of the interfering RNA to occur.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

A. In Vitro Delivery

For in vitro applications, the delivery of nucleic acids can be to any cell grown in culture, whether of plant or animal origin, vertebrate or invertebrate, and of any tissue or type. In preferred embodiments, the cells are animal cells, more preferably mammalian cells, and most preferably human cells.

Contact between the cells and the nucleic acid-lipid particles, when carried out in vitro, takes place in a biologically compatible medium. The concentration of particles varies widely depending on the particular application, but is generally between about 1 μmol and about 10 mmol. Treatment of the cells with the nucleic acid-lipid particles is generally carried out at physiological temperatures (about 37° C.) for periods of time of from about 1 to 48 hours, preferably of from about 2 to 4 hours.

In one group of preferred embodiments, a nucleic acid-lipid particle suspension is added to 60-80% confluent plated cells having a cell density of from about $10^3$ to about $10^5$ cells/mL, more preferably about $2 \times 10^4$ cells/mL. The concentration of the suspension added to the cells is preferably of from about 0.01 to 0.2 μg/mL, more preferably about 0.1 μg/mL.

Using an Endosomal Release Parameter (ERP) assay, the delivery efficiency of the SNALP or other lipid-based carrier system can be optimized. An ERP assay is described in detail in U.S. Patent Publication No. 20030077829. More particularly, the purpose of an ERP assay is to distinguish the effect of various cationic lipids and helper lipid components of SNALPs based on their relative effect on binding/uptake or fusion with/destabilization of the endosomal membrane. This assay allows one to determine quantitatively how each component of the SNALP or other lipid-based carrier system effects delivery efficiency, thereby optimizing the SNALPs or other lipid-based carrier systems. Usually, an ERP assay measures expression of a reporter protein (e.g., luciferase, β-galactosidase, green fluorescent protein, etc.), and in some instances, a SNALP formulation optimized for an expression plasmid will also be appropriate for encapsulating an interfering RNA. In other instances, an ERP assay can be adapted to measure downregulation of transcription or translation of a target sequence in the presence or absence of an interfering RNA. By comparing the ERPs for each of the various SNALPs or other lipid-based formulations, one can readily determine the optimized system, e.g., the SNALP or other lipid-based formulation that has the greatest uptake in the cell.

Suitable labels for carrying out the ERP assay of the present invention include, but are not limited to, spectral labels, such as fluorescent dyes (e.g., fluorescein and derivatives such as fluorescein isothiocyanate (FITC) and Oregon Green™, rhodamine and derivatives such as Texas red, tetrarhodimine isothiocynate (TRITC), etc.), digoxigenin, biotin, phycoerythrin, AMCA, CyDyes□, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold; or colored glass or plastic beads such as polystyrene, polypropylene, latex, etc. The label can be coupled directly or indirectly to a component of the SNALP or other lipid-based carrier system using methods well known in the art. As indicated above, a wide variety of labels can be used, with the choice of label depending on sensitivity required, ease of conjugation with the SNALP component, stability requirements, and available instrumentation and disposal provisions.

B. In Vivo Delivery

The nucleic acid-lipid particles of the present invention can be administered via any route known in the art including, e.g., intravenously, intramuscularly, subcutaneously, intradermally, intraperitoneally, orally, intranasally, or topically either alone or in mixture with a physiologically-acceptable carrier (such as physiological saline or phosphate buffer) selected in accordance with the route of administration and standard pharmaceutical practice.

When preparing pharmaceutical preparations of the nucleic acid-lipid particles of the present invention, it is preferable to use quantities of the nucleic acid-lipid particles which have been purified to reduce or eliminate empty lipid particles or particles with nucleic acid portion associated with the external surface. The pharmaceutical carrier is generally added following particle formation. Thus, after the particle is formed, the particle can be diluted into pharmaceutically acceptable carriers.

The concentration of particles in the pharmaceutical formulations can vary widely, e.g., from less than about 0.05%, usually at or at least about 2.5%, to as much as about 10% to about 30% by weight and will be selected primarily by fluid volumes, viscosities, etc., in accordance with the particular mode of administration selected.

1. Injectable Delivery

In certain circumstances, it will be desirable to deliver the pharmaceutical compositions disclosed herein parenterally, intravenously, intramuscularly, subcutaneously, intradermally, or intraperitoneally as described in U.S. Pat. Nos. 5,543,158; 5,641,515, and 5,399,363. Solutions of the nucleic acid-lipid particles may be prepared in water suitably mixed with a surfactant. Dispersions may also be prepared in glycerol, liquid polyethylene glycols, and mixtures thereof and in oils. Typically, these preparations contain a preservative to prevent the growth of microorganisms. Generally, when administered intravenously, the nucleic acid-lipid particles are formulated with a suitable pharmaceutical carrier. Typically, normal buffered saline (e.g., 135-150 mM NaCl) is employed as the pharmaceutically acceptable carrier, but other suitable carriers will suffice. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically-acceptable" refers to molecular entities and compositions that do not produce an allergic or similar untoward reaction when administered to a human. The preparation of an aqueous composition for injection is well understood in the art. Typically, such compositions are prepared as injectables, either as liquid solutions or suspensions; solid forms suitable for solution in, or suspension in, liquid prior to injection can also be prepared. The preparation can also be emulsified.

These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents, and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

The amount of particles administered will depend upon the ratio of nucleic acid to lipid, the particular nucleic acid used, the disease state being treated, the age, weight, and condition of the patient, and the judgment of the clinician, but will generally be between about 0.01 and about 50 mg per kilogram (mg/kg) of body weight, preferably between about 0.1 and about 5 mg/kg of body weight, or about $10^8$-$10^{10}$ particles per injection.

2. Oral Delivery

In certain applications, the nucleic acid-lipid particles disclosed herein may be delivered via oral administration to the individual. The particles may be incorporated with excipients and used in the form of ingestible tablets, buccal tablets, troches, capsules, lozenges, elixirs, mouthwash, suspensions, oral sprays, syrups, wafers, and the like (see, e.g., U.S. Pat. Nos. 5,641,515; 5,580,579, and 5,792,451). The tablets, troches, pills, capsules, lozenges, and the like may also contain the following: binders, gelatin; excipients, lubricants, and/or flavoring agents. When the dosage unit form is a capsule, it may contain, in addition to materials of the above type, a liquid carrier. Various other materials may be present as coatings or to otherwise modify the physical form of the dosage unit. Of course, any material used in preparing any dosage unit form should be pharmaceutically pure and substantially non-toxic in the amounts employed.

Typically, these formulations may contain at least about 0.1% of the nucleic acid-lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of the packaged nucleic acid suspended in diluents, such as water, saline, or PEG 400; (b) capsules, sachets, or tablets, each containing a predetermined amount of the active ingredient, as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

3. Nasal Delivery

The compositions containing nucleic acid-lipid particles, either alone or in combination with other suitable components, can be made into aerosol formulations (i.e., they can be "nebulized") to be administered via inhalation (e.g., intranasally or intratracheally) (see, Brigham et al., Am. J. Sci., 298(4):278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045.

4. Topical Delivery

In another example of their use, nucleic acid-lipid particles can be incorporated into a broad range of topical dosage forms including, but not limited to, gels, oils, emulsions, foams, and the like. For instance, the suspension containing the nucleic acid-lipid particles can be formulated and administered as topical creams, pastes, ointments, gels, lotions, and the like.

VIII. Examples

The present invention will be described in greater detail by way of the following example. The following example is offered for illustrative purposes, and is not intended to limit the present invention in any manner. Those of skill in the art will readily recognize a variety of noncritical parameters which can be changed or modified to yield essentially the same results.

Example 1

Chemical Modification Abrogates Synthetic siRNA Mediated Immune Stimulation and Toxicity In Vivo Synthetic siRNA, when delivered efficiently to immune cells at pharmacologically relevant concentrations, can potently induce Type I interferons and inflammatory cytokines, both in vivo and in vitro in human blood. This example illustrates that this potent induction can be completely abrogated by chemical modification of the siRNA. In particular, siRNA containing an antisense strand completely lacking 2'-OH residues, and thus chemically distinct from RNA, retains potent siRNA activity and efficiently abrogates these immunostimulatory effects. Reduction in immunostimulatory activity also ameliorates the toxicity observed upon administration of liposome-encapsulated siRNA. The findings described herein enable the design of siRNAs that efficiently mediate RNA interference and are well tolerated in vivo, thereby having significant implications for the safe and effective development of siRNA as therapeutic agents.

Results

Chemical modification of immunostimulatory siRNA. To examine the impact of chemical modifications on RNAi potency and the immunostimulatory activity of siRNA, a series of nucleotide modifications were designed in two siRNA duplexes that had shown potent RNA interference. A series of siRNAs directed against the coding regions of firefly luciferase and green fluorescent protein (GFP) were prepared as standard unmodified RNA 21-mers and screened for RNA target knockdown. Two lead siRNA sequences were selected (Table 1), with $IC_{50}$ values of 10 nM for both luciferase and GFP. These sequences served as the basis for the design of a series of duplexes in which one or more modifications were made at the 2' ribose position (FIG. 1). This position was chosen due to its well-established impact on oligonucleotide nuclease resistance (Ruckman et al., *J. Biol. Chem.*, 273: 20556-20567 (1998)). In addition, the relative impact of modifications to the sense and/or antisense strand on immune stimulation in vivo was examined. To minimize potential toxicity of the duplexes, extensive backbone modifications such as phosphorothioates were avoided (Drygin et al., *Nucleic Acids Res.*, 32:6585-6595 (2004)). Purine nucleotides (pu) were modified by substitution of 2'-O-methyl (2'OMe) or 2'-H; pyrimidine nucleotides (py) were modified by substitution of 2'-fluoro (2'-F). These chemical modifications have been found to be compatible with the RNAi machinery (Czaudema et al., *Nucleic Acids Res.*, 31:2705-2716 (2003); Allerson et al., *J. Med. Chem.*, 48:901-904 (2005); Manoharan, *Curr. Opin. Chem. Biol.*, 8:570-579 (2004)).

TABLE 1

Duplex siRNAs with various chemical modifications at the 2' ribose position were synthesized for two siRNA sequences specific for luciferase and GFP.

| Duplex | | Sense | | Antisense | |
|---|---|---|---|---|---|
| Luciferase | GFP | Purine 2' | Pyrimidine 2' | Purine 2' | Pyrimidine 2' |
| L1 | G1 | OH | OH | OH | OH |
| L2 | G2 | OH | F | OH | OH |
| L3 | G3 | H | F | OH | OH |
| L4 | G4 | OH | OH | OH | F |
| L5 | G5 | OH | F | OH | F |
| L6 | G6 | H | F | OH | F |
| L7 | G7 | OH | OH | OMe | F |
| L8 | G8 | OH | F | OMe | F |
| L9 | G9 | H | F | OMe | F |

The antisense luciferase sequence is 5' UAUCUCU-UCAUAGCCUUAUTT 3' (SEQ ID NO:1), the antisense sequence for GFP is 5' UUCACCUUGAUGCCGUUCUTT 3' (SEQ ID NO:2). The 3'-end of the antisense strands in each partially and fully modified siRNA is capped with a single phosphorothioate linkage (TST). The 3' and 5' ends of the sense strand in each partially and fully modified siRNA are capped with 3',3'-inverted deoxy abasic nucleotide linkages (Peracchi et al., *Proc. Natl. Acad. Sci. U.S.A.*, 93:11522-11527 (1996)) (FIG. 1).

The series of synthetically modified duplexes used in these experiments is shown in Table 1, FIG. 1. Luciferase and GFP siRNA duplexes L1-3 and G1-3, respectively, contain an unmodified antisense strand paired with an unmodified (L1 and G1) to fully modified sense strand (L3 and G3). Duplexes L4-6 and G4-6 contain a partially modified antisense strand (2'-F py, 2'-OH pu) paired with an unmodified (L4 and G4) to fully modified (L6 and G6) sense strand. Duplexes L7-9 and G7-9 contain a fully modified antisense strand (2'-F py, 2'OMe pu) paired with an unmodified (L7 and G7) to fully modified (L9 and G9) sense strand. Significantly, duplexes L9 and G9 contain no 2'-OH residues.

Figure 1B:
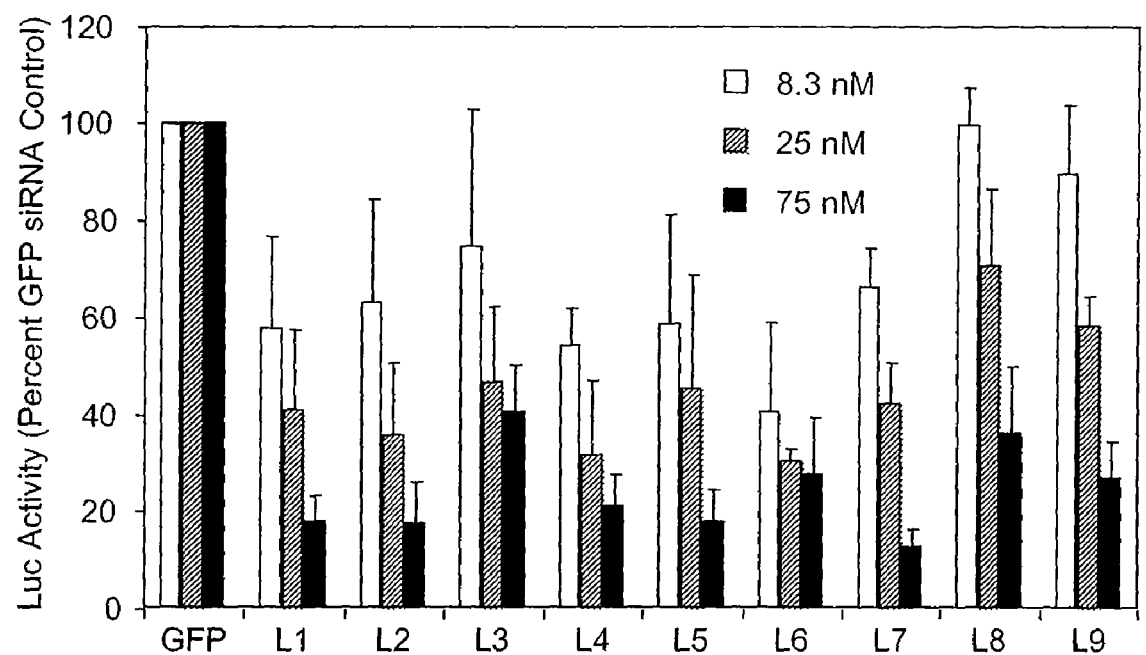

The ability of these variously modified siRNAs to reduce expression of the luciferase gene in a stably transfected cell culture system was examined. These modified duplexes varied no more than 3-fold in potency ($IC_{50}$ ranged from 10 to 30 nM), suggesting that 2' ribose modifications do not necessarily have a significant effect on the ability to silence gene expression (FIG. 1b).

Figure 2A:
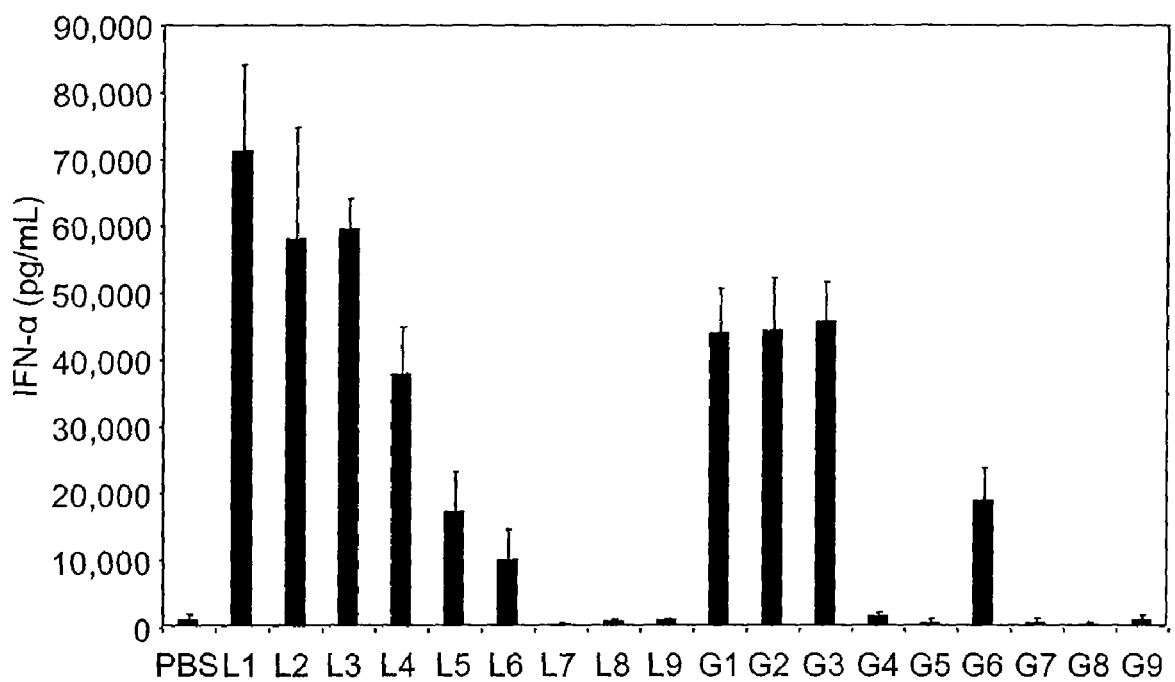
FIG. 2 illustrates data demonstrating that modification of siRNA chemistry ameliorates cytokine induction in mice. ICR mice were treated with a single intravenous administration of 80 μg (~3 mg/kg) lipid-encapsulated siRNA targeting luciferase (L) or green fluorescent protein (G). Serum was recovered 6 hours after treatment. (a) Serum IFN-α levels. (b) Serum IL-6 levels. (c) Serum TNF-a levels. (d) Time-course of cytokine induction. Serum was recovered 2, 6, 12, and 24 hours after treatment. Treatment with empty liposomes or naked siRNA alone induced no detectable cytokine response. Each value is the mean+SD (n=4 mice).

Chemical modification abrogates siRNA mediated immune stimulation in mice. The panel of siRNA duplexes (Table 1) was tested for their ability to elicit a cytokine response in mice. To achieve effective systemic delivery of siRNA in vivo, the siRNA was encapsulated within a liposomal carrier (Jeffs et al., *Pharm. Res.*, 22:362-372 (2005)). The resulting 100-120 nm diameter lipid particles protect the encapsulated siRNA from nuclease degradation, exhibit extended blood circulation times compared to naked siRNA, and are effective at mediating RNA interference (Judge et al., supra). Intravenous administration of lipid-encapsulated unmodified L1 or G1 siRNA induced a significant IFN-α response in outbred ICR mice (FIG. 2a). IFN-α induction by unmodified siRNA was also associated with concurrent production of the inflammatory cytokines interleukin-6 (IL-6) (FIG. 2b) and tumor necrosis alpha (TNF-α) (FIG. 2c). Cytokine induction required the siRNA to be associated with a delivery vehicle since naked siRNA induced no detectable increase in IFN-α or inflammatory cytokines.

Figure 2B:
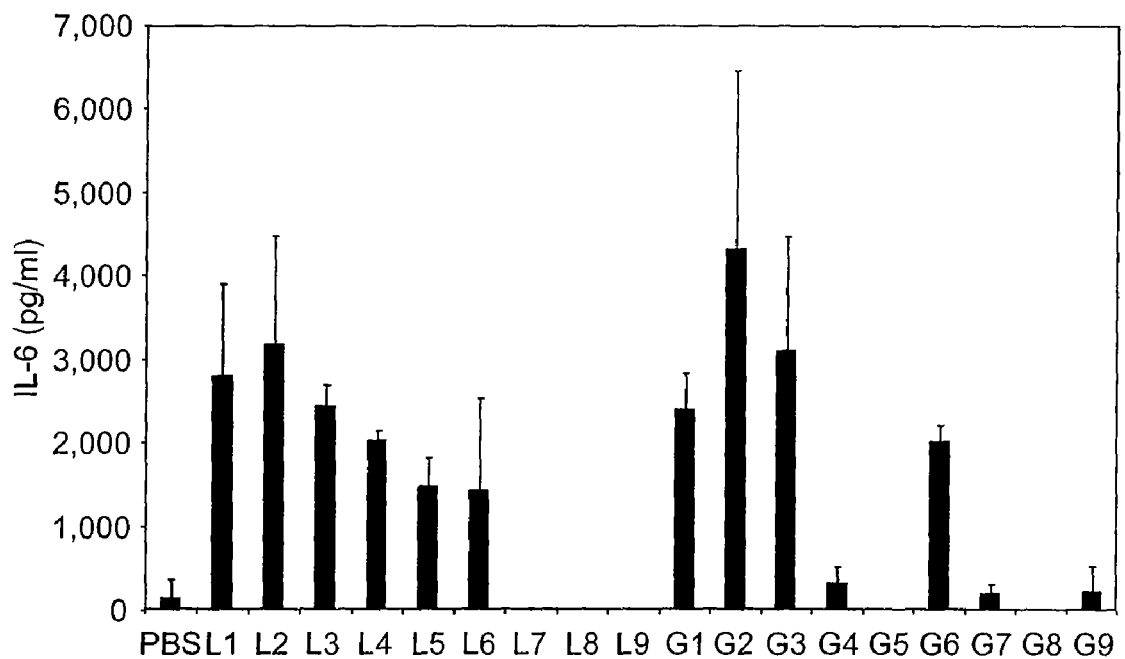
Figure 2C:
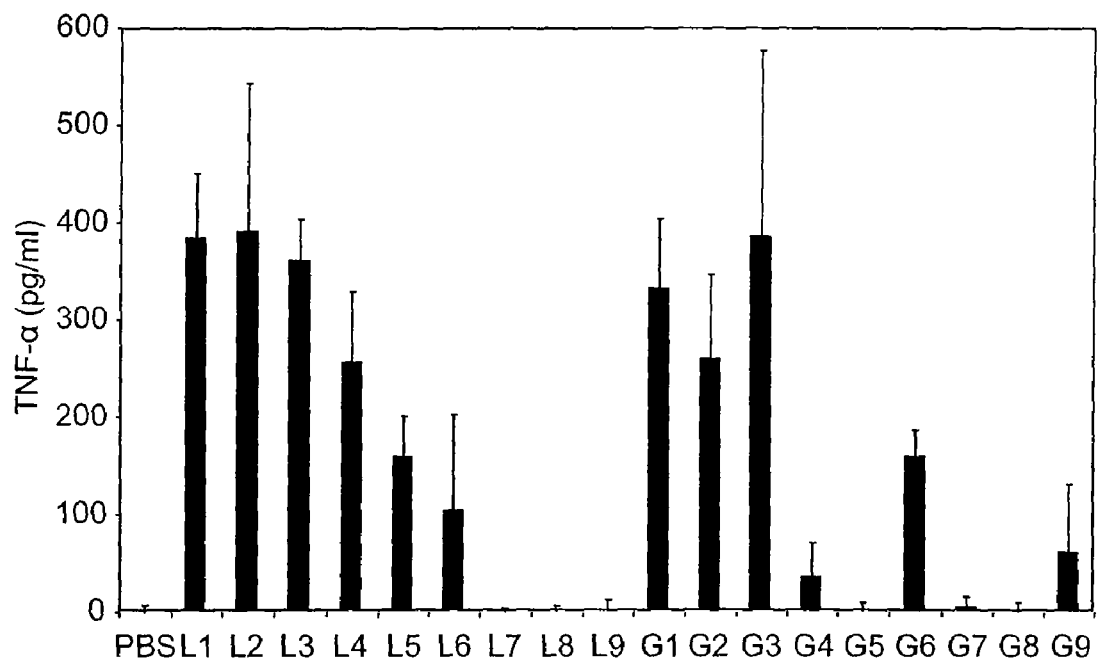

Strikingly, treatment with modified siRNAs, for example, duplexes L7-L9 and G7-G9, induced little or no cytokine responses in mice even when administered in lipid-encapsulated form (FIG. 2a-c). Since each series of chemically modified synthetic siRNA duplexes have the same sequence, this observation demonstrates that the immunostimulatory activity of an siRNA duplex can be modulated by alteration of the 2' ribose position.

Figure 2D:
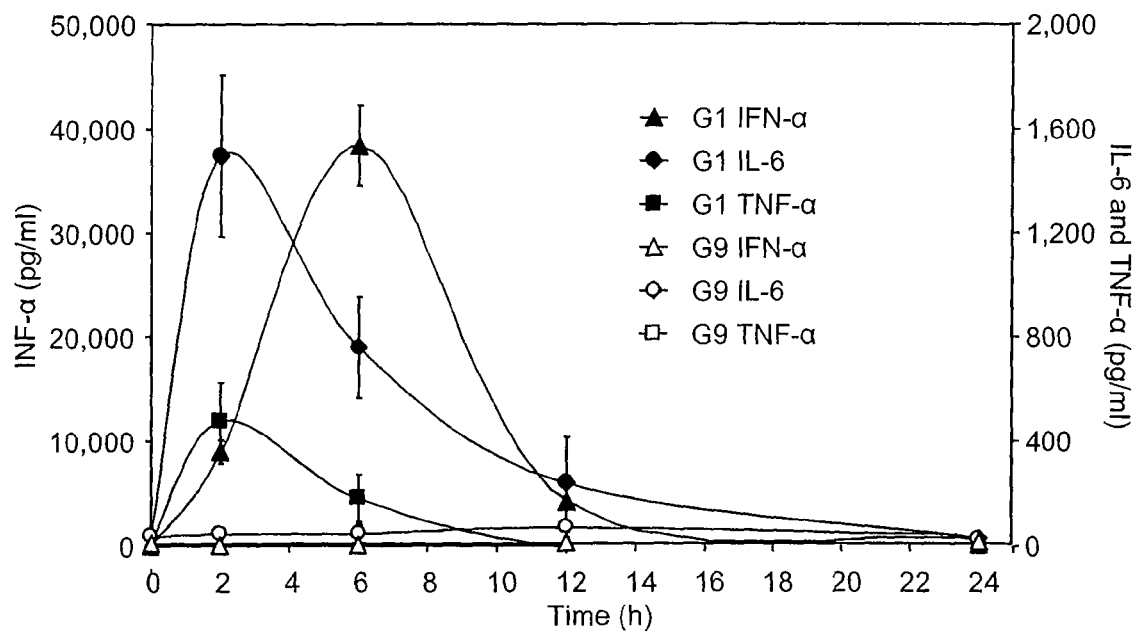

To more thoroughly examine the temporal characteristics of interferon and cytokine induction, mice were treated with the stimulatory duplex G1 and the stimulation pattern was compared to that exhibited by the non-stimulatory duplex G9 (FIG. 2d). The results confirm the findings illustrated in FIGS. 2a-c; duplex G9 has little or no immunostimulatory activity at any of the time-points examined. Duplex G1 showed strong IFN-α induction with maximal activity observed six hours after siRNA administration, while the inflammatory cytokines IL-6 and TNF-α were induced more rapidly with maximal levels observed two hours after administration of stimulatory siRNA. All cytokines returned to background levels within 24 hours.

Figure 3A:
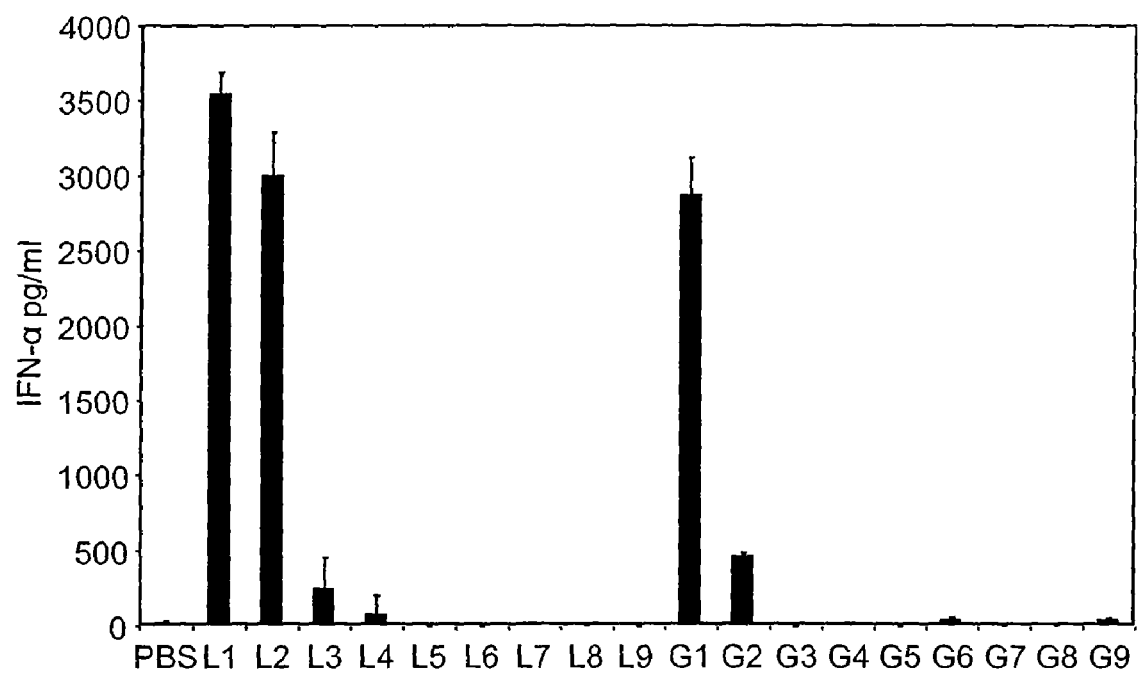
FIG. 3 illustrates data demonstrating that modification of siRNA chemistry ameliorates cytokine production by human PBMC. IFN-α and TNF-α production by human PBMC was determined after overnight stimulation with 1 μg/ml (~75 nM) lipid-encapsulated siRNA targeting luciferase (L) or green fluorescent protein (G). (a) IFN-α levels. (b) TNF-α levels. Empty liposomes and naked siRNA induced no detectable cytokines. Values are mean+/−SD of triplicate cultures.
Figure 3B:
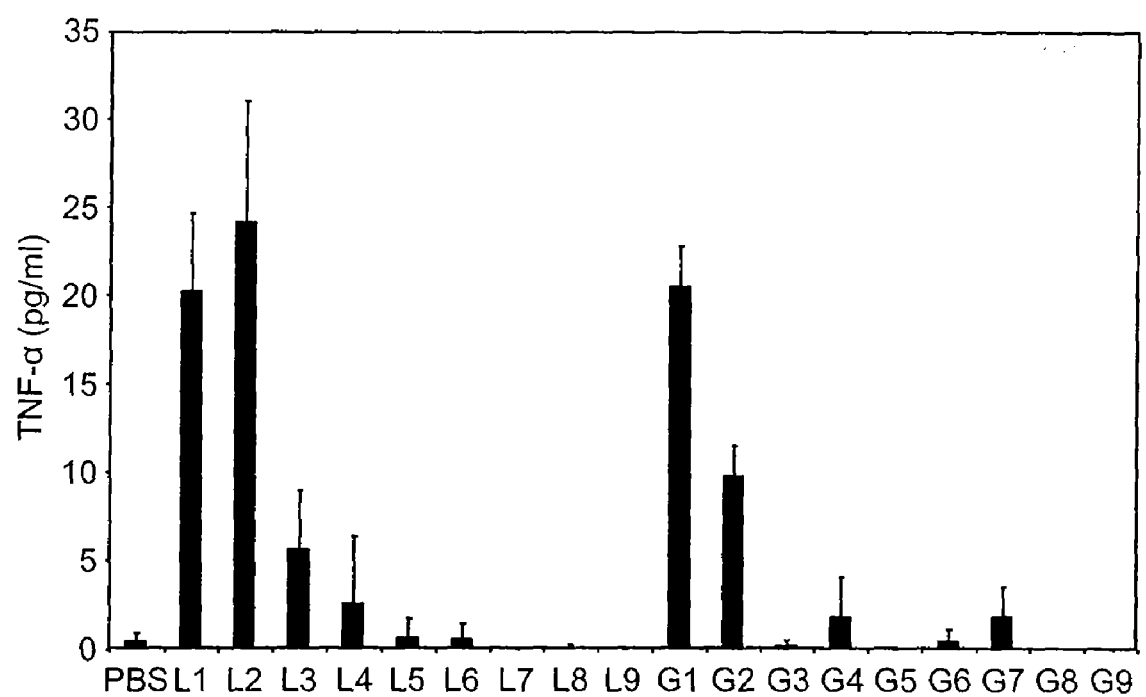

Chemical modification abrogates siRNA mediated immune stimulation in human PBMC. To determine if the relationship between chemical modification and immunostimulatory activity is conserved in a human system, human peripheral blood mononuclear cells (PBMC) were cultured in the presence of the same panel of chemically modified, lipid-encapsulated siRNA. Unmodified siRNA that were immunostimulatory in the mouse have been shown to induce significant IFN-α and inflammatory cytokine release from human PBMC when associated with delivery vehicles (Judge et al., supra). This indicated that the mechanism controlling the inflammatory response to siRNA may be broadly conserved within mammals. Consistent with these findings, FIGS. 3a and 3b show that the unmodified duplexes L1 and G1 are also potent stimulators of both IFN-α and inflammatory cytokines from human PBMC. In contrast, treatment with modified siRNA duplexes, for example, duplexes L7-L9 and G7-G9, yielded no detectable cytokine responses in human PBMC (FIGS. 3a and 3b). These results indicate that the immunostimulatory activity of these siRNAs in human immune cells is also modulated by the 2' ribose chemistry. The induction of both IFN-α and inflammatory cytokines is more readily abrogated by chemical modification in human PBMCs than in the mouse in vivo. Duplexes L3 and G3, both potent inducers in mice, exhibit dramatically attenuated activity in human PBMC. This behavior may reflect either a more stringent stimulation mechanism in human cells, or may reflect the role of innate cofactors that facilitate immune cell activation in vivo. These findings confirm that siRNA duplexes can activate the human innate immune response in an in vitro culture system and that partial chemical modification can significantly alter the immune stimulatory activity of an otherwise active siRNA duplex.

Figure 4A:
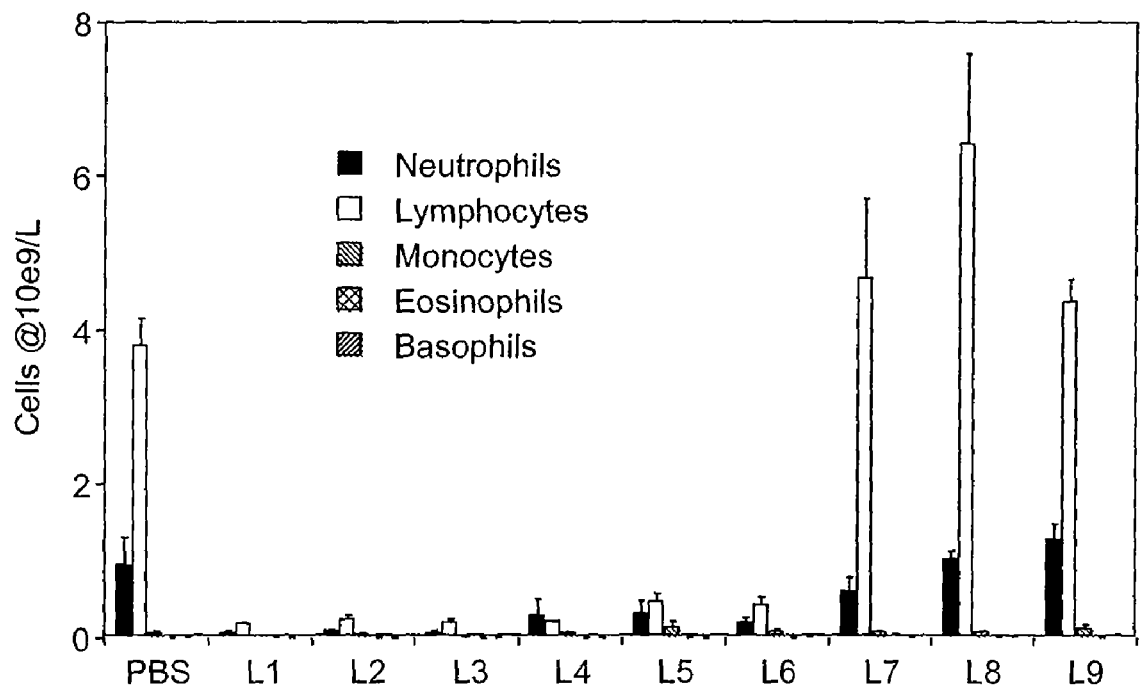
FIG. 4 illustrates data demonstrating that modification of siRNA chemistry ameliorates single dose toxicity in mice. Mice were treated as in FIG. 2. Blood was recovered 48 hours after treatment and subjected to differential cell counting and clinical chemistry analysis. (a) Peripheral white blood cell counts. (b) Peripheral blood platelet counts. (c) Serum transaminase levels. Each value is the mean+SD (n=3 mice).
Figure 4B:
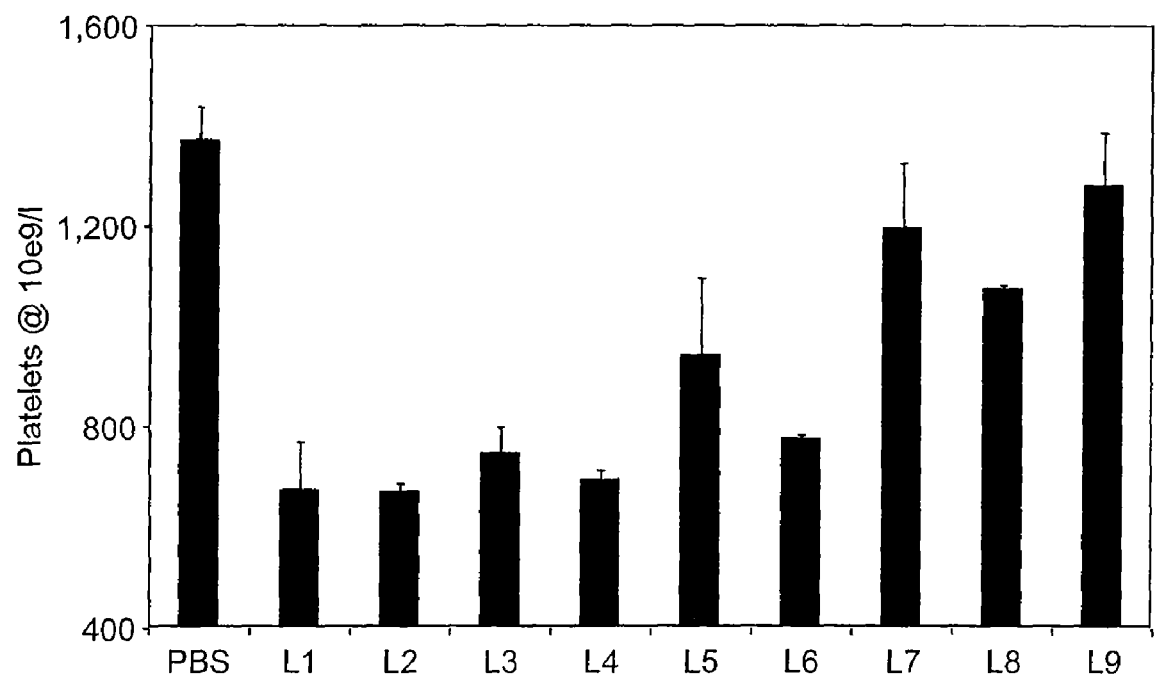
Figure 4C:
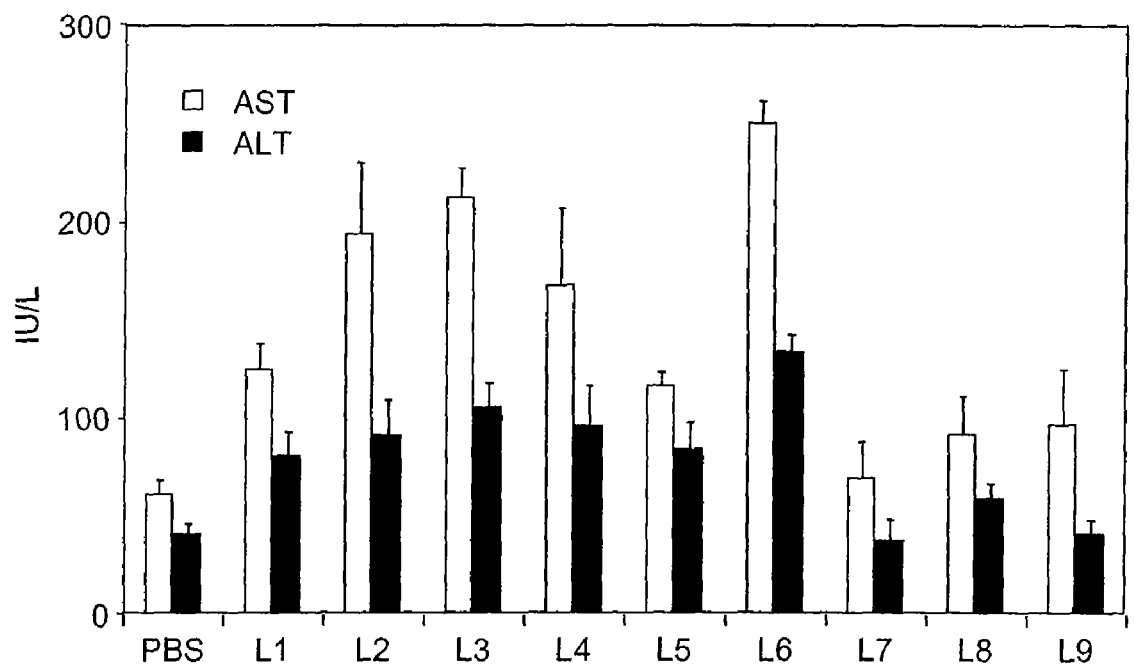

Chemical modifications ameliorate systemic toxicities of synthetic siRNA. Systemic inflammatory reactions are often accompanied by a perturbation of hematological parameters. These effects can include a transient reduction in leukocyte and platelet numbers due to the margination of these cells from the peripheral blood. Intravenous treatment of mice with lipid-encapsulated, immunostimulatory L1-L6 siRNA (see, FIG. 2), resulted in a significant, rapid reduction in white blood cells that was attributable to the selective loss of lymphocytes from the peripheral blood (FIG. 4a). Similarly, treatment with the stimulatory duplexes L1-L6 resulted in moderate thrombocytopenia (FIG. 4b). More apparent toxicities were also observed in these mice including body weight loss, hunched posture, and piloerection that were dependent on the encapsulated siRNA and their extent correlated with the degree of cytokine release. In contrast, administration of the modified non-immunostimulatory siRNA duplexes L7-L9 caused no significant change in WBC or platelet number compared with PBS vehicle controls (FIGS. 4a and 4b). Mice were also examined for perturbations in the serum levels of two commonly used indicators of hepatic toxicity, aspartate transaminase (AST) and alanine transaminase (ALT) (FIG. 4c). Treatment of mice with the more stimulatory duplexes L1-L6 resulted in a modest two to three fold elevation of serum transminase levels. Mice treated with the less stimulatory duplexes L7-L9 exhibited transaminase levels that were not significantly different from the untreated control animals.

Figure 5A:
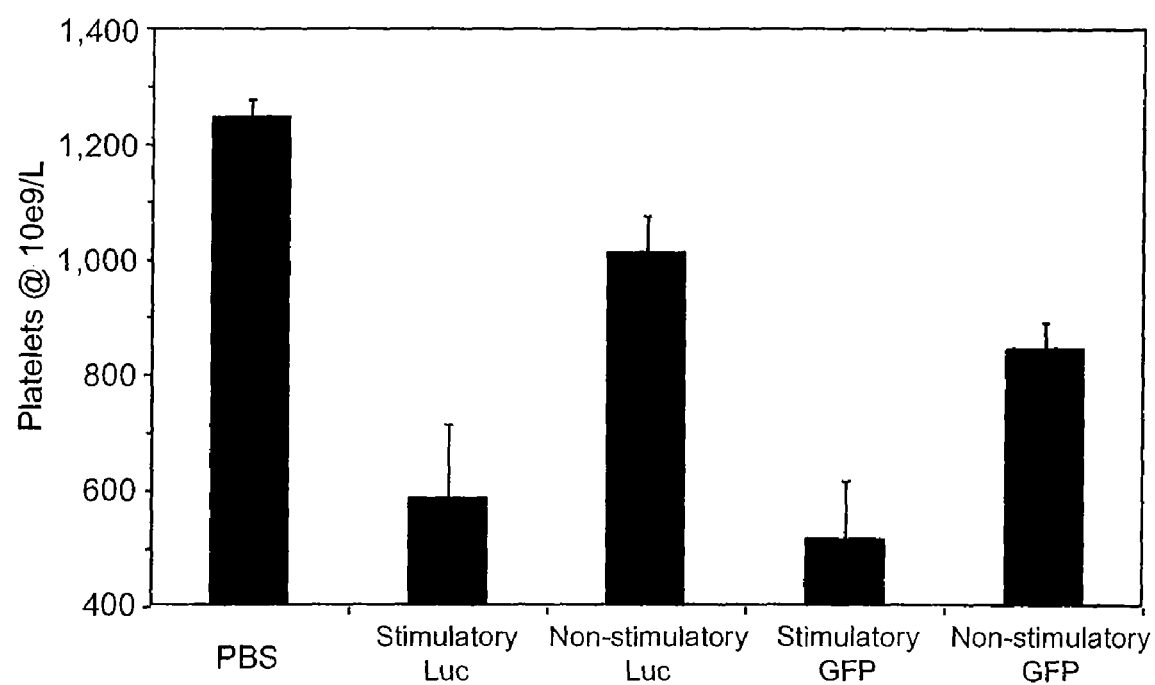
FIG. 5 illustrates data demonstrating that modification of siRNA chemistry ameliorates multi-dose toxicity in mice. ICR mice were treated with three daily intravenous administrations of 80 μg (~3 mg/kg) encapsulated siRNA targeting luciferase (L) or green fluorescent protein (G). Blood was recovered 72 hours after administration of the first treatment and subjected to differential cell counting and clinical chemistry analysis. (a) Peripheral blood platelet counts. (b) Clinical chemistry. Each value is the mean+SD (n=4 mice).
Figure 5B:
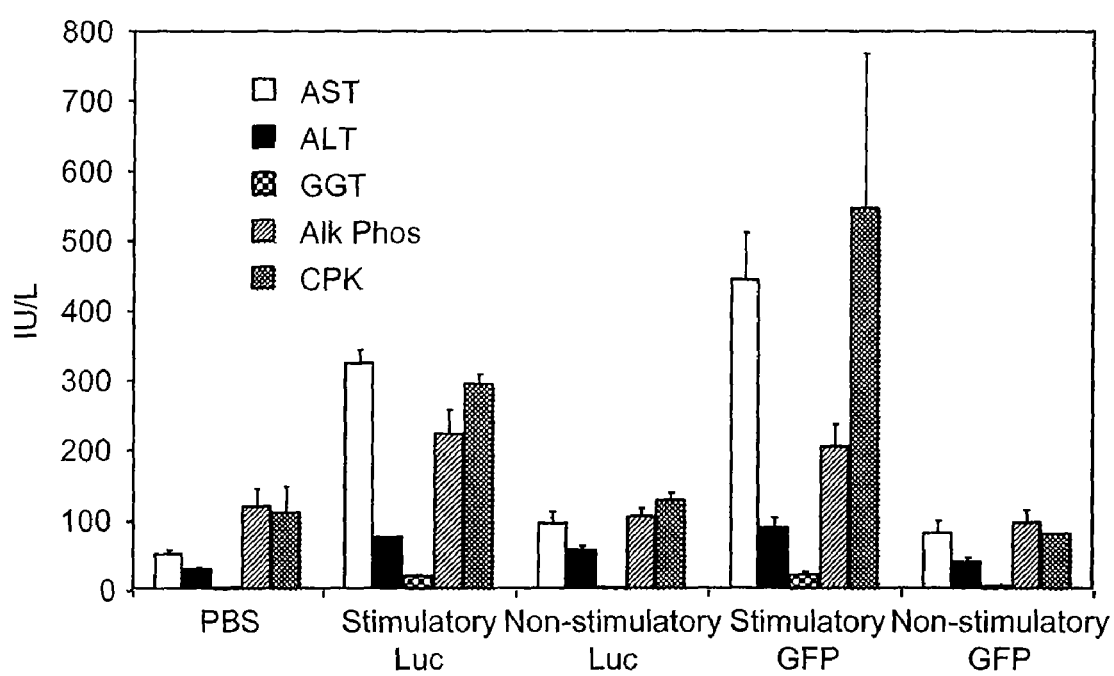

A more rigorous test of the tolerability of modified siRNA is illustrated in FIGS. 5a and 5b. Mice were treated daily with 80 μg (~3 mg/kg) encapsulated siRNA for a period of three days and monitored for signs of toxicity. Treatments consisted of a cocktail of siRNAs that had demonstrated either potent immunostimulatory activity (L1-L3 or G1-G3) or significantly reduced immunostimulatory activity (L7-L9 or G7-G9). Mice that were treated with the immunostimulatory siRNAs exhibited significant weight loss over a period of three days. Treatment with the stimulatory luciferase siRNAs resulted in a loss of −10.7+/−1.3% of initial body weight, while treatment with the stimulatory GFP siRNAs resulted in loss of −11.1+/−3.1% of initial body weight. Treatment with cocktails of the less stimulatory duplexes did not result in any significant reduction in body weight (luciferase, −0.4+/−2.1%; GFP, +3.8+/−3.1%; PBS, +4.1+/−3.4%).

Blood was collected on day three and examined for changes in hematological parameters. Significant platelet reduction persists in mice subjected to sustained treatment with immunostimulatory siRNA (FIG. 5a), while mice that were treated with the less stimulatory siRNA cocktails exhibit less platelet reduction. The relationship between immunostimulation and other clinical toxicities is examined further in FIG. 5b. Serum levels of the enzymes AST, ALT, gamma glutyl transferase (GGT), alkaline phosphatase (Alk Phos), and creatinine phosphokinase (CPK) were determined after three days of siRNA treatment. Treatment with stimulatory siRNA cocktails resulted in elevation of each of these parameters, while no significant elevation was observed after treatment with non-stimulatory duplexes.

Discussion

This example demonstrates that the immunostimulatory activity of synthetic siRNA duplexes can be abrogated through modification of siRNA ribonucleotides. This example also shows that the abrogation of the immunostimulatory activity of siRNA has a profound effect on the tolerability of siRNA treatment in vivo. Importantly, chemical modification of siRNA is readily accomplished in a manner that retains silencing activity.

The relationship between chemical modification and the extent of immune stimulation by siRNA was determined. In the in vivo mouse model, modification of all 2' ribose positions in the targeting anti-sense strand of the luciferase or GFP siRNAs (duplexes L7-9, G7-9) completely abrogated cytokine induction and accompanying toxicities. Conversely, Luc and GFP siRNA containing a non-modified antisense strand (L1-3, G1-3) retained their full capacity to activate the innate immune response. Partial modification of the antisense strand with 2' fluoro-pyrimidines (L4-6, G4-6) had differential effects depending on the siRNA and the degree of sense strand modification. For L4-6, cytokine induction progressively decreased as modification to the sense strand increased. For the GFP series, partial modification of the antisense strand in itself was sufficient to achieve almost complete cytokine inhibition (G4 and G5). However, this inhibitory effect was substantially negated in duplex G6. The sense strand of G6, in contrast to G4 and G5, is predominately 2'-deoxy purines. This DNA-like character may result in helical parameter changes that promote the exposure of immunostimulatory motifs within the duplex. Taken together, these findings imply that the mechanism responsible for eliciting the immune response to siRNA requires the canonical RNA structure imparted by the ribose sugars to be at least partially intact. This contrasts directly with the RNAi machinery which is able to process even fully modified synthetic siRNA duplexes (FIG. 1b). Due to the sequence dependent nature of the response, the extent and location of chemical modifications required to fully abrogate the immunostimulatory properties of siRNA will likely differ according to the sequence of individual siRNA duplexes.

The results described herein have implications for the design of siRNA studies in general. Induction of innate immune function should be routinely monitored, especially when unmodified siRNA is used. Chemical modification of siRNA may obviate the need to avoid sequence motifs, for example, GU rich regions, associated with potent induction of innate immunity. These modifications should minimize immunotoxicities and off target silencing effects that will otherwise hamper the development of this novel class of therapeutic agent.

Methods siRNA synthesis. All RNAs were synthesized by standard procedures (Wincott et al., *Nucleic Acids Res.*, 23:2677-84. (1995)). Annealing was carried out in PBS.

Lipid encapsulation of siRNA. siRNA was encapsulated into liposomes with a lipid composition of DSPC:Chol:PEG-C-DMA:DLinDMA (20:48:2:30 molar percent; Judge et al., supra). For in vitro RNAi experiments, siRNA was complexed with Oligofectamine (Invitrogen; Carlsbad, Calif.) according to the manufacturer's instructions.

Mice. 6-8 week old CD1 ICR mice were obtained from Harlan (Indianapolis, Ind.). siRNA and lipid formulations were administered as an intravenous injection in the lateral tail vein in 0.2 ml phosphate buffered saline (PBS) over a period of 3-5 seconds. Blood was collected by cardiac puncture and processed as plasma for cytokine analysis.

PBMC isolation and culture. Human PBMC were isolated from whole blood obtained from healthy donors. For stimulation assays, $2\times10^5$ freshly isolated cells were seeded in triplicate in 96 well plates and cultured in RPMI 1640 medium with 10% FBS, 2 mM glutamine, 100 U/mL penicillin, and 100 µg/mL streptomycin. siRNA was liposome encapsulated then added to cells at the indicated final nucleic acid concentration. Culture supernatants were collected after 16-20 h and assayed for IFN-α, IL-6, and TNF-α by sandwich ELISA. These assays were mouse and human interferon-α (PBL Biomedical; Piscataway, N.J.), human IL-6 and TNF-α (eBioscience; San Diego, Calif.), and mouse IL-6 and TNF-α (BD Biosciences; San Diego, Calif.).

Example 2

Design of Non-Inflammatory Synthetic siRNA Mediating Potent Gene Silencing In Vivo This example illustrates that minimal 2'OMe modifications at selective positions within one strand of the siRNA duplex are sufficient to fully abrogate the immunostimulatory activity of siRNA, irrespective of its sequence. In fact, by restricting chemical modification to the non-targeting sense strand of the siRNA duplex, the immunostimulatory activity of siRNA can be abolished while retaining full RNAi activity.

Results

Figure 6A:
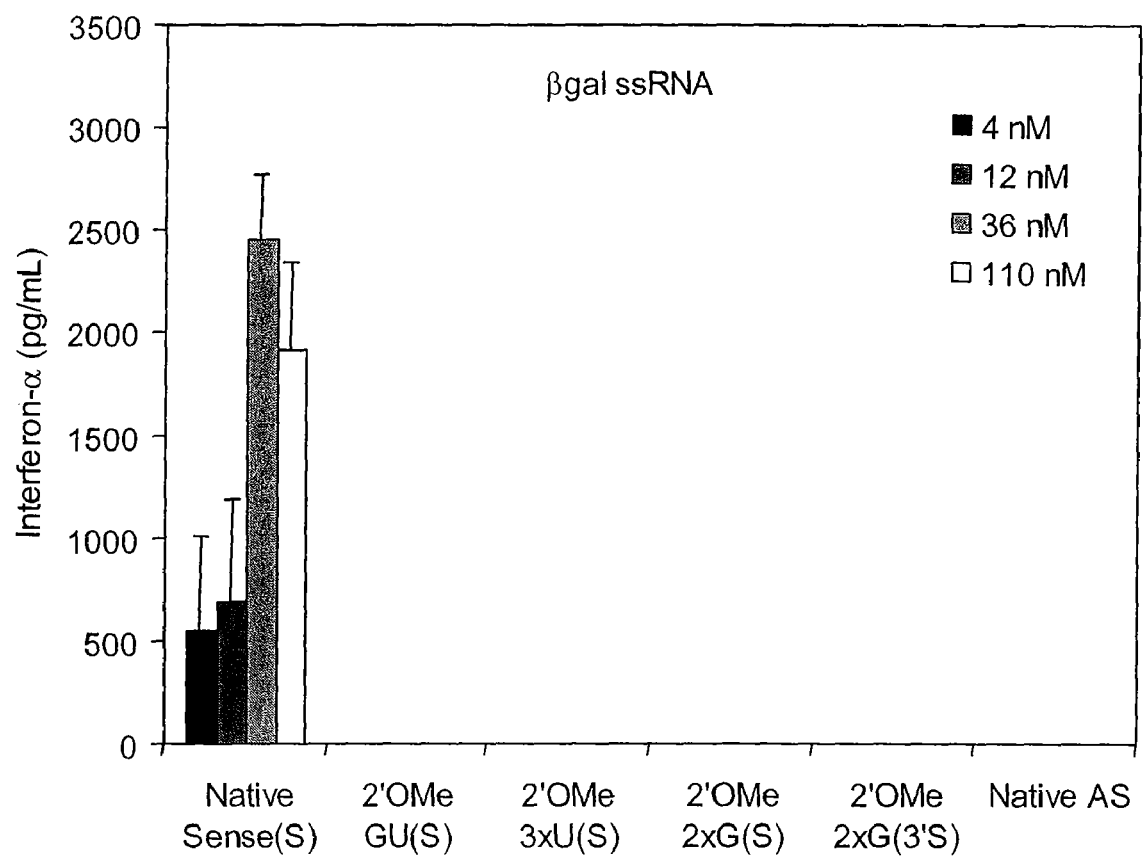
FIG. 6 illustrates data demonstrating that 2'OMe modification abrogates immunostimulatory ssRNA-mediated interferon induction in human PBMC. Liposome encapsulated, unmodified (native) and 2'OMe U, G, or GU modified ssRNA representing the sense (S) or antisense (AS) strands of: (a) βgal and (b) apoB-1 were cultured with PBMC at increasing concentrations (4-110 nM). The ssRNA sequences are detailed in Table 2 below. IFN-α was assayed in culture supernatants at 24 h. Values are mean+SD of triplicate cultures.

2'-O-Methyl Modifications within ssRNA Abrogate Immune Stimulation. To examine the extent and type of chemical modification required to inhibit immune cell activation by RNA, 2'OMe nucleotides were selectively introduced into the GU-rich immunostimulatory motif of a single-stranded RNA oligonucleotide (ssRNA) derived from a β-galactosidase (β-gal) siRNA (Judge et al., *Nat. Biotechnol.*, 23:457-462 (2005)). Oligonucleotide sequences used in these studies are provided in Table 2 below. 2'OMe modification of the 5 nucleotides comprising the immunostimulatory 5'-UGUGU-3' motif (2'OMe GU) in the β-gal sense ssRNA completely abrogated interferon-alpha (IFN-α) induction when human peripheral blood mononuclear cell cultures (PBMC) were treated with lipid encapsulated ssRNA (FIG. 6a). Inhibition of the interferon response was also achieved by selectively modifying either the two guanosine (2'OMe 2×G) or the three uridine (2'OMe 3×U) nucleotides within the motif. The inhibitory effect of 2'-O-methylation however did not appear to require the direct modification of the nucleotides within the immunostimulatory GU rich motif since selective modification of the two guanosine residues 3' to the UGUGU motif, towards the end of the β-gal ssRNA (2'OMe 2×G 3'), also resulted in complete abrogation of the interferon response in PBMC cultures (FIG. 6a). As described previously, the unmodified complementary antisense (AS) ssRNA sequence was inherently non-immunostimulatory in these assays (Judge et al., supra).

Table 2. Unmodified (native) and 2'-O-methyl modified (2'OMe) RNA oligonucleotides corresponding to the sense (S) and antisense (AS) strands of β-gal, apoB-1, apoB mismatch, and vFLIP siRNA. 2'OMe modified nucleotides are underlined; italics represent nucleotide substitutions between apoB-1 and apoB mismatch; and asterisks represent 5' phosphates.

| Name | Strand | Sequence | SEQ ID NO: |
|---|---|---|---|
| β-gal | Native (S) | | |
| | 2'OMe GU (S) | UUGA<u>UGUGU</u>UUAGUCGCUAUU | 4 |
| | 2'OMe 3 × U (S) | UUGA<u>U</u>G<u>U</u>G<u>U</u>UUAGUCGCUAUU | 5 |
| | 2'OMe 2 × G (S) | UUGAU<u>G</u>U<u>G</u>UUUAGUCGCUAUU | 6 |
| | 2'OMe 2 × G 3' (S) | UUGAUGUGUUUA<u>G</u>UC<u>G</u>CUAUU | 7 |

-continued

| Name | Strand | | SEQ ID NO: |
|------|--------|---|------------|
| | Native (AS)* | *U A G C G A C U A A A C A U-C A A U U | 8 |
| | 2'OMe AC (AS) | *U A G C G A C U A A A C A U C A A U U | 9 |
| apoB-1 | Native (S) | G U C A U C A C A C U G A A U A C-C A A U | 10 |
| | 2'OMe U (S) | G U C A U C A C A C U G A A U A C C A A U | 11 |
| | 2'OMe G (S) | G U C A U C A C A C U G A A U A C C A A U | 12 |
| | 2'OMe C (S) | G U C A U C A C A C U G A A U A C C A A U | 13 |
| | 2'OMe A (S) | G U C A U C A C A C U G A A U A C C A A U | 14 |
| | Native (AS) | *A U U G G U A U U C A G U G U G A U G A-C A C | 15 |
| | 2'OMe GU (AS) | *A U U G G U A U U C A G U G U G A U G A C A C | 16 |
| | 2'OMe U (AS) | *A U U G G U A U U C A G U G U G A U G A C A C | 17 |
| | 2'OMe G (AS) | *A U U G G U A U U C A G U G U G A U G A C A C | 18 |
| apoB mismatch | Native (S) | G U G A U C A G A C U C A A U A C-G A A U | 19 |
| | 2'OMe U (S) | G U G A U C A G A C U C A A U A C G A A U | 20 |
| | Native (AS) | *A U U C G U A U U G A G U C U G A U C A-C A C | 21 |
| | 2'OMeGU (AS) | *A U U C G U A U U G A G U C U G A U C A C A C | 22 |
| vFLIP | Native (S) | G U G G U A U U G U U C C U C-C U A A dT dT | 23 |
| | 2'OMe GU (S) | G U G G U A U U G U U C C U C C U A A dT dT | 24 |
| | 2'OMe U (S) | G U G G U A U U G U U C C U C C U A A dT dT | 25 |
| | Native (AS) | *U U A G G A G G A A C A A U A C-C A C dT dT | 26 |
| | 2'OMe U (AS) | *U U A G G A G G A A C A A U A C C A C dT dT | 27 |
| | 2'OMe C (AS) | *U U A G G A G G A A C A A U A C C A C dT dT | 28 |

Figure 6B:
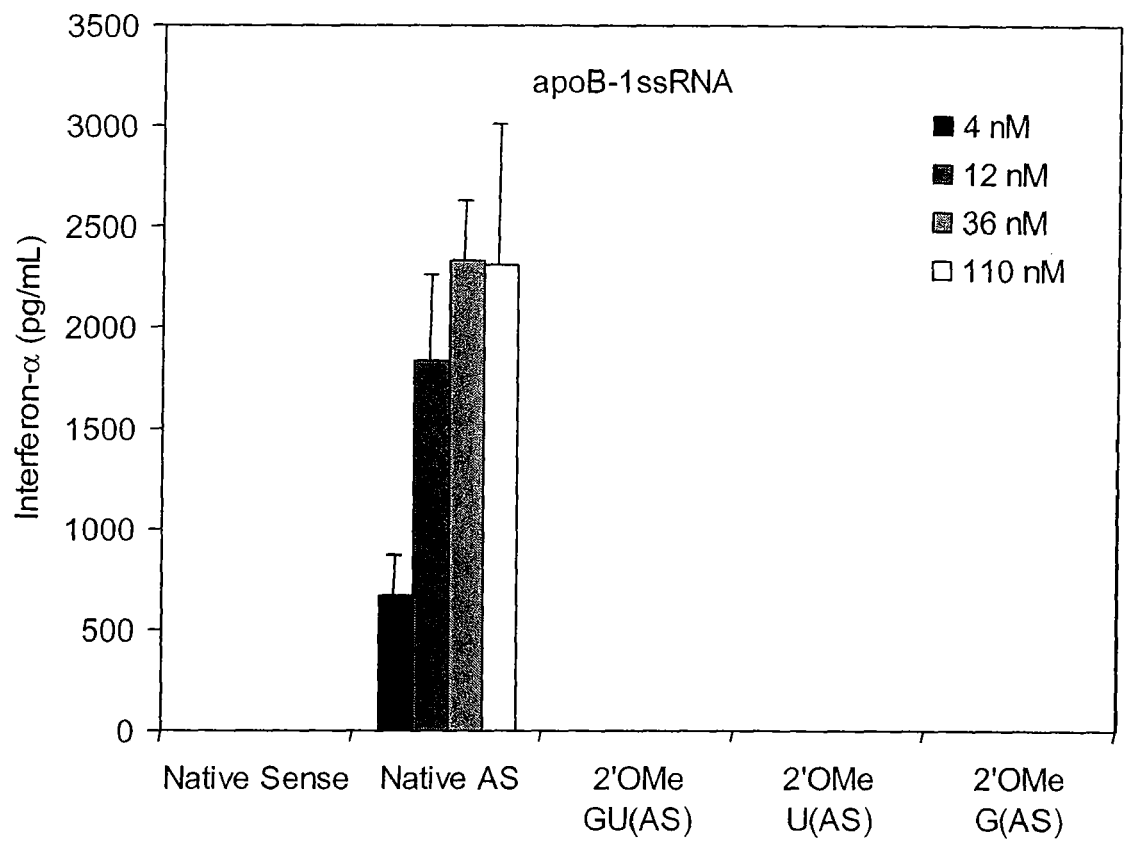

A similar approach was applied to the modification of the constituent 21 and 23 base strands of an siRNA duplex targeting human and mouse apoB (apoB-1 siRNA) (Soutschek et al., Nature 432:173-178 (2004)). As predicted by its GU rich nucleotide sequence (Heil et al., Science 303: 1526-1529 (2004); Judge et al., supra), unmodified apoB-1 (AS) ssRNA stimulated a strong IFN-α response in PBMC cultures, even at low concentrations (FIG. 6b). This response was fully inhibited by 2'OMe modification of either the 5 nucleotides comprising the 5'-GUGUG-3' motif (2'OMe GU) or the 6 guanosine (2'OMe G) or 7 uridine (2'OMe U) residues in apoB-1(AS) ssRNA (FIG. 6b). The unmodified, complementary apoB-1 sense oligonucleotide (apoB-1(S)) encapsulated in lipid particles did not induce IFN-α in PBMC (FIG. 6b), although high doses of this oligonucleotide delivered as PEI polyplexes was found to activate a cytokine response. This weak response to PEI-complexed apoB-1(S) ssRNA was also inhibited by 2'OMe-uridine modification. These findings demonstrate that the selective incorporation of 2'OMe modified nucleotides within ssRNA is sufficient to prevent stimulation of the interferon response from innate immune cells.

Figure 7A:
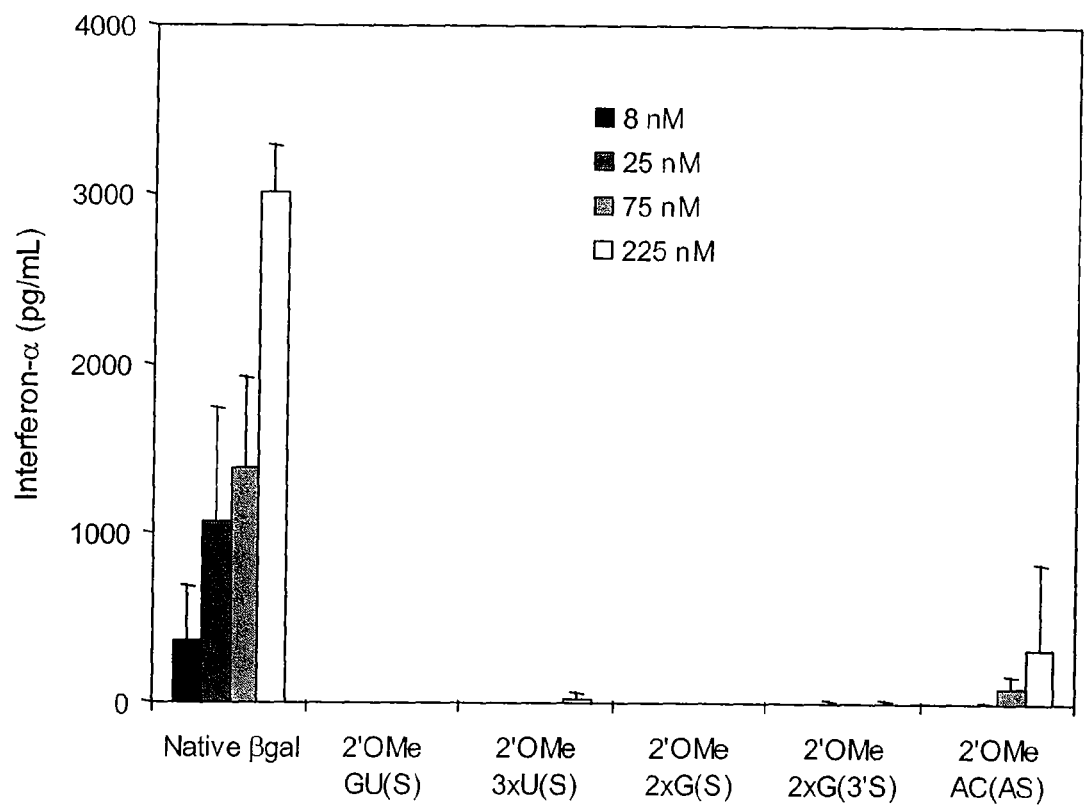
FIG. 7 illustrates data demonstrating that selective 2'OMe modification to siRNA duplexes abrogates cytokine induction in human PBMC. (a), (b) IFN-α and (c) TNF-α induction from human PBMC cultured with increasing concentrations (25-675 nM) of encapsulated (a) βgal or (b), (c) apoB-1 or apoB mismatch siRNA. Cytokine responses to unmodified (native) siRNAs were compared to duplexes containing 2'OMe U, G, C, or A residues in either the sense (S) or antisense (AS) strands as indicated (see, Table 2 below for siRNA sequences). Secreted cytokines were assayed after 24 h culture. Values are mean+SD. of triplicate cultures.
Figure 7B:
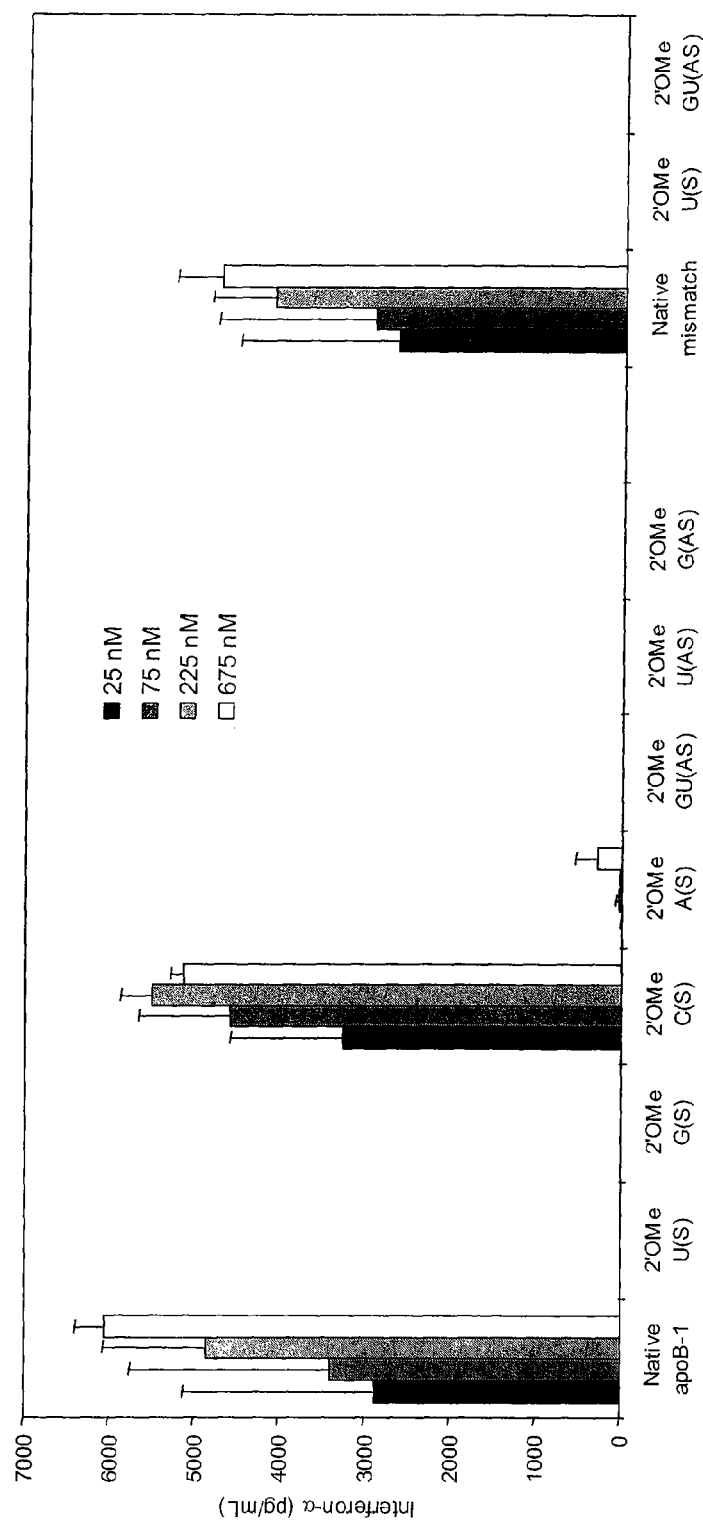
Figure 7C:
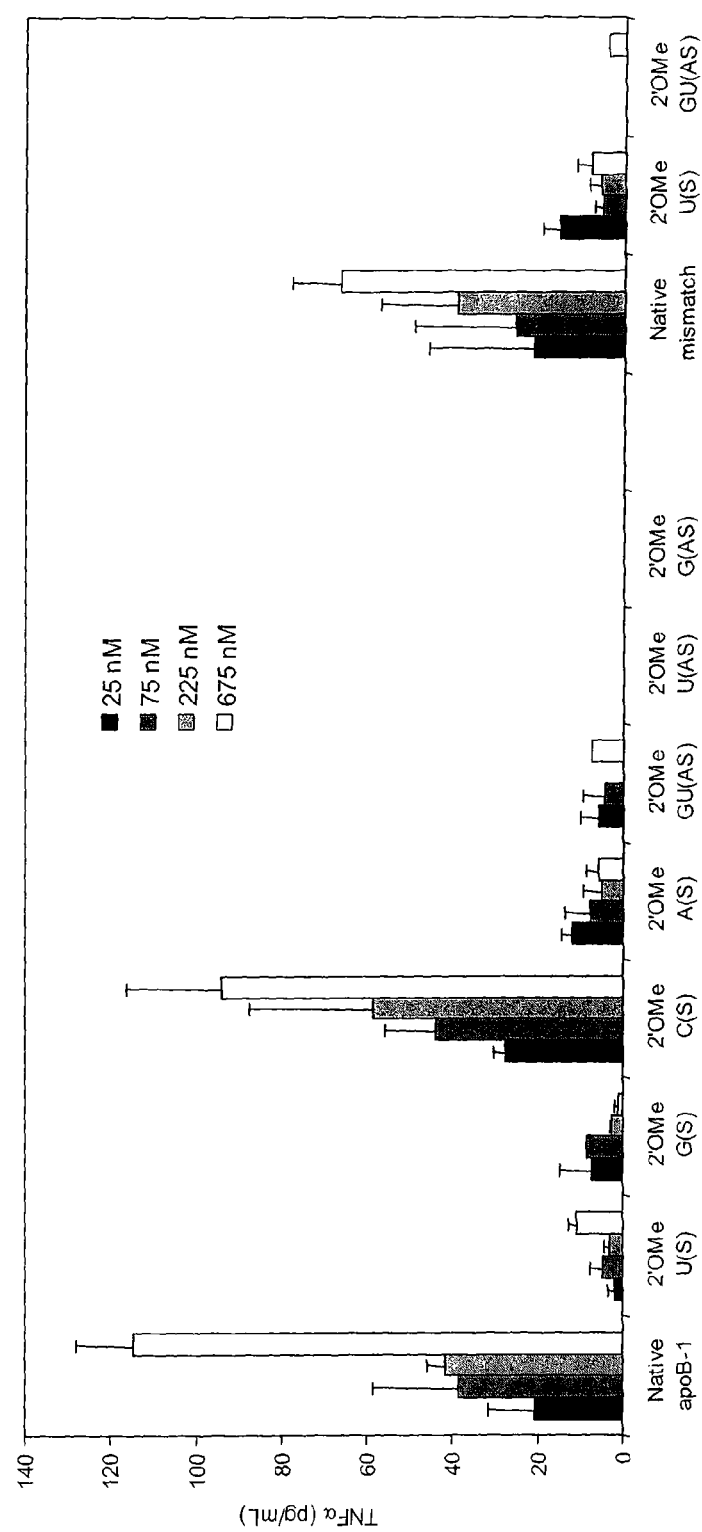

Selective Nucleotide Modifications within siRNA Abrogate Immune Stimulation. To examine whether selective 2'OMe modifications within siRNA duplexes also inhibited immune stimulation, a series of β-gal and apoB-1 siRNA comprising 2'OMe modified sense or AS strands annealed to their complementary unmodified oligonucleotides were generated (see, Table 2). As predicted by results for the constituent ssRNA (see, FIG. 6a), double stranded β-gal siRNA comprising either the 2'OMe modified UGUGU, 2×G, or 3×U sense strand annealed with the unmodified (non-immunostimulatory) AS strand induced no detectable interferon response from human PBMC (FIG. 7a). Interestingly, selective 2'OMe modification of the complementary 5'-ACACA-3' motif in the AS strand, juxtaposed to the unmodified 5'-UGUGU-3' motif in the sense strand, also diminished the level of IFN-α induction despite the annealed duplex containing the unmodified (immunostimulatory) sense strand (FIG. 7a). Similar results were found with modified apoB-1 duplex siRNA (FIG. 7b). Unmodified apoB-1 siRNA induced a strong IFN-α response in PBMC and this reaction was completely abrogated when 2'OMe GU, U, or G modified AS strands were incorporated in the apoB-1 duplex. Strikingly, modified apoB-1 siRNA containing 2'OMe G or U modified sense strands annealed to the unmodified, immunostimulatory, AS strand were also rendered non-immunostimulatory (FIG. 7b). Abrogation of cytokine induction by 2'OMe G or U modifications to the sense strands of modified apoB-1 siRNA appeared absolute, as even high concentrations (675 nM, 9 µg/mL) of modified siRNA failed to induce IFN-α or inflammatory cytokines such as TNF in PBMC cultures (FIGS. 7b and 7c).

The inhibitory effect of 2'-O-methylation on immune stimulation by siRNA was not observed with all patterns of modification, however, as apoB-1 siRNA containing 2'OMe modified cytidine residues induced levels of cytokines similar to those induced by the native duplex (FIG. 7b). The incorporation of 2'OMe adenosine resulted in significant, but not absolute, inhibition of the cytokine response. These differences did not simply reflect the extent of chemical modification, as the 2'OMe G, U, C, and A modified apoB-1 contain 2, 5, 6, and 8 modified nucleotides in the sense strand, respectively. This suggests that unmodified U and/or G residues may play a key role in immune recognition of the duplex siRNA.

Figure 8A:
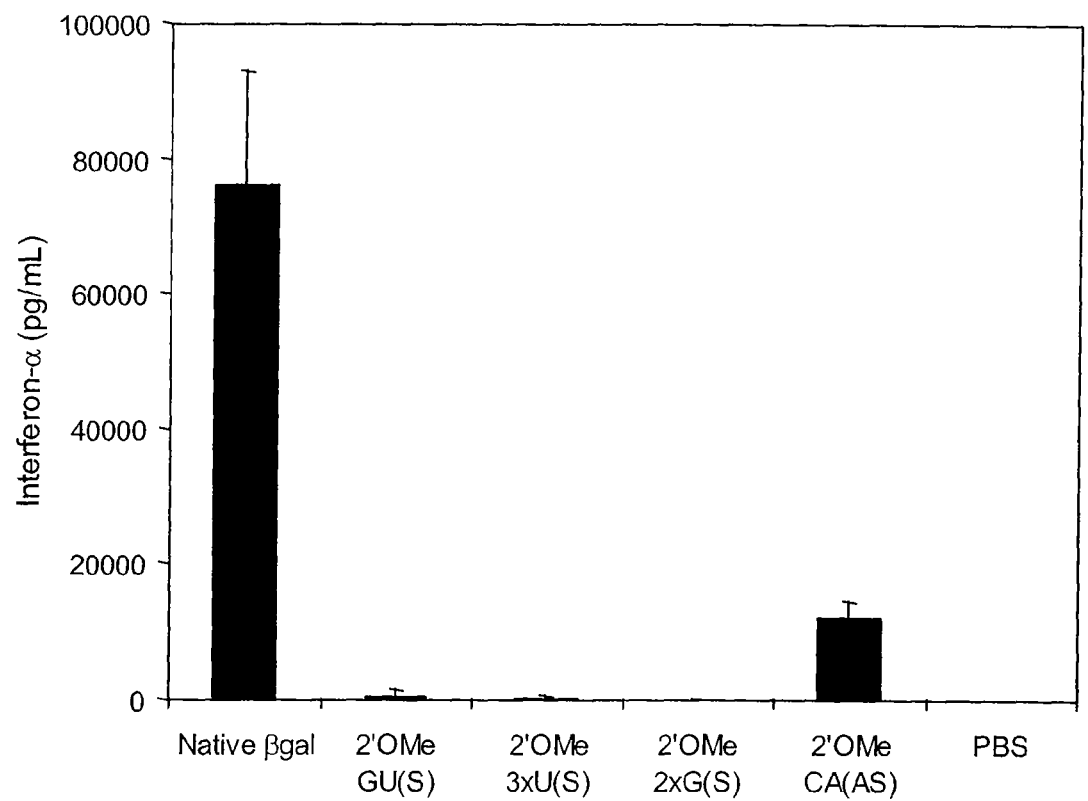
FIG. 8 illustrates data demonstrating that selective 2'OMe modification to siRNA duplexes abrogates cytokine induction in vivo. (a), (c), (e), (f) Serum IFN-α and (b), (d) TNF-α and IL-6 levels 6 h after intravenous administration of encapsulated (a), (b) βgal, (c), (d) apoB-1, (e) apoB mismatch, or (f) vFLIP siRNA. Responses to unmodified (native) siRNAs were compared to duplexes containing 2'OMe U, G, or C residues in either the sense (S) or antisense (AS) strands as indicated (see, Table 2 below for siRNA sequences). All mice received 40 μg encapsulated siRNA. Values are mean+SD from 3-4 animals. Lower levels of quantitation are 75 pg/mL for IFN-α, 30 pg/mL TNF-α, and 60 pg/mL IL-6.
Figure 8B:
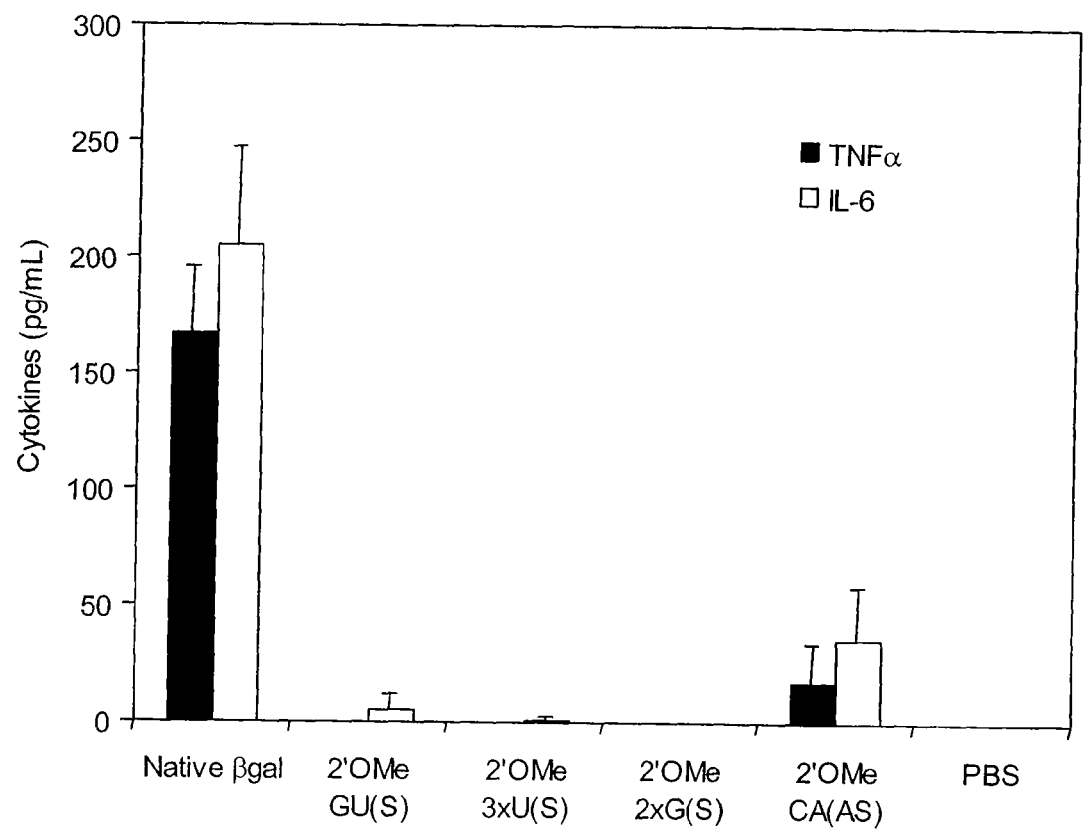
Figure 8C:
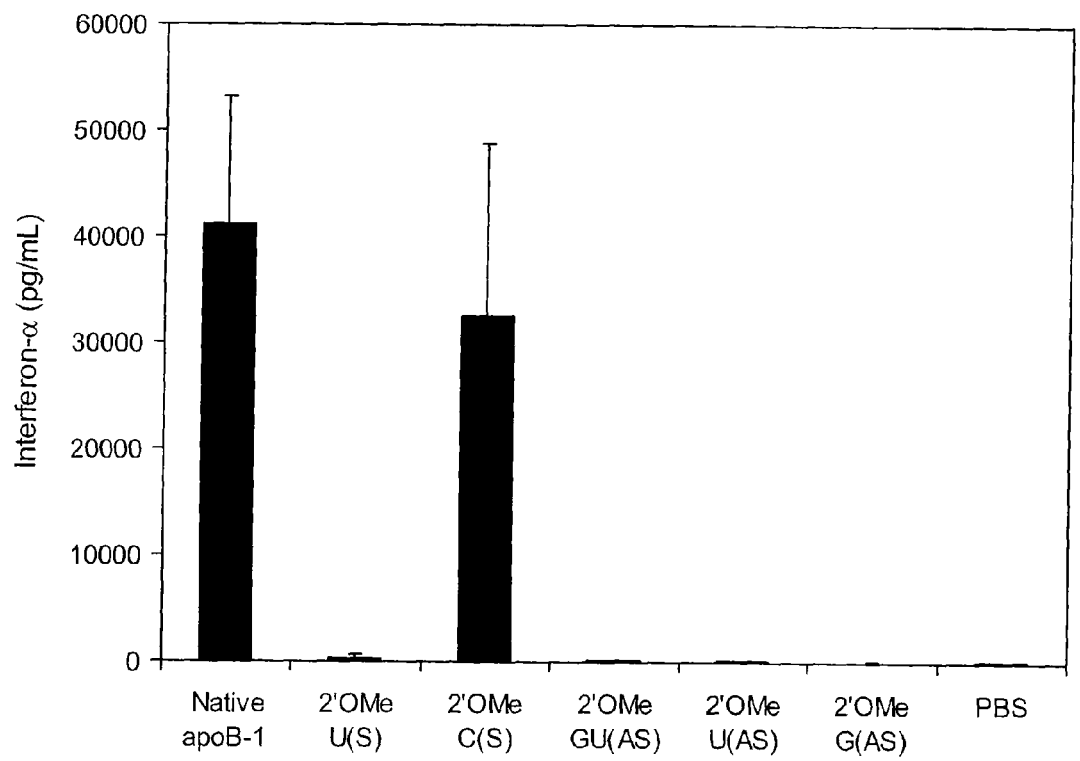
Figure 8D:
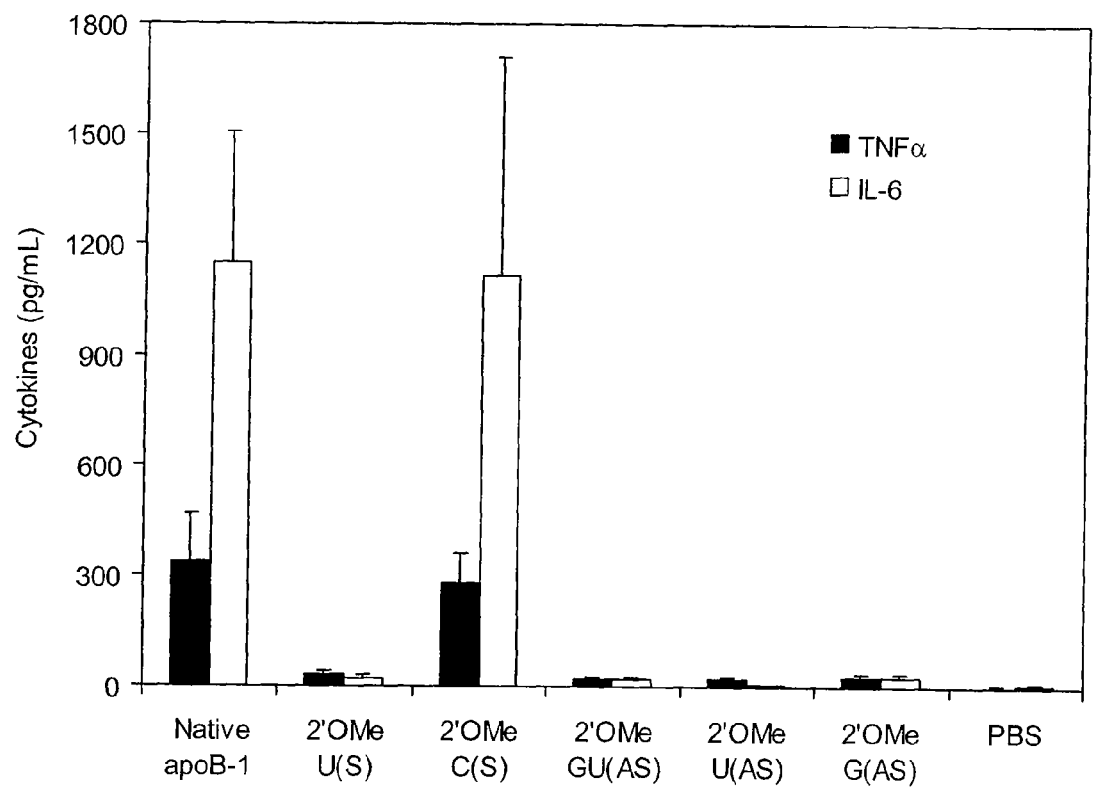
Figure 8E:
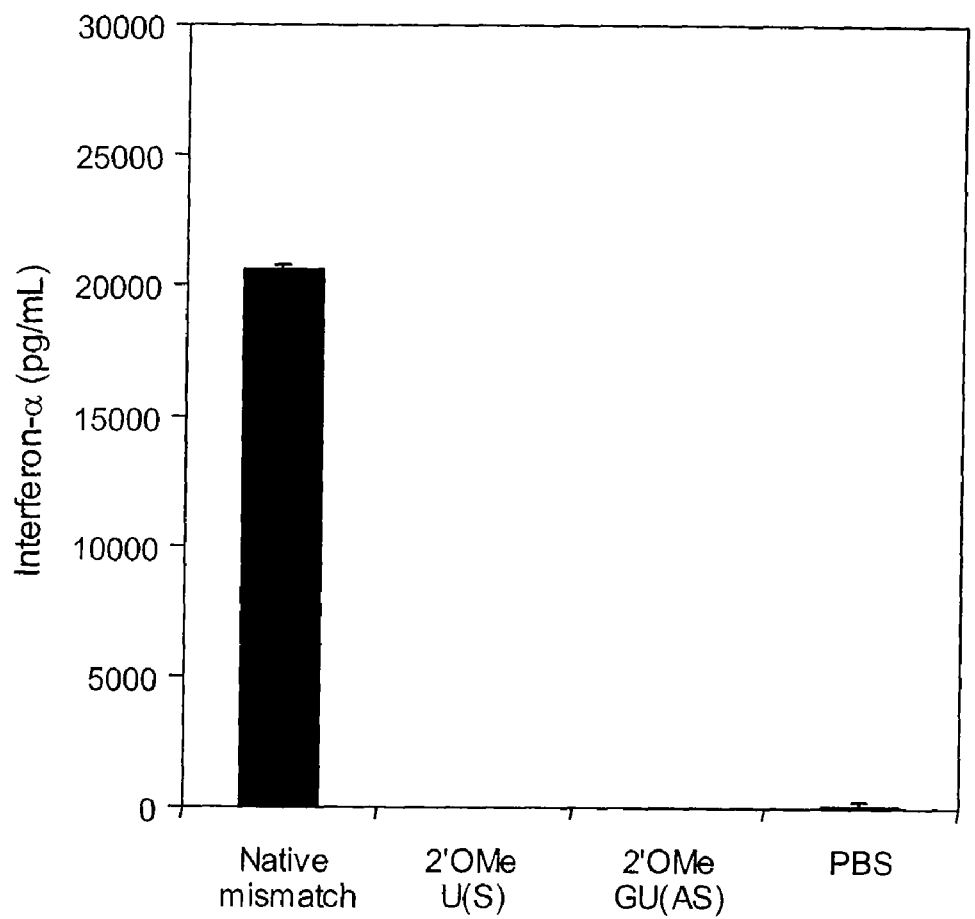
Figure 8F:
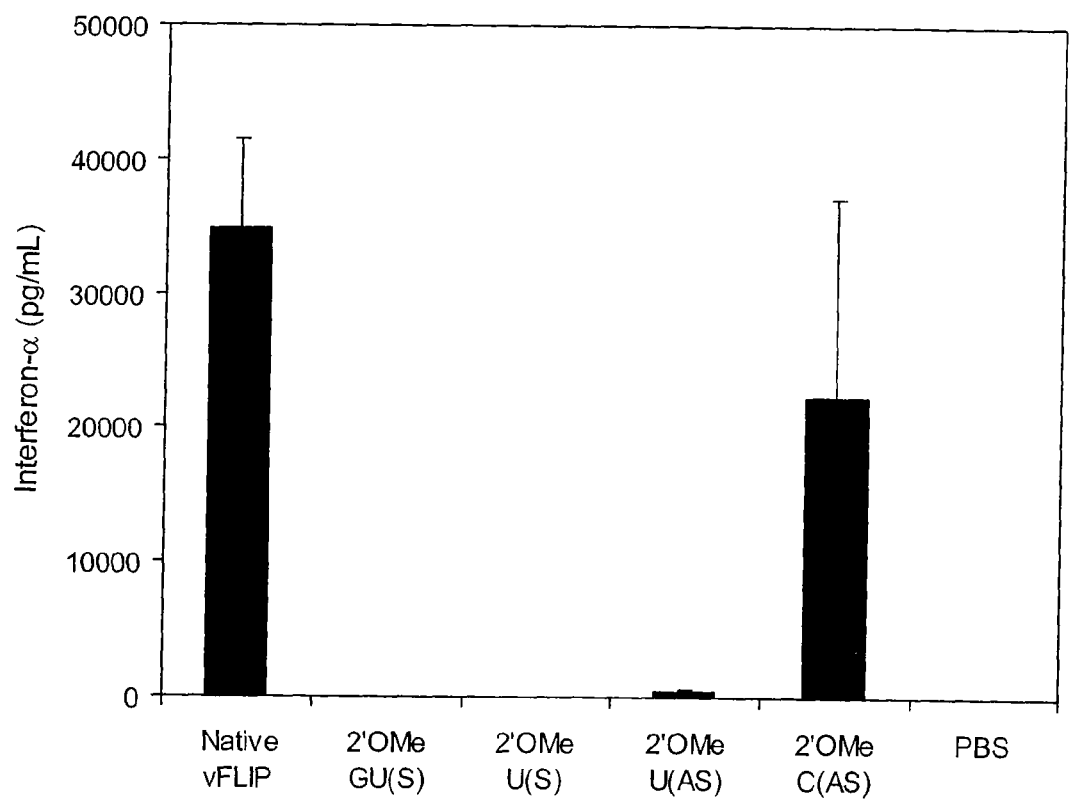

To confirm that this approach to siRNA design would successfully inhibit inflammatory responses to siRNA in vivo, the immunostimulatory activity of the 2'OMe modified β-gal and apoB-1 siRNA were assessed in mice. Intravenous administration of lipid encapsulated β-gal (FIGS. 8a and 8b) or apoB-1 (FIGS. 8c and 8d) siRNA containing 2'OMe modified guanosine or uridine residues in either sense or antisense strands caused no detectable increase in serum IFN-α or inflammatory cytokines such as TNF. This was in marked contrast to the unmodified or cytosine modified siRNAs that induced substantial elevations in the level of these cytokines (FIGS. 8c and 8d). These striking effects of selective 2'OMe modification were confirmed by applying a similar approach to modifying apoB mismatch (Soutschek et al., Nature 432: 173-178 (2004)) and VFLIP (Guasparri et al., J. Exp. Med. 199:993-1003 (2004)) siRNA sequences (see, Table 2). For the apoB mismatch (FIG. 8e) and vFLIP (FIG. 8f) siRNA duplexes, modifying either the GU rich regions or only the uridine residues in either one of the RNA strands completely abrogated cytokine induction by the siRNA duplex. Inhibition of the cytokine response to modified apoB mismatch siRNA was also confirmed in human PBMC cultures (FIGS. 7b and 7c). As with apoB-1, selective incorporation of 2'OMe cytosine residues into vFLIP siRNA did not substantially reduce the IFN-α response (FIG. 8f). Similar results have been consistently achieved with several additional siRNA sequences in which the introduction of 2'OMe-uridine or guanosine residues has generated non-inflammatory siRNA duplexes. Taken together, these findings support the conclusion that the underlying mechanism for immune recognition of short RNA duplexes appears to be largely conserved between mouse and humans (Judge et al., supra; Hornung et al., Nat. Med. 11:263-270 (2005)). These results indicate that this mechanism can be profoundly disrupted in either species by the incorporation of as few as two 2'OMe modified nucleotides within either strand of an siRNA duplex.

Figure 9:
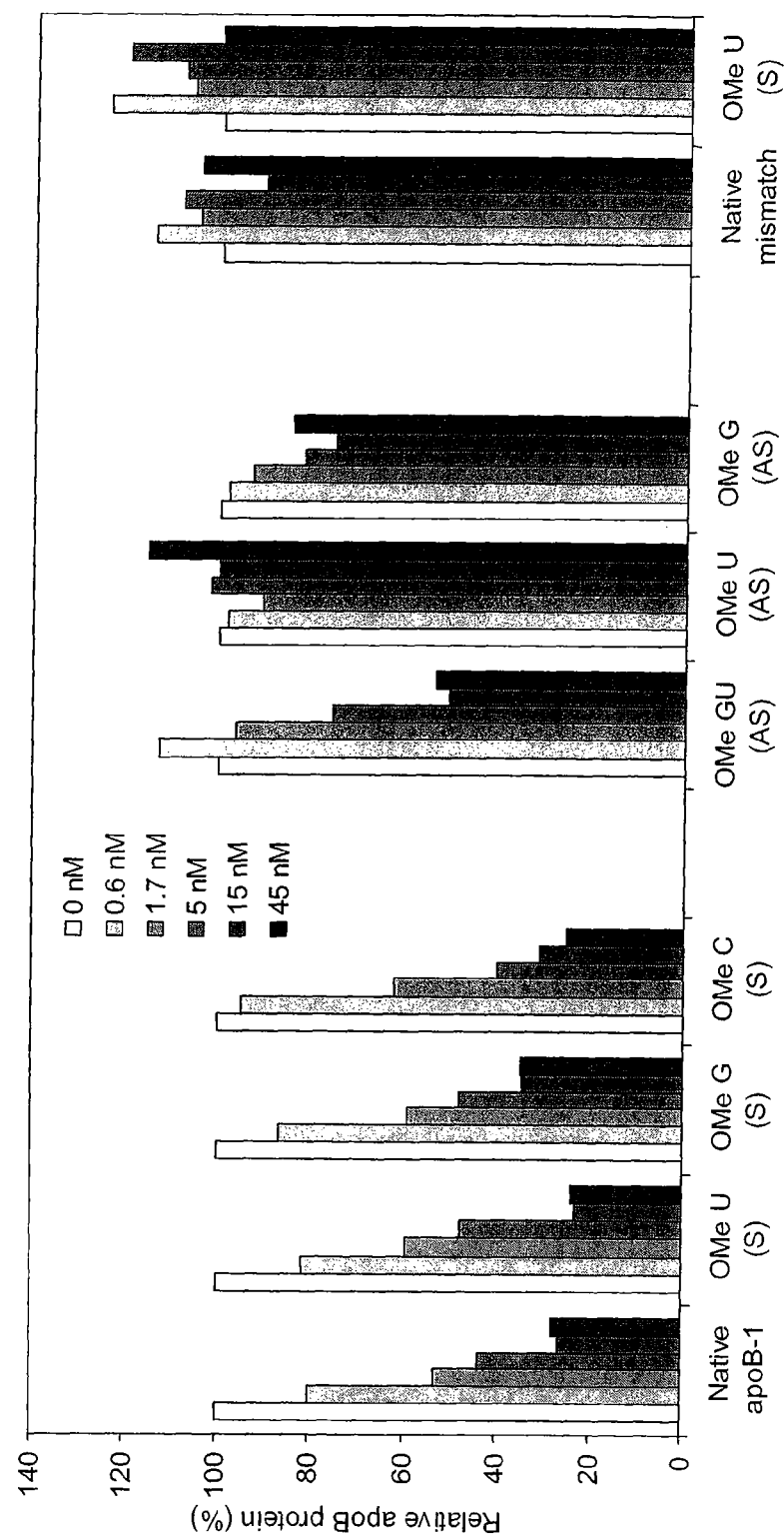
FIG. 9 illustrates data demonstrating in vitro silencing of apoB expression by 2'OMe modified siRNA. HepG2 cells were treated with encapsulated apoB-1 or mismatch siRNA at the indicated concentrations (0-45 nM). Unmodified (native) apoB-1 siRNA was compared to apoB-1 duplexes containing 2'OMe U, G, or C residues in the sense (S) or GU motif, U, or G residues in the antisense (AS) strands as indicated (see, Table 2 below for modified siRNA sequences). Unmodified and 2'OMe U(S) apoB mismatch siRNA served as control duplexes. apoB protein in culture supernatants was measured by ELISA after 48 h. ApoB levels are expressed as % of PBS treated control cultures. Each value was derived from means of duplicate cultures and is representative of 3 separate experiments.

Restricting Modifications to siRNA Sense Strand Maintains RNAi Activity. The gene silencing activity of native and 2'OMe modified apoB-1 siRNAs were assessed in vitro. Unmodified apoB-1 encapsulated within liposomes caused potent, dose-dependent inhibition of apoB protein in HepG2 cell culture supernatants (FIG. 9). Estimated IC50 values (~1.5 nM) were in agreement with those established for this siRNA sequence using Oligofectamine transfection in a similar in vitro model (Soutschek et al., supra). Modified apoB-1 duplexes in which 2'OMe modifications were restricted to the non-targeting sense or passenger strand displayed broadly similar apoB silencing activity to that of the native siRNA (FIG. 9). In contrast, modifications to the targeting antisense (AS) or guide strand severely impacted the RNAi activity of the duplex. Incorporation of 2'OMe uridine or guanosine residues in the AS strand abrogated apoB gene silencing, whereas the duplex containing the 5'-GUGUG-3' modified AS strand displayed substantially reduced activity (estimated IC50=~15 nM) compared to the native or sense modified duplexes. Unmodified or modified apoB mismatch control siRNAs yielded no significant inhibition of apoB protein expression (FIG. 9). The negative impact of AS strand modification on gene silencing activity is consistent with previous work demonstrating that 2'OMe modification of the AS strand of an siRNA duplex, particularly at the 5' end, can reduce RNAi activity (Prakash et al., J. Med. Chem. 48:4247-4253 (2005)). A similar strategy of restricting 2'OMe modifications to the sense strands of β-gal and luciferase siRNAs also proved successful in generating non-inflammatory siRNAs that retained full RNAi activity. These data illustrate that selective 2'OMe modifications, restricted to the sense strand of siRNA, offers a robust approach to overcoming the problem of immune activation by siRNA while minimizing any negative impact on RNAi activity. These results indicate that this approach can be applied to many, if not all, siRNA sequences with inherent capacity to stimulate the innate immune response, encompassing the vast majority of conventionally designed synthetic siRNA.

Figure 10A:
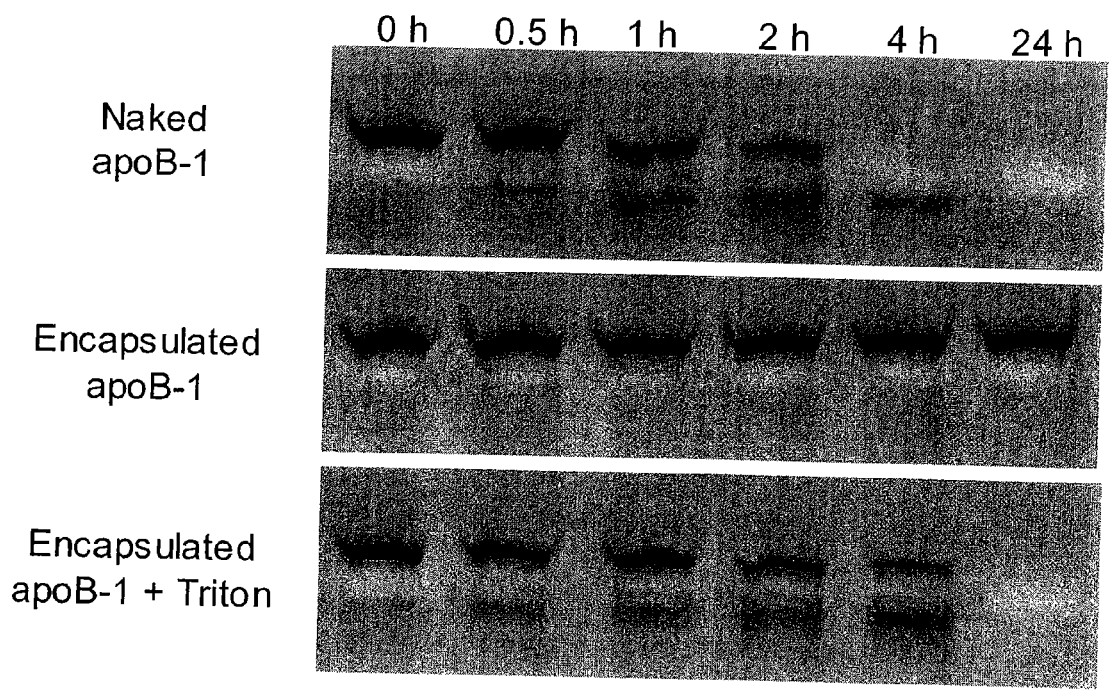
FIG. 10 illustrates data demonstrating silencing of apoB expression in vivo without activation of the innate immune response. (a) Encapsulation of siRNA in lipid particles protects against serum nuclease degradation. Unmodified naked (top) or SNALP encapsulated (middle) apoB-1 siRNA was incubated in 50% mouse serum at 37° C. Duplex integrity was assessed at indicated timepoints by non-denaturing PAGE analysis. Addition of Triton-X to disrupt lipid particle integrity (bottom) restored siRNA nuclease sensitivity. (b)-(f) In vivo effects following intravenous administration of encapsulated apoB-1 or mismatch siRNA in mice. Mice were treated on d 0, 1, and 2 with encapsulated unmodified, 2'OMe U(S), or GU(AS) modified apoB-1, and unmodified or 2'OMe U(S) modified mismatch siRNA at 5 mg/kg per day. (b) Daily changes in body weight (% of d 0 weight) of apoB-1 (solid symbols) and mismatch (open symbols) siRNA treated mice over the 4 day study period. (c) Serum IFN-α from test bleeds 6 h after initial treatment. ND, Not Detected; lower level of quantitation 75 pg/mL. (d) apoB mRNA levels in liver. (e) apoB protein in serum. (f) Serum cholesterol (mM) 2 d after final siRNA treatment. ApoB levels are expressed as % of apoB mRNA or apoB protein compared to PBS treated animals. All values are mean+SD of 5 animals. All data are representative of 2 separate experiments.

Potent RNAi Activity without Immune Stimulation In Vivo. 2'OMe-modified apoB-1 siRNA were assessed for their ability to silence gene expression and immune stimulation in vivo. 2'OMe U(S) and GU(AS) modified apoB-1 were selected as non-inflammatory duplexes (see, FIGS. 7 and 8). This also afforded the opportunity to assess the impact of chemical modifications that reduced in vitro RNAi activity of the AS modified siRNA (see, FIG. 9). Native or 2'OMe modified apoB-1 and mismatch siRNA were formulated in stable nucleic acid-lipid particles (SNALP) previously shown to deliver siRNA to the liver (Morrissey et al., Nat. Biotechnol. 23:1002-1007 (2005)). For use in systemic applications, nucleic acid based drugs require stabilization or protection from nuclease degradation. Encapsulation inside the lipid bilayer protected unmodified and otherwise labile siRNA from serum nuclease degradation for greater than 24 h at 37° C. in vitro, implying that encapsulation offers adequate nuclease protection without the need for extensive chemical modification to the siRNA. By comparison, naked siRNA was fully degraded within 4 h under similar conditions (FIG. 10a).

Figure 10B:
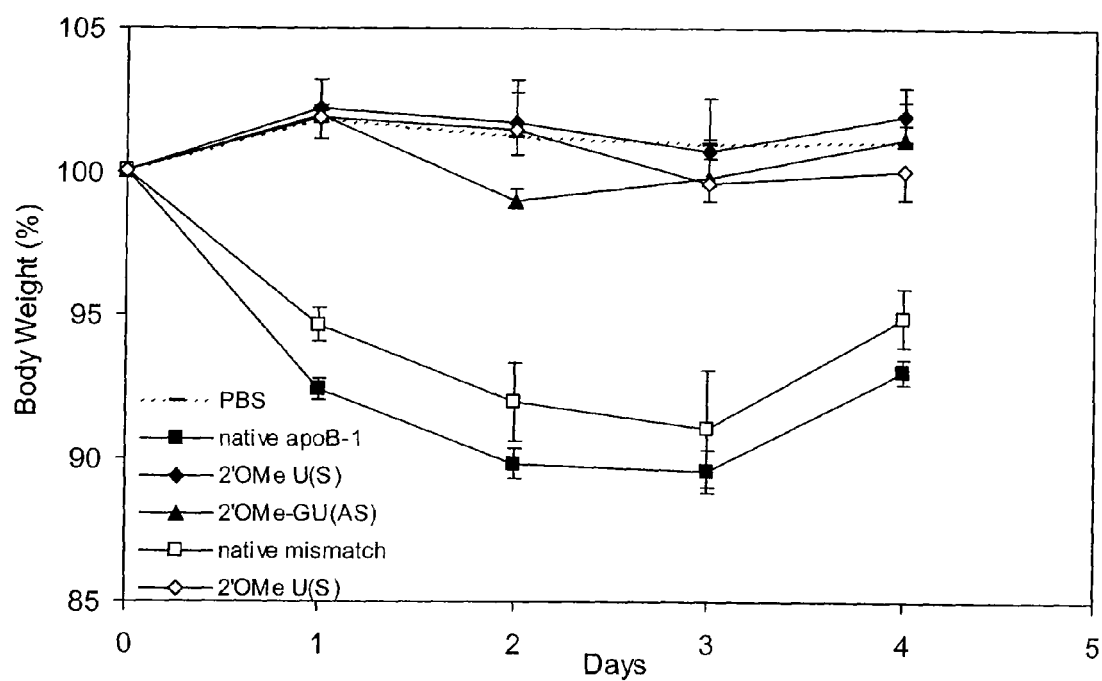
Figure 10C:
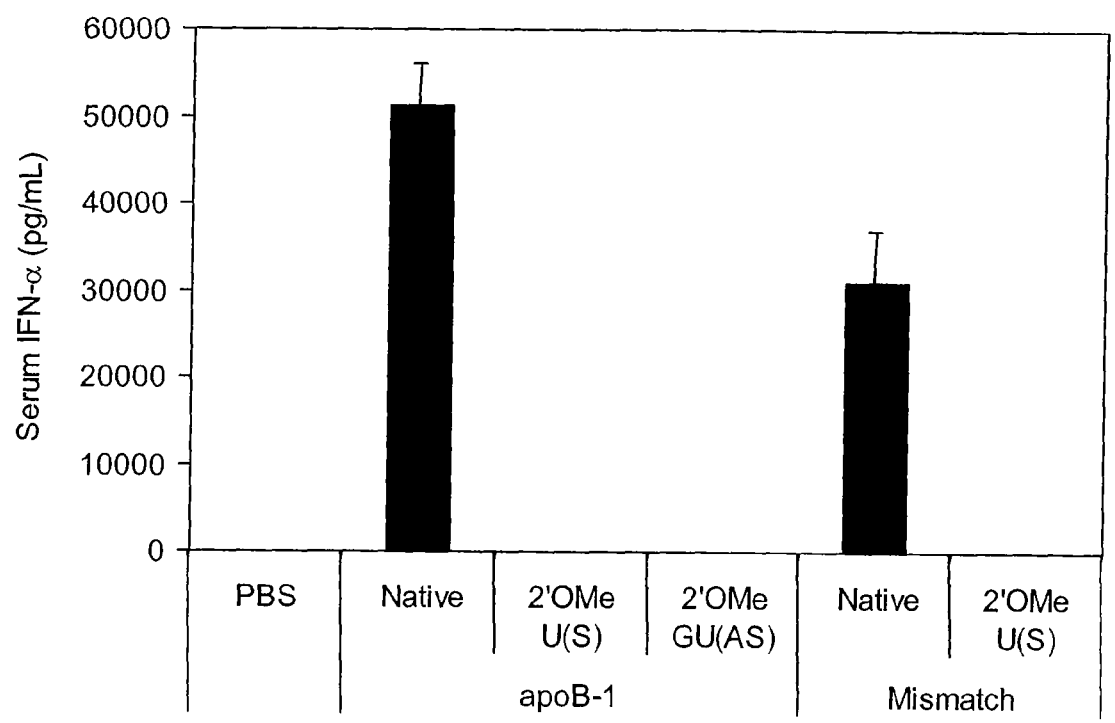

Encapsulated apoB siRNA were administered intravenously to BALB/c mice at 5 mg/kg/day for 3 days. This regimen represents a 10-fold reduction in apoB-1 siRNA dose originally reported to be efficacious in experiments utilizing cholesterol-conjugated, chemically modified apoB-1 siRNA (Soutschek et al., supra). Animals receiving native, immunostimulatory apoB-1 or mismatch siRNAs displayed overt symptoms of toxicity as evidenced by a loss of 10.5% and 9% of initial body weight respectively by day 3 (FIG. 10b) and mild deterioration in general body condition during the course of treatment. In contrast, treatment with the 2'OMe modified siRNAs was well tolerated with minimal (less than 1%) or no body weight loss (FIG. 10b). Abrogation of the innate cytokine response in these efficacy studies was confirmed by in-life serum IFN-α analysis (FIG. 10c), and accordingly the toxicity associated with administration of the unmodified siRNAs was attributed to the systemic cytokine response. Of note, cytokine levels and body weight loss induced by unmodified mismatch siRNA were lower than for the corresponding active apoB-1 duplex. The mismatch control in this case was generated by four G/C substitutions within the apoB-1 sequence (Soutschek et al., supra), providing further evidence for the sequence-dependent effects on immune stimulation by RNA duplexes.

Figure 10D:
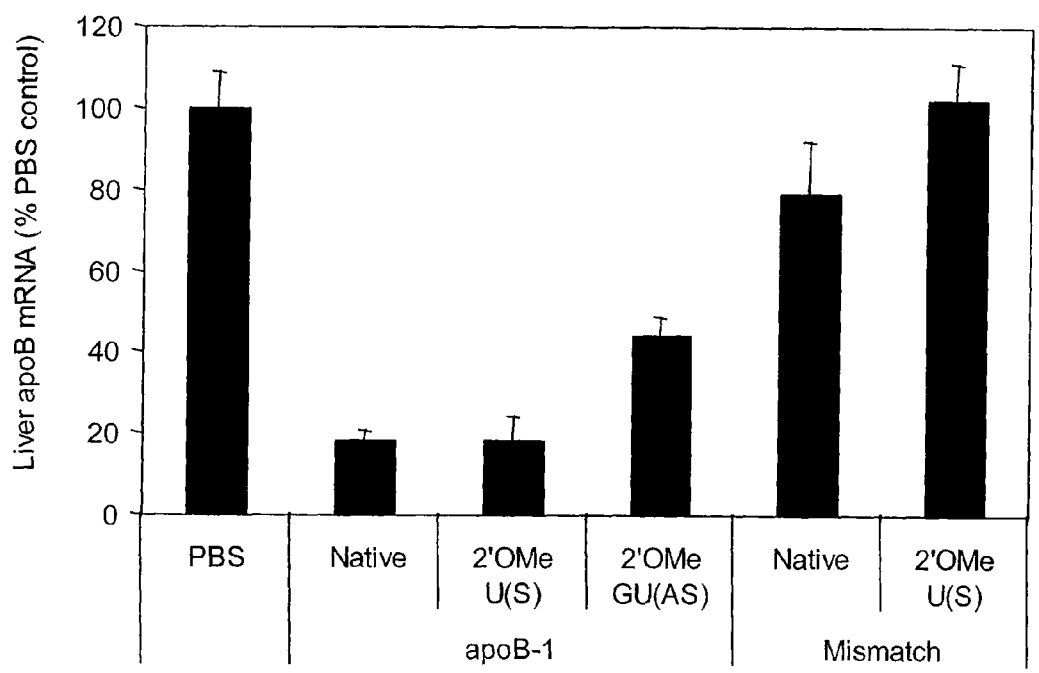

As a direct measure of RNAi mediated knockdown, apoB mRNA was determined in the liver two days after final siRNA treatment (FIG. 10d). In both the native and 2'OMe U(S) modified apoB-1 treated groups, apoB mRNA levels were significantly reduced compared to PBS treated animals (18+/−2% and 18+/−5% of controls respectively). By comparison, mice treated with 2'OMe GU(AS) modified apoB-1 siRNA displayed less pronounced silencing of apoB mRNA (44+/−4% of controls), correlating with reduced in vitro RNAi activity of this modified siRNA (see, FIG. 9). ApoB mRNA levels in the modified mismatch group were equivalent to PBS controls (FIG. 10d) while the native mismatch siRNA caused a modest reduction in apoB mRNA levels (79+/−12% of PBS controls). The modest reduction in liver apoB mRNA observed with the native mismatch siRNA was apparent in three separate experiments and correlated with interferon release and symptoms of toxicity associated with systemic administration and delivery of the unmodified siRNA.

Figure 10E:
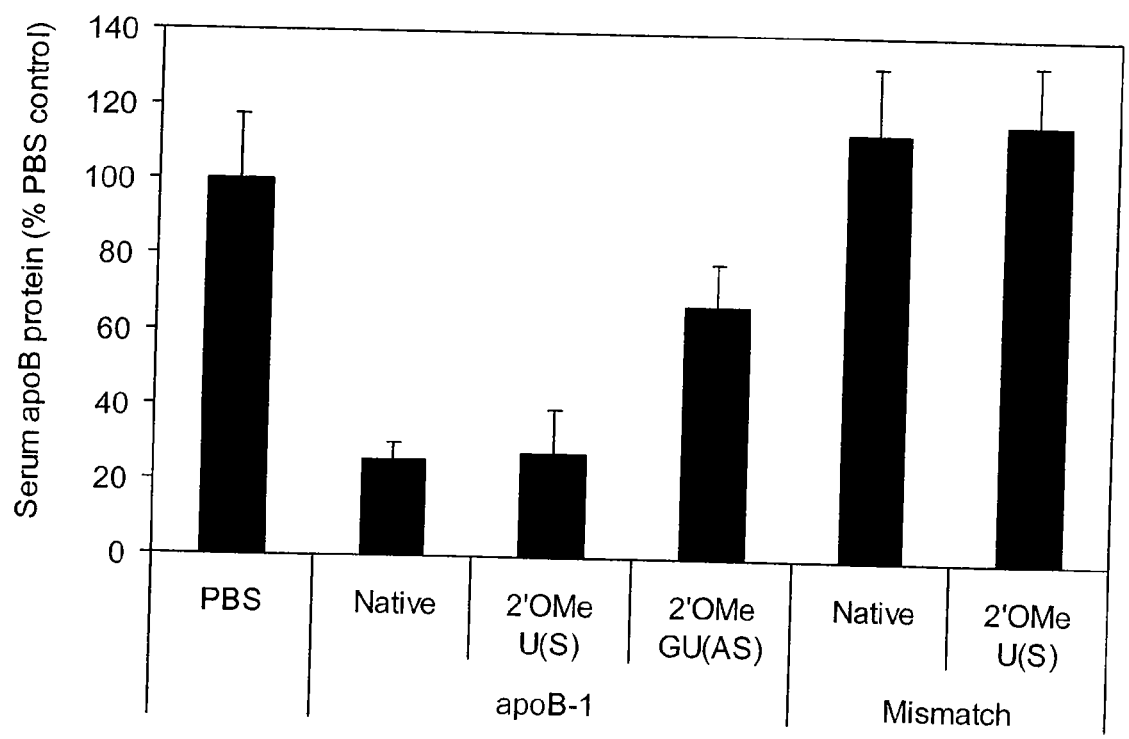
Figure 10F:
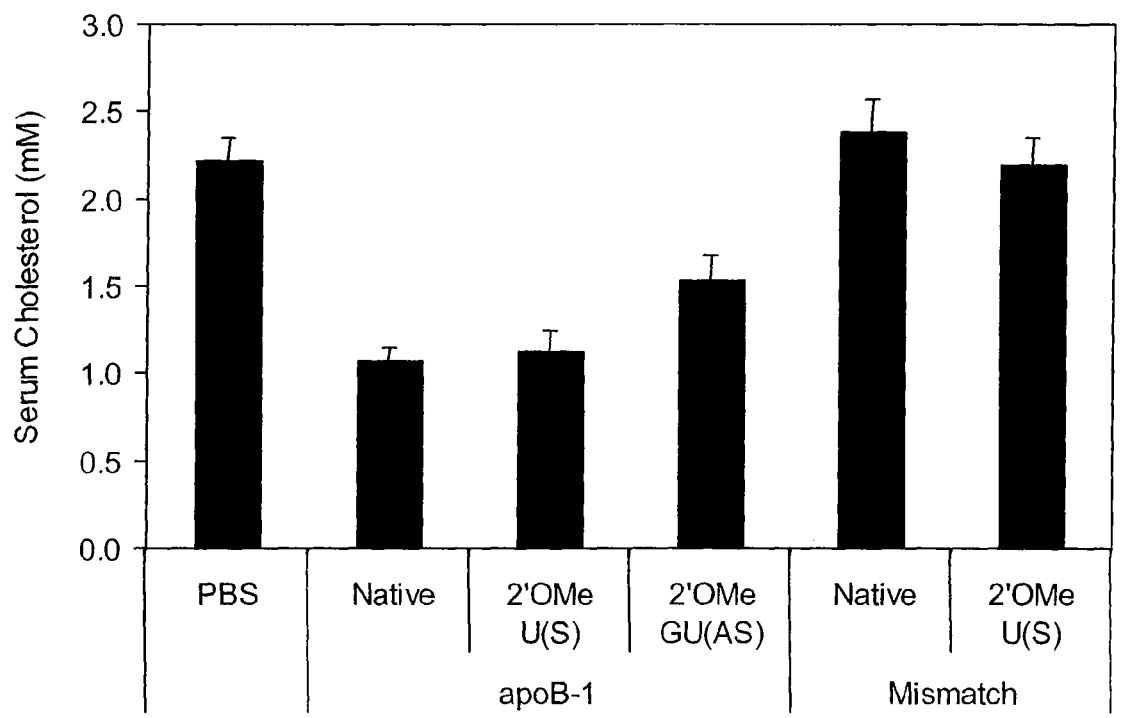

Silencing of apoB mRNA in the liver resulted in proportional, sequence-specific reductions in serum apoB protein. Mice treated with native, 2'OMe U(S), or GU(AS) modified apoB-1 siRNA had serum apoB protein levels that were 26%, 28%, and 47% of the PBS treated animals, respectively (FIG. 10e). Functional silencing of apoB expression was also reflected in significant reductions in serum cholesterol that correlated with the relative potency of mRNA and protein knockdown by the apoB-1 duplexes. Mice treated with native, 2'OMe U(S), or GU(AS) modified apoB-1 siRNA displayed serum cholesterol levels that were 48%, 51%, and 69% of cholesterol levels in the PBS control group (FIG. 10f). Neither mismatch siRNAs had any effect on serum apoB protein or cholesterol (FIGS. 10e and 10f). In separate experiments, the non-inflammatory 2'OMe guanosine modified sense apoB-1 demonstrated similar reductions in apoB mRNA, protein, and serum cholesterol levels compared to the native apoB-1 siRNA.

Results from these studies demonstrate that lipid encapsulation of siRNA provides adequate serum stability for systemic applications and negates the need for extensive chemical modifications to the RNA. This, coupled with the effective delivery of the siRNA payload to the target organ, in this case the liver, facilitates the silencing of endogenous genes, exemplified in these studies by apoB, a protein that represents a potential therapeutic target for hypercholesterolemia. Importantly, the 2'OMe modified siRNAs, designed to be non-inflammatory, displayed potency in vivo that is equivalent to the unmodified siRNA but without the immunotoxicities and other off-target effects associated with systemic administration of the unmodified siRNA. The approach described herein can be generally applicable to a wide range of gene targets and is suitable for use in a variety of therapeutic methods.

Discussion

Based on the finding that immune activation by siRNA is sequence-dependent, it has previously been shown to be possible to design active siRNA with negligible immunostimulatory activity by selecting sequences that lack GU-rich motifs (Judge et al., Nat. Biotechnol. 23:457-462 (2005)). However, this strategy significantly limits the number of novel siRNA sequences that can be designed against a given target. Furthermore, it currently requires some degree of screening due to the relatively ill-defined nature of putative RNA immunostimulatory motifs. This study highlights a novel and robust approach to abrogate synthetic siRNA mediated immune stimulation by selective incorporation of 2'OMe modified nucleotides into the siRNA duplex. Remarkably, incorporation of as few as two 2'OMe guanosine or uridine residues in highly immunostimulatory siRNA molecules completely abrogated siRNA mediated interferon and inflammatory cytokine induction in human PBMC and in mice in vivo. This degree of chemical modification represents 5% of the native 2'-OH positions in the siRNA duplex. Since complete abrogation of the immune response required only one of the RNA strands to be selectively modified, 2'OMe modifications could be restricted to the sense strand of the duplex, therefore minimizing the potential for attenuating the potency of the siRNA. These findings have provided a simple rationale for the synthesis of non-immunostimulatory siRNAs based on native sequences with proven RNAi activity. By combining selectively modified siRNA with an effective systemic delivery vehicle such as nucleic acid-lipid particles, potent silencing of an endogenous gene target can be achieved in vivo at therapeutically viable doses without the deleterious side-effects associated with systemic activation of the innate immune response.

Since the 2'-OH in the ribose backbone is a distinguishing feature of RNA, extensive chemical substitutions at this position would be anticipated to disrupt recognition of the modified nucleic acid by an RNA binding receptor pathway. However, this study unexpectedly shows that 2'OMe modified siRNA are rendered non-immunostimulatory despite retaining up to 95% of their native ribonucleotides, including those comprising defined immunostimulatory regions of the RNA. 2'OMe is considered to be a relatively bulky chemical group at the 2' position that sits within the minor groove of an RNA duplex without significantly distorting its A-form helical structure (Chiu et al., RNA 9:1034-1048 (2003); Cummins et al., Nucl. Acids Res. 23:2019-2024 (1995)). This may be sufficient to disrupt interactions between the double-stranded RNA duplex and its putative immune receptor or accessory molecules. The trans-inhibitory effect of 2'-O-methylation, whereby 2'OMe modified ssRNA annealed to unmodified immunostimulatory ssRNA generates a non-immunostimulatory duplex is consistent with such a hypothesis that involves recognition of the siRNA as a double stranded molecule.

A number of other stabilization chemistries are routinely used in synthetic siRNA design in an effort to confer nuclease resistance that may also influence immune recognition and RNAi. Locked nucleic acids (LNA) that contain a 2'-O, 4'-C methylene bridge in the sugar ring have been shown to partially reduce the immunostimulatory activity of an siRNA (Hornung et al., Nat. Med. 11:263-270 (2005)). siRNAs containing inverted deoxy abasic end caps have been found to retain immunostimulatory activity (Morrissey et al., Nat. Biotechnol. 23:1002-1007 (2005)). No evidence of a trans-inhibitory effect was observed with LNA modified duplexes. These observations indicate that immune stimulation by siRNA is particularly sensitive to inhibition by 2'OMe modifications versus other, well characterized, stabilization chemistries.

This study demonstrates that both unmodified and 2'OMe modified synthetic siRNA can mediate potent silencing of the endogenous gene target apoB when encapsulated in lipid particles and administered systemically. Intravenous administration of encapsulated unmodified or modified apoB-1 siRNA resulted in significant reductions in apoB mRNA levels in the liver and concomitant reductions in apoB protein in the blood. Importantly, given the interest in apoB as a therapeutic target for hypercholesterolemia, apoB silencing resulted in a significant reduction in serum cholesterol. Lipid encapsulation confers excellent resistance to degradation by serum nucleases, enabling the in vivo use of minimally modified siRNA duplexes. By preventing the induction of interferons and inflammatory cytokines, the potential for non-specific effects on gene expression is limited while the tolerability of siRNA formulations is improved. Specifically, intravenous administration of encapsulated 2'OMe modified siRNAs are efficacious and well tolerated. These findings advance the use of synthetic siRNA in a broad range of in vivo and therapeutic applications.

Methods siRNA. All siRNA used in these studies were chemically synthesized by Dharmacon (Lafayette, Colo.) and received as desalted, deprotected oligonucleotides. Duplexes were annealed by standard procedures: complementary strands at equimolar concentrations were heated to 90° C. for 2 min. and then cooled slowly at 37° C. for 60 min. Formation of annealed duplexes was confirmed by non-denaturing PAGE analysis. All native and 2'OMe modified sequences are listed in Table 2 above.

Lipid Encapsulation of RNA. siRNA or ssRNA were encapsulated into liposomes by a process of spontaneous vesicle formation followed by stepwise ethanol dilution as described for pDNA by Jeffs et al., *Pharm. Res.* 22:362-372 (2005). Liposomes were composed of the following lipids: synthetic cholesterol (Sigma; St. Louis, Mo.), the phospholipid DSPC (1,2-distearoyl-sn-glycero-3-phosphocholine; Avanti Polar Lipids; Alabaster, Ala.), the PEG-lipid PEG-cDMA (3-N-[(-Methoxy poly(ethylene glycol)2000)carbamoyl]-1,2-dimyrestyloxy-propylamine), and the cationic lipid DLinDMA (1,2-Dilinoleyloxy-3-(N,N-dimethyl)aminopropane) in the molar ratio 48:20:2:30. The lipids PEG-cDMA and DLinDMA (Heyes et al., *J. Control Release* 107:276-287 (2005)) were synthesized at Protiva Biotherapeutics. The resulting stabilized lipid particles were dialyzed in PBS and filter sterilized through a 0.2 µm filter prior to use. Particle sizes of each liposome preparation ranged from 100-130 nm and typically contained 90-95% of siRNA encapsulated within the liposome. Concentration and percent encapsulation of formulated siRNA were determined using the membrane impermeable fluorescent dye, RiboGreen (Molecular Probes; Eugene, Oreg.) before and after the addition of detergent to disrupt the lipid bilayers (Jeffs et al., supra).

Serum Nuclease Protection Assay. Unmodified naked or lipid encapsulated siRNA (0.25 mg/ml) were incubated in 50% mouse serum at 37° C. At the times indicated, aliquots were taken directly into gel loading buffer containing 0.1% SDS and frozen in liquid nitrogen. After the final timepoint, siRNA samples were run on a non-denaturing 20% polyacrylamide TBE gel and visualized by ethidium bromide staining. To confirm that nuclease protection of siRNA was conferred by lipid encapsulation, 0.1% Triton-X100 was added to disrupt lipid bilayer integrity immediately prior to incubation with serum.

Cell Isolation and Culture. Human PBMC were isolated from whole blood from healthy donors by a standard Ficoll-Hypaque density centrifugation technique. For immune stimulation assays, $3 \times 10^5$ freshly isolated PBMC were seeded in triplicate in 96 well plates and cultured in RPMI 1640 medium with 10% FBS, 2 mM glutamine, 100 U/mL penicillin, and 100 µg/mL streptomycin. Liposome encapsulated siRNA were added to cells at the indicated final nucleic acid concentration and culture supernatants were collected after 16-20 h and assayed for IFN-α, IL-6, and TNF-α by sandwich ELISA.

In Vitro RNA Interference Assay. HepG2 cells were seeded into 24 well plates at 20,000 cells/well. To determine in vitro RNAi activity of 2'OMe modified ApoB siRNA, HepG2 cultures were treated, in triplicate, with encapsulated siRNA at nucleic acid concentrations between 0.6 nM and 45 nM. Media was changed 24 h after addition of siRNA and then incubated for an additional 48 h. Human ApoB protein levels were determined in culture supernatants by sandwich ELISA, as detailed in Soutschek et al., *Nature* 432:173 (2004), using polyclonal goat anti-human ApoB capture antibody (Chemicon International) and horseradish peroxidase-conjugated goat anti-human ApoB-100 antibody (Academy Bio-medical) to detect bound ApoB. ELISA plates were developed using TMB substrate, stopped with 2N sulphuric acid and absorbance read at 450 nm minus 570 nm. $A_{450}$ values were normalized against a standard curve generated from untreated HepG2 conditioned media to define the linear range of the ELISA. Mean, residual ApoB protein levels in siRNA treated culture supernatants were calculated as a percentage of PBS treated controls.

In Vivo Cytokine Induction. Animal studies were completed in accordance with the Canadian Council on Animal Care guidelines following approval by the local Animal Care and Use Committee at Protiva Biotherapeutics. 6-8 week old CD1 ICR mice (Harlan; Indianapolis, Ind.) were subjected to a three week quarantine and acclimation period prior to use. Encapsulated siRNA formulations were administered by standard intravenous injection in the lateral tail vein in 0.2 ml PBS. Blood was collected by cardiac puncture 6 h after administration and processed as plasma for cytokine analysis. In RNAi efficacy experiments, plasma was collected from 50 µl test bleeds 6 h after initial siRNA administration.

Cytokine ELISA. All cytokines were quantified using sandwich ELISA kits according to manufacturers instructions. These were mouse and human IFN-α (PBL Biomedical; Piscataway, N.J.), human IL-6 and TNF-α (eBioscience; San Diego, Calif.), and mouse IL-6, TNF-α, and IFN-γ (BD Biosciences; San Diego, Calif.).

What is claimed is:

1. A method for generating a chemically modified double-stranded short interfering nucleic acid (siNA) molecule that directs cleavage of a target RNA via RNA interference and has reduced immunostimulatory properties compared to a corresponding siNA molecule having unmodified nucleotides, said method comprising:
- (a) introducing 2'-O-methyl (2'OMe) nucleotides in one or more of the nucleotide positions of the siNA molecule, wherein
  - (i) each strand of said siNA molecule is about 18 to about 38 nucleotides in length;
  - (ii) one strand of said siNA molecule comprises a nucleotide sequence having sufficient complementarity to said target RNA for the siNA molecule to direct cleavage of the target RNA via RNA interference;
  - (iii) said siNA molecule does not comprise phosphorothioate backbone modifications; and
  - (iv) said 2'OMe nucleotides are not 2'OMe-cytosine nucleotides; and
- (b) assaying the siNA molecule of step (a) under conditions suitable for isolating an siNA molecule having reduced immunostimulatory properties compared to a corresponding siNA molecule having unmodified nucleotides wherein said reduced immunostimulatory properties comprise an abrogated or reduced induction of inflammatory or pro-inflammatory cytokines and/or an abrogated or reduced induction of Toll Like Receptors (TLRs) in response to the siNA being introduced in a cell, tissue, or organism.

2. The method of claim 1, wherein said reduced immunostimulatory properties comprise an abrogated or reduced induction of inflammatory or proinflammatory cytokines in response to the siNA being introduced in a cell, tissue, or organism.

3. The method of claim 2, wherein said cytokine comprises interleukin-6 (IL-6) or tumor necrosis alpha (TNF-α).

4. The method of claim 1, wherein said reduced immunostimulatory properties comprise an abrogated or reduced induction of Toll Like Receptors (TLRs) in response to the siNA being introduced in a cell, tissue, or organism.

5. The method of claim 4, wherein said Toll Like Receptor comprises TLR3, TLR7, TLR8 or TLR9.

6. The method of claim 1, wherein said 2'OMe nucleotides are 2'OMe-guanosine nucleotides, 2'OMe-uridine nucleotides, or combinations thereof.

7. The method of claim 1, wherein less than about 20% of the nucleotides in said siNA molecule comprise 2'OMe nucleotides.

8. The method of claim 1, wherein each strand of said siNA molecule is about 19 to about 25 nucleotides in length.

9. The method of claim 1, wherein said siNA molecule comprises 3' overhangs.

10. The method of claim 1, wherein said siNA molecule is chemically synthesized.

11. The method of claim 1, wherein said siNA molecule is assayed by contacting said siNA molecule with a mammalian responder cell.

* * * * *